US012344608B2

(12) United States Patent
Lindsley et al.

(10) Patent No.: US 12,344,608 B2
(45) Date of Patent: Jul. 1, 2025

(54) POSITIVE MODULATORS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); Darren W. Engers, Brentwood, TN (US); Kayla J. Temple, Spring Hill, TN (US); Alison R. Gregro, Mount Juliet, TN (US); Alexa E. Richardson, Nashville, TN (US); Madeline F. Long, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 18/750,829

(22) Filed: Jun. 21, 2024

(65) Prior Publication Data
US 2025/0011320 A1 Jan. 9, 2025

Related U.S. Application Data

(60) Provisional application No. 63/610,220, filed on Dec. 14, 2023, provisional application No. 63/509,589, filed on Jun. 22, 2023.

(51) Int. Cl.
| | | |
|---|---|---|
| C07D 471/04 | (2006.01) | |
| A61K 31/4545 | (2006.01) | |
| C07B 59/00 | (2006.01) | |

(52) U.S. Cl.
CPC ........ *C07D 471/04* (2013.01); *A61K 31/4545* (2013.01); *C07B 59/002* (2013.01)

(58) Field of Classification Search
CPC .. C07D 471/04; A61K 31/4545; C07B 59/002
See application file for complete search history.

(56) References Cited

U.S. PATENT DOCUMENTS

| | | |
|---|---|---|
| 10,329,289 B2 | 6/2019 | Bao et al. |
| 11,884,676 B2 | 1/2024 | Lindsley et al. |

FOREIGN PATENT DOCUMENTS

| | | | | |
|---|---|---|---|---|
| WO | 2017112719 A1 | 6/2017 | | |
| WO | WO-2017107087 A1 * | 6/2017 | .............. | A61P 25/00 |
| WO | 2018112840 A1 | 6/2018 | | |
| WO | 2018118736 A1 | 6/2018 | | |
| WO | WO-2022015988 A1 * | 1/2022 | .............. | A61P 25/00 |

OTHER PUBLICATIONS

Harbeson, S. L., et al., Deuterium in Drug Discovery and Development, Annual Reports in Medicinal Chemistry, vol. 46, Chapter 24, 2011, 404-415. (Year: 2011).*
1,2-DIBROMOETHANE-D4 (D, 99%). Safety Data Sheet. Cambridge Isotope Laboratories, Inc. pp. 1-10. (Year: 2017).*
Spock, M., et al. ACS Med. Chem. Lett. 2021, 12, 1342-1349. (Year: 2021).*
U.S. Appl. No. 19/002,083, filed Dec. 26, 2024, Lindsley C.*
U.S. Appl. No. 19/002,103, filed Dec. 26, 2024, Lindsley C.*
U.S. Appl. No. 19/002,334, filed Dec. 26, 2024, Lindsley C.*
U.S. Appl. No. 19/002,355, filed Dec. 26, 2024, Lindsley C.*
Gleason, J. D., and Friedman, I. Science. 1970, 169, 1085-1086. (Year: 1970).*
Bodick, N. C., et al. "Effects of xanomeline, a selective muscarinic receptor agonist, on cognitive function and behavioral symptoms in Alzheimer disease." Archives of neurology 54.4 (1997): 465-473.
Bubser, M., et al. "Selective activation of M4 muscarinic acetylcholine receptors reverses MK-801-induced behavioral impairments and enhances associative learning in rodents." ACS chemical neuroscience 5.10 (2014): 920-942.
Bymaster, F. P., et al. "Unexpected antipsychotic-like activity with the muscarinic receptor ligand (5R, 6R) 6-(3-propylthio-1, 2, 5-thiadiazol-4-yl)-1-azabicyclo [3.2. 1] octane." European journal of pharmacology 356.2-3 (1998): 109-119.
Bymaster, F. P., et al. "Potential role of muscarinic receptors in schizophrenia." Life sciences 64.6-7 (1999): 527-534.
Conde-Ceide, S., et al. "Discovery of VU0409551/JNJ-46778212: an mGlu5 positive allosteric modulator clinical candidate targeting schizophrenia." ACS medicinal chemistry letters 6.6 (2015): 716-720.
Felts, A. S., et al. "Discovery of N-(5-fluoropyridin-2-yl)-6-methyl-4-(pyrimidin-5-yloxy) picolinamide (VU0424238): a novel negative allosteric modulator of metabotropic glutamate receptor subtype 5 selected for clinical evaluation." Journal of Medicinal Chemistry 60.12 (2017): 5072-5085.
Garrison, A. T., et al. "Development of VU6019650: a potent, highly selective, and systemically active orthosteric antagonist of the M5 muscarinic acetylcholine receptor for the treatment of opioid use disorder." Journal of Medicinal Chemistry 65.8 (2022): 6273-6286.
Johnson, C. R., et al. "Drug design targeting the muscarinic receptors and the implications in central nervous system disorders." Biomedicines 10.2 (2022): 398.
Morris, L. C., et al. "Discovery of (S)-2-Cyclopentyl-N-((1-Isopropylpyrrolidin2-Yl)-9-Methyl-1-Oxo-2, 9-Dihydro-1 H-Pyrrido [3, 4-b] Indole-4-Carboxamide (VU0453379): a novel, CNS penetrant glucagon-like peptide 1 receptor (GLP-1R) positive allosteric modulator (PAM)." Journal of Medicinal Chemistry 57.23 (2014): 10192-10197.
Shannon, H. E., et al. "Muscarinic receptor agonists, like dopamine receptor antagonist antipsychotics, inhibit conditioned avoidance response in rats." Journal of Pharmacology and Experimental Therapeutics 290.2 (1999): 901-907.

(Continued)

*Primary Examiner* — Eric Olson
*Assistant Examiner* — Samuel L Galster
(74) *Attorney, Agent, or Firm* — Fish & Richardson P.C.

(57) ABSTRACT

Deuterium-labeled 4-((2,3-dihydrobenzo[b][1,4]dioxin-6-yl)oxy)piperidines substituted with pyrrolo[3,4-b]pyridin-5-one, furo[3,4-b]pyridin-5(7H)-one, or [1,2,4]triazolo[4,3-a]pyrimidin-3(2H)-one are positive allosteric modulators of the muscarinic acetylcholine receptor $M_4$ (mAChR $M_4$) and may have use in treating neurological and psychiatric disorders associated with muscarinic acetylcholine receptor dysfunction.

7 Claims, 1 Drawing Sheet

(56) References Cited

OTHER PUBLICATIONS

Shannon, H. E., et al. "Xanomeline, an M1/M4 preferring muscarinic cholinergic receptor agonist, produces antipsychotic-like activity in rats and mice." Schizophrenia research 42.3 (2000): 249-259.
Stanhope, K. J., et al. "The muscarinic receptor agonist xanomeline has an antipsychotic-like profile in the rat." Journal of Pharmacology and Experimental Therapeutics 299.2 (2001): 782-792.
Yu, W., et al. "Discovery of ethyl ketone-based highly selective HDACs 1, 2, 3 inhibitors for HIV latency reactivation with minimum cellular potency serum shift and reduced hERG activity." Journal of Medicinal Chemistry 64.8 (2021): 4709-4729.
Ao et al., "Synthesis of deuterium-labeled crizotinib, a potent and selective dual inhibitor of mesenchymal-epithelial transition factor (c-MET) kinase and anaplastic lymphoma kinase (ALK)," Journal of Labelled Compounds and Radiopharmaceuticals, 2018, 7 pages.
CAS No. 22581-63-1, "1,2-Dibromoethane-d4," Sigma-Aldrich, retrieved on Jan. 16, 2025, retrieved from URL<https://www.sigmaaldrich.com/US/en/product/aldrich/425362>, 9 pages.
CAS No. 530-62-1, "1,1'-Carbonyldiimidazole," Sigma-Aldrich, retrieved on Jan. 16, 2025, retrieved from URL<https://www.sigmaaldrich.com/US/en/product/mm/802301>, 9 pages.
CAS No. 937-14-4, "3-Chloroperbenzoic acid," Sigma-Aldrich, retrieved on Jan. 16, 2025, retrieved from URL<https://www.sigmaaldrich.com/US/en/product/aldrich/273031>, 12 pages.
International Search Report and Written Opinion in International Appln. No. PCT/US2024/035078, mailed on Oct. 8, 2024, 12 pages.

\* cited by examiner

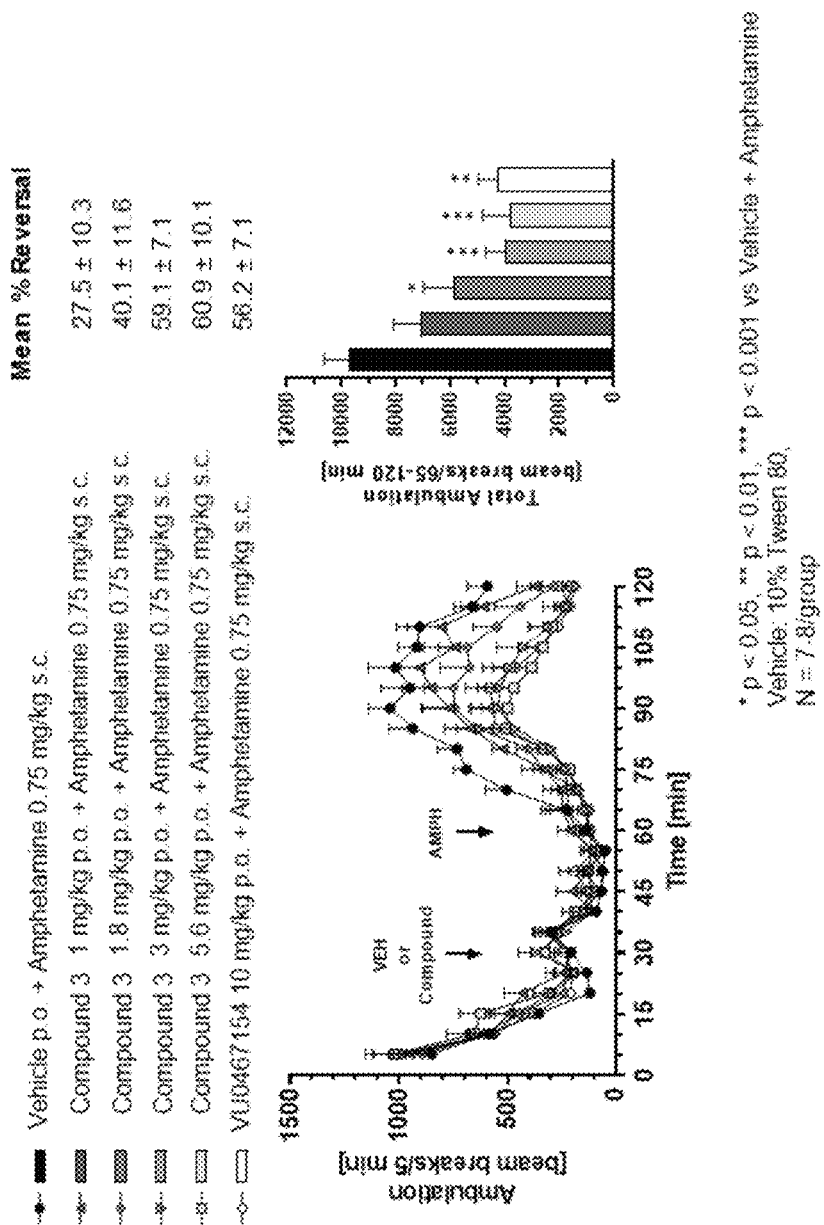

POSITIVE MODULATORS OF THE MUSCARINIC ACETYLCHOLINE RECEPTOR M4

RELATED APPLICATIONS

This application claims priority to U.S. Provisional Application No. 63/509,589, filed Jun. 22, 2023, and U.S. Provisional Application No. 63/610,220, filed Dec. 14, 2023, each of which is hereby incorporated by reference in its entirety.

TECHNICAL FIELD

The present disclosure relates to compounds, compositions, and methods for treating neurological and psychiatric disorders associated with muscarinic acetylcholine receptor dysfunction.

BACKGROUND

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, which are critically involved in cognitive processes. Clinical data supports that cholinergic hypofunction contributes to the cognitive deficits of patients suffering from schizophrenia. Efforts to increase acetylcholine levels have focused on increasing levels of choline, the precursor for acetylcholine synthesis, and on blocking acetylcholinesterase (AChE), the enzyme that metabolizes acetylcholine. As a result, acetylcholinesterase (AChE) inhibitors, which inhibit the hydrolysis of ACh, have been approved in the United States for use in the palliative, but not disease-modifying, treatment of the cognitive deficits in AD patients.

Attempts to augment central cholinergic function through the administration of choline or phosphatidylcholine have not been successful. AChE inhibitors have shown therapeutic efficacy in AD patients, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have restricted their clinical utility. An alternative approach to pharmacologically target cholinergic hypofunction is the activation of mAChRs, which are widely expressed throughout the body.

The mAChRs are members of the family A G protein-coupled receptors (GPCRs) and include five subtypes, designated $M_1$-$M_5$. The $M_1$, $M_3$ and $M_5$ subtypes mainly couple to $G_q$ and activate phospholipase C, whereas the $M_2$ and $M_4$ subtypes mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. Thus, without wishing to be bound by a particular theory, it is believed that selective agonists of mAChR subtypes that regulate processes involved in cognitive function could prove to be superior therapeutics for treatment of psychosis, schizophrenia and related disorders. The muscarinic $M_4$ receptor has been shown to have a major role in cognitive processing and is believed to have a major role in the pathophysiology of psychotic disorders, including schizophrenia.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_4$ has been viewed as the most likely subtype for mediating the effects of muscarinic acetylcholine receptor dysfunction in psychotic disorders, including schizophrenia, cognition disorders, and neuropathic pain. Because of this, considerable effort has been focused on developing selective $M_4$ agonists for treatment of these disorders. Unfortunately, these efforts have been largely unsuccessful because of an inability to develop compounds that are highly selective for the mAChR $M_4$. Because of this, mAChR agonists that have been tested in clinical studies induce a range of adverse effects by activation of peripheral mAChRs. To fully understand the physiological roles of individual mAChR subtypes and to further explore the therapeutic utility of mAChR ligands in psychosis, including schizophrenia, cognition disorders and other disorders, it can be important to develop compounds that are highly selective activators of mAChR $M_4$ and other individual mAChR subtypes.

Previous attempts to develop agonists that are highly selective for individual mAChR subtypes have failed because of the high conservation of the orthosteric ACh binding site. One approach to circumvent problems associated with targeting the highly conserved orthosteric ACh binding site is developing compounds that act at allosteric sites on mAChRs that are removed from the orthosteric site and are less highly conserved. In the case of mAChRs, a major goal has been to develop allosteric ligands that selectively increase activity of mAChR $M_4$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

More recently, muscarinic agonists including xanomeline have been shown to be active in animal models with similar profiles to known antipsychotic drugs, but without causing catalepsy (Bymaster et al., *Eur. J. Pharmacol.* 1998, 356, 109, Bymaster et al., *Life Sci.* 1999, 64, 527; Shannon et al., *J. Pharmacol. Exp. Ther.* 1999, 290, 901; Shannon et al., *Schizophrenia Res.* 2000, 42, 249). Further, xanomeline was shown to reduce psychotic behavioral symptoms such as delusions, suspiciousness, vocal outbursts, and hallucinations in Alzheimer's disease patients (Bodick et al., *Arch. Neurol.* 1997, 54, 465), however treatment induced side effects, e.g., gastrointestinal effects, have severely limited the clinical utility of this compound.

Despite advances in muscarinic acetylcholine receptor research, there is still a scarcity of compounds that are potent, efficacious, and selective activators of the $M_4$ mAChR and also effective in the treatment of neurological and psychiatric disorders associated with cholinergic activity and diseases in which the muscarinic $M_4$ receptor is involved.

SUMMARY

In one aspect, disclosed are compounds of formula (I), or a pharmaceutically acceptable salt thereof

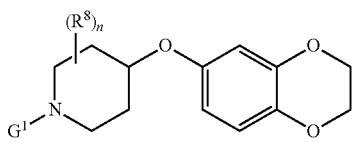

wherein:
G¹ is

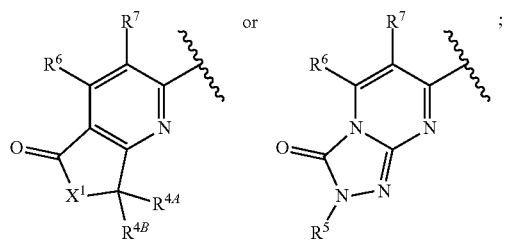

X is $NR^5$ or O;

$R^{4A}$ and $R^{4B}$ are independently hydrogen, $C_{1-4}$ alkyl, $C_{3-4}$ cycloalkyl, or —$C_{1-3}$ alkylene-OH; or $R^{4A}$ and $R^{4B}$ together with the carbon to which they attach form a $C_{3-6}$ cycloalkyl;

$R^5$ is hydrogen, $C_{1-6}$ alkyl, $C_{1-6}$ fluoroalkyl, —$C_{1-6}$ alkylene-$R^y$, —$C_{1-6}$ fluoroalkylene-$R^y$, $G^5$, or —$C_{1-3}$ alkylene-$G^5$;

$R^y$ is —$OR^{5a}$, —$N(R^{5a})_2$, —$C(O)R^{5a}$, —$C(O)OR^{5a}$, or —$C(O)N(R^{5a})_2$;

$R^{5a}$, at each occurrence, is independently hydrogen, $C_{1-4}$ alkyl, $C_{1-4}$ fluoroalkyl, $C_{3-4}$ cycloalkyl, or —$C_{1-3}$ alkylene-$C_{3-4}$ cycloalkyl;

$G^5$ is phenyl, a 4- to 8-membered heterocyclyl containing 1-2 heteroatoms, a 5- to 6-membered heteroaryl containing 1-4 heteroatoms, or a $C_{3-6}$ cycloalkyl, wherein the heteroatoms are independently selected from the group consisting of O, N, and S and $G^5$ is optionally substituted with 1-4 substituents independently selected from the group consisting of $C_{1-4}$ alkyl, halogen, oxo, —$OC_{1-4}$ alkyl, $C_{1-4}$ fluoroalkyl, $C_{3-4}$ cycloalkyl, and —$C_{1-2}$ alkylene-$C_{3-4}$ cycloalkyl;

$R^6$ is hydrogen, halogen, cyano, $C_{1-4}$ alkyl, $C_{1-4}$ fluoroalkyl, $C_{2-4}$ alkenyl, —$OR^{6a}$, —$N(R^{6a})_2$, —$C_{1-3}$ alkylene-$OR^{6a}$, or $C_{3-4}$ cycloalkyl;

$R^{6a}$, at each occurrence, is independently hydrogen, $C_{1-4}$ alkyl, $C_{1-4}$ fluoroalkyl, $C_{3-4}$ cycloalkyl, or —$C_{1-3}$ alkylene-$C_{3-4}$ cycloalkyl;

wherein alternatively, two $R^{6a}$, together with the nitrogen to which they attach form a 4- to 8-membered heterocyclic ring containing the nitrogen attached to $R^{6a}$ and optionally 1 additional heteroatom that is O, N, or S, the heterocyclic ring being optionally substituted with 1-4 substituents independently selected from the group consisting of halogen, $C_{1-2}$ alkyl, and $C_{1-2}$ fluoroalkyl;

$R^7$ is $C_{1-4}$ alkyl, hydrogen, halogen, cyano, $C_{1-4}$ fluoroalkyl, $C_{2-4}$ alkenyl, —$OR^{7a}$, —$C_{1-3}$ alkylene-$OR^{7a}$, $CO_2R^{7a}$, $COR^{7a}$, or $C_{3-6}$ cycloalkyl;

alternatively, $R^6$ and $R^7$, together with the atoms to which they are attached, form an aromatic or non-aromatic ring consisting of 5-7 carbon atoms;

$R^{7a}$ is hydrogen, $C_{1-4}$ alkyl, $C_{1-4}$ fluoroalkyl, $C_{3-4}$ cycloalkyl, or —$C_{1-3}$ alkylene-$C_{3-4}$ cycloalkyl;

$R^8$, at each occurrence, is independently halogen, $C_{1-4}$ alkyl, $C_{1-4}$ fluoroalkyl, or $C_{3-4}$ cycloalkyl; and n is 0, 1, 2, 3, or 4;

wherein at least one hydrogen in the compound is the isotope deuterium ($^2H$).

In another aspect, the invention provides a pharmaceutical composition comprising a compound of formula (I), or a pharmaceutically acceptable salt thereof, and a pharmaceutically acceptable carrier.

Another aspect provides a method of treating a neurological and/or psychiatric disorder associated with muscarinic acetylcholine receptor dysfunction in a mammal, comprising administering to the mammal a therapeutically effective amount of the compound of formula (I), or pharmaceutically acceptable salt or composition thereof.

Another aspect provides a compound of formula (I), or a pharmaceutically acceptable salt or composition thereof, for use in the treatment of a neurological and/or psychiatric disorder associated with muscarinic acetylcholine receptor dysfunction in a mammal.

Another aspect provides use of a compound of formula (I), or a pharmaceutically acceptable salt or composition thereof, for the preparation of a medicament for the treatment of a neurological and/or psychiatric disorder associated with muscarinic acetylcholine receptor dysfunction in a mammal.

In another aspect, the invention provides kits comprising a compound of formula (I), or a pharmaceutically acceptable salt or composition thereof, and instructions for use.

BRIEF DESCRIPTION OF THE DRAWING

The FIGURE shows the effects of Compound 3 in an amphetamine-induced hyperlocomotion assay.

DETAILED DESCRIPTION

Disclosed herein are positive modulators of the muscarinic acetylcholine receptor $M_4$ (mAChR $M_4$), methods of making same, pharmaceutical compositions comprising same, and methods of treating neurological and psychiatric disorders associated with muscarinic acetylcholine receptor dysfunction using same.

The human muscarinic acetylcholine receptor $M_4$ (mAChR $M_4$) is a protein of 479 amino acids encoded by the $CHRM_4$ gene. The molecular weight of the unglycosylated protein is about 54 kDa and it is a transmembrane GPCR. As described above, the mAChR $M_4$ is a member of the GPCR Class A family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved will be advantageous. Binding of the disclosed mAChR M$_4$ positive modulator compounds to mAChR M$_4$ is believed to include binding to an allosteric site distinct from the orthosteric binding site, wherein the mAChR M$_4$ positive modulators may directly or indirectly augment the activity of the mAChR M$_4$ receptor through mechanisms that may include allosteric potentiation, allosteric enhancement, and varying degrees of agonism.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "C$_{1-6}$ alkyl" means a straight or branched chain hydrocarbon containing from 1 to 6 carbon atoms. The term "C$_{1-4}$ alkyl" means a straight or branched chain saturated hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched saturated chain hydrocarbon, for example, of 1 to 6 carbon atoms. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, —CH$_2$CH$_2$CH$_2$CH$_2$—, —CH$_2$CH(CH$_3$)CH$_2$CH$_2$—, and —CH$_2$CH$_2$CH$_2$CH$_2$CH$_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl. Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkylene," as used herein, means an alkylene group, as defined herein, in which one, two, three, four, five, six, seven or eight hydrogen atoms are replaced by fluorine. Representative examples of fluoroalkylene include, but are not limited to —$CF_2$—, —$CH_2CF_2$—, 1,2-difluoroethylene, 1,1,2,2-tetrafluoroethylene, 1,3,3,3-tetrafluoropropylene, 1,1,2,3,3-pentafluoropropylene, and perfluoropropylene such as 1,1,2,2,3,3-hexafluoropropylene.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaromatic ring (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl is an 8- to 12-membered ring system and includes a fused bicyclic heteroaromatic ring system (i.e., 10π electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, tetrahydroisoquinolinyl, 7-oxabicyclo[2.2.1]heptanyl, hexahydro-2H-cyclopenta[b]furanyl, 2-oxaspiro[3.3]heptanyl, 3-oxaspiro[5.5]undecanyl, 6-oxaspiro[2.5]octan-1-yl, and 3-oxabicyclo[3.1.0]hexan-6-yl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentane, hexahydro-2H-2,5-methanocyclopenta[b]furan, hexahydro-1H-1,4-methanocyclopenta[c]furan, azaadamantane (1-azatricyclo[3.3.1.13,7]decane), and oxaadamantane (2-oxatricyclo[3.3.1.13,7]decane). The monocyclic, bicyclic, and tricyclic heterocyclyls are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

Terms such as "alkyl," "cycloalkyl," "alkylene," etc. may be preceded by a designation indicating the number of atoms present in the group in a particular instance (e.g., "$C_{1-4}$ alkyl," "$C_{3-6}$ cycloalkyl," "$C_{1-4}$ alkylene"). These designations are used as generally understood by those skilled in the art. For example, the representation "C" followed by a subscripted number indicates the number of carbon atoms present in the group that follows. Thus, "$C_3$ alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$ alkyl," for example, is an alkyl group having from 1 to 4 carbon atoms, however arranged (i.e., straight chain or branched).

The terms "parent molecule" or "parent molecular moiety" refer to the entire portion of a molecule to which a substituent is attached, i.e., the remainder of the molecule.

The term "sulfonamide," as used herein, means —S(O)$_2$NR$^z$— or —NR$^z$S(O)—, wherein R$^z$ may be hydrogen, alkyl, cycloalkyl, aryl, heteroaryl, heterocycle, alkenyl, or heteroalkyl.

The term "substituents" refers to a group "substituted" on a group such as an alkyl, alkenyl, alkynyl, aryl, heteroaryl, cycloalkyl, heteroalkyl, or heterocycle group, at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. In some embodiments, a group is optionally substituted. In some embodiments, a group is optionally substituted with 1, 2, 3, 4, or 5 substituents. In some embodiments, an aryl, heteroaryl, cycloalkyl, or heterocycle is optionally substituted with 1, 2, 3, 4, or 5 substituents. In some embodiments, an aryl, heteroaryl, cycloalkyl, or heterocycle may be independently unsubstituted or substituted with 1, 2, or 3 substituents.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

The term "orthosteric site" as used herein refers to the primary binding site on a receptor that is recognized by the endogenous ligand or agonist for that receptor. For example, the orthosteric site in the mAChR $M_4$ receptor is the site that acetylcholine binds.

The term "mAChR $M_4$ receptor positive allosteric modulator" as used herein refers to any exogenously administered compound or agent that directly or indirectly augments the activity of the mAChR $M_4$ receptor in the presence or in the absence of acetylcholine, or another agonist, in an animal, in particular a mammal, for example a human. For example, a mAChR $M_4$ receptor positive allosteric modulator can increase the activity of the mAChR $M_4$ receptor in a cell in the presence of extracellular acetylcholine. The cell can be Chinese hamster ovary (CHO-K1) cells transfected with human mAChR $M_4$. The cell can be Chinese hamster ovary (CHO-K1) cells transfected with rat mAChR $M_4$ receptor. The cell can be Chinese hamster ovary (CHO-K1) cells transfected with a mammalian mAChR $M_4$. The term "mAChR $M_4$ receptor positive allosteric modulator" includes a compound that is a "mAChR $M_4$ receptor allosteric potentiator" or a "mAChR $M_4$ receptor allosteric agonist," as well as a compound that has mixed activity comprising pharmacology of both an "mAChR $M_4$ receptor allosteric potentiator" and an "mAChR $M_4$ receptor allosteric agonist." The term "mAChR $M_4$ receptor positive allosteric modulator also includes a compound that is a "mAChR $M_4$ receptor allosteric enhancer."

The term "mAChR $M_4$ receptor allosteric potentiator" as used herein refers to any exogenously administered compound or agent that directly or indirectly augments the response produced by the endogenous ligand (such as acetylcholine) when the endogenous ligand binds to the orthosteric site of the mAChR $M_4$ receptor in an animal, in particular a mammal, for example a human. The mAChR $M_4$ receptor allosteric potentiator binds to a site other than the orthosteric site, that is, an allosteric site, and positively augments the response of the receptor to an agonist or the endogenous ligand. In some embodiments, an allosteric potentiator does not induce desensitization of the receptor, activity of a compound as an mAChR $M_4$ receptor allosteric potentiator provides advantages over the use of a pure mAChR $M_4$ receptor orthosteric agonist. Such advantages can include, for example, increased safety margin, higher tolerability, diminished potential for abuse, and reduced toxicity.

The term "mAChR $M_4$ receptor allosteric enhancer" as used herein refers to any exogenously administered compound or agent that directly or indirectly augments the response produced by the endogenous ligand (such as acetylcholine) in an animal, in particular a mammal, for example a human. In some embodiments, the allosteric enhancer increases the affinity of the natural ligand or agonist for the orthosteric site. In some embodiments, an allosteric enhancer increases the agonist efficacy. The mAChR $M_4$ receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

The term "mAChR $M_4$ receptor allosteric agonist" as used herein refers to any exogenously administered compound or agent that directly activates the activity of the mAChR $M_4$ receptor in the absence of the endogenous ligand (such as acetylcholine) in an animal, in particular a mammal, for example a human. The mAChR $M_4$ receptor allosteric agonist binds to a site that is distinct from the orthosteric acetylcholine site of the mAChR $M_4$ receptor. Because it does not require the presence of the endogenous ligand, activity of a compound as an mAChR $M_4$ receptor allosteric agonist provides advantages if cholinergic tone at a given synapse is low.

The term "mAChR $M_4$ receptor neutral allosteric ligand" as used herein refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

ABBREVIATIONS

AcOH is acetic acid
ADDP is 1,1'-(azodicarbonyl)dipiperidine
AIBN is azobisisobutyronitrile
aq is aqueous
atm is atmosphere(s)
BINAP is 2,2'-bis(diphenylphosphino)-1,1'-binaphthyl
Boc is tert-butoxycarbonyl
Boc$_2$O is di-tert-butyl dicarbonate
B$_2$pin$_2$ is bis(pinacolato)diboron
BrettPhos is 2-(dicyclohexylphosphino)$_{3,6}$-dimethoxy-2', 4',6'-triisopropyl-1,1'-biphenyl
BrettPhos Pd G3 is [(2-di-cyclohexylphosphino-3,6-dimethoxy-2',4',6'-triisopropyl-1,1'-biphenyl)-2-(2'-amino-1,1'-biphenyl)]palladium(II) methanesulfonate
Bu is butyl
t-BuOH is tert-butanol
cat. is catalytic
CDI is 1,1'-carbonyldiimidazole
CD$_2$O is deuterated formaldehyde
Celite® is diatomaceous earth
CSA is (1S,4R)-10-camphorsulfonic acid
DCE is 1,2-dichloroethane
DCM is dichloromethane
DEA is diethylamine
DIAD is diisopropyl azodicarboxylate
DIPEA or DIEA is diisopropylethylamine
DMAP is 4-dimethylaminopyridine
DMF is N,N-dimethylformamide
DMP or Dess-Martin periodinane is 1,1,1-tris(acetyloxy)-1,1-dihydro-1,2-benziodoxol-3-(1H)-one
DMSO is dimethyl sulfoxide
Dowtherm™ A is a eutectic mixture of 26.5% diphenyl+ 73.5% diphenyl oxide
dppp is 1,3-bis(diphenylphosphino)propane
DtBAD is di-tert-butyl-azodicarboxylate eq or eq. is equivalent(s)
EtOAC is ethyl acetate
(4,4'-dtbbpy)NiCl$_2$ is 4,4'-bis(1,1-dimethylethyl)-2,2'-bipyridine]nickel (II) dichloride
Et$_2$O is diethyl ether
EtOH is ethanol
h or hr is hour(s)
Hex is hexane(s)
HMPA is hexamethylphosphoramide
IPA is isopropyl alcohol
KOAc is potassium acetate
LAH is lithium aluminum hydride
LDA is lithium diisopropylamide
LiHMDS/LHMDS is lithium bis(trimethylsilyl)amide
mCPBA is meta-chloroperoxy benzoic acid
MeCN or ACN is acetonitrile
MeI is iodomethane/methyl iodide
MeOD is CD$_3$OD (methanol-d$_4$)
MeOH is methanol
min is minute(s)
NaOAc is sodium acetate
NaOtBu is sodium tert-butoxide
NaOMe is sodium methoxide
NBS is N-bromosuccinimide
NCS is N-chlorosuccinimide
NH$_4$O Ac is ammonium acetate
NMO is 4-methylmorpholine N-oxide
NMP is N-methyl-2-pyrrolidone
PCC is pyridinium chlorochromate
[Pd(allyl)(tBuBrettPhos)]OTf is trifluoromethanesulfonate allyl[(2-Di-tert-butylphosphino-3,6-dimethoxy-2',4',6'-triisopropyl-1,1'-biphenyl)-2-(2'-amino-1,1'-biphenyl)]palladium(II)
Pd$_2$(dba)$_3$ is tris(dibenzylideneacetone)dipalladium(O)
Pd(dppf)Cl$_2$ is [1,1'-bis(diphenylphosphino)ferrocene]dichloropalladium(II)
Pd(OAc)$_2$ is palladium(II)acetate
Pd(PPh$_3$)$_4$ is tetrakis(triphenylphosphine)palladium(O)
PPA is polyphosphoric acid
PPh$_3$ is triphenylphosphine
PPTS is pyridinium p-toluenesulfonate
rt is room temperature
sat. is saturated
sec is second(s)
SCX cartridge or HF SCX cartridge is a strong cation exchanger cartridge (i.e. Agilent part #14256027)
SFC is supercritical fluid chromatography
TBAC or TBACl is tetrabutylammonium chloride
t-BuXPhos is 2-di-tert-butylphosphino-2',4',6'-triisopropylbiphenyl
t-BuXPhos-Pd-G1 is [2-(Di-tert-butylphosphino)-2',4',6'-triisopropyl-1,1'-biphenyl][2-(2-aminoethyl)phenyl)]palladium(II) chloride
TBACl is tetrabutylammonium chloride
TCICA is trichloroisocyanuric acid
TEA or Et$_3$N is triethylamine
TFA is trifluoroacetic acid
THF is tetrahydrofuran
TMB is trimethylboroxine
TsCl is para-toluenesulfonyl chloride
tosyl is para-toluenesulfonyl
Xantphos is 4,5-Bis(diphenylphosphino)-9,9-dimethylxanthene 2. Compounds In one aspect, the invention provides compounds of formula (I), wherein R$^8$, G$^1$, and n are as defined herein.

Unsubstituted or substituted rings (i.e., optionally substituted) such as aryl, heteroaryl, etc. are composed of both a ring system and the ring system's optional substituents. Accordingly, the ring system may be defined independently of its substituents, such that redefining only the ring system leaves any previous optional substituents present. For example, a 5- to 12-membered heteroaryl with optional substituents may be further defined by specifying the ring system of the 5- to 12-membered heteroaryl is a 5- to 6-membered heteroaryl (i.e., 5- to 6-membered heteroaryl ring system), in which case the optional substituents of the 5- to 12-membered heteroaryl are still present on the 5- to 6-membered heteroaryl, unless otherwise expressly indicated.

Where heterocyclic and heteroaromatic ring systems are defined to "contain" or as "containing" specified heteroatoms (e.g., 1-3 heteroatoms independently selected from the group consisting of O, N, and S), any ring atoms of the heterocyclic and heteroaromatic ring systems that are not one of the specified heteroatoms are carbon atoms.

In the following, numbered embodiments of the invention are disclosed. The first embodiment is denoted E1, subsequent embodiments are denoted E1.1, E1.2, E1.3, E2, E3, E3.1, E3.2, E3.3, E3.4, E4, and so forth.

E1. A compound of formula (I), or a pharmaceutically acceptable salt thereof,

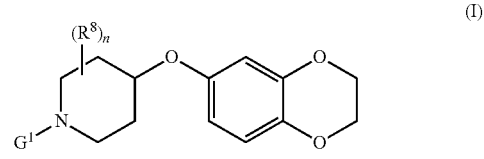

wherein:
G$^1$ is

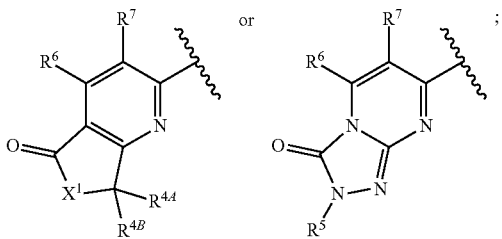

X$^1$ is NR$^5$ or O;
R$^{4A}$ and R$^{4B}$ are independently hydrogen, C$_{1-4}$ alkyl, C$_{3-4}$ cycloalkyl, or —C$_{1-3}$ alkylene-OH; or
R$^{4A}$ and R$^{4B}$ together with the carbon to which they attach form a C$_{3-6}$ cycloalkyl;
R$^5$ is hydrogen, C$_{1-6}$ alkyl, C$_{1-6}$ fluoroalkyl, —C$_{1-6}$ alkylene-R$^y$, —C$_{1-6}$ fluoroalkylene-R$^y$, G$^5$, or —C$_{1-3}$ alkylene-G$^5$;
R$^y$ is —OR$^{5a}$, —N(R$^{5a}$)$_2$, —C(O)R$^{5a}$, —C(O)OR$^{5a}$, or —C(O)N(R$^{5a}$)$_2$;
R$^{5a}$, at each occurrence, is independently hydrogen, C$_{1-4}$ alkyl, C$_{1-4}$ fluoroalkyl, C$_{3-4}$ cycloalkyl, or —C$_{1-3}$ alkylene-C$_{3-4}$ cycloalkyl;
G$^5$ is phenyl, a 4- to 8-membered heterocyclyl containing 1-2 heteroatoms, a 5- to 6-membered heteroaryl containing 1-4 heteroatoms, or a C$_{3-6}$ cycloalkyl, wherein the heteroatoms are independently selected from the group consisting of O, N, and S and $G^5$ is optionally substituted with 1-4 substituents independently selected from the group consisting of $C_{1-4}$ alkyl, halogen, oxo, —$OC_{1-4}$ alkyl, $C_{1-4}$ fluoroalkyl, $C_{3-4}$ cycloalkyl, and —$C_{1-2}$ alkylene-$C_{3-4}$ cycloalkyl;

$R^6$ is hydrogen, halogen, cyano, $C_{1-4}$ alkyl, $C_{1-4}$ fluoroalkyl, $C_{2-4}$alkenyl, —$OR^{6a}$, —$N(R^{6a})_2$, —$C_{1-3}$ alkylene-$OR^{6a}$, or $C_{3-4}$ cycloalkyl;

$R^{6a}$, at each occurrence, is independently hydrogen, $C_{1-4}$ alkyl, $C_{1-4}$ fluoroalkyl, $C_{3-4}$ cycloalkyl, or —$C_{1-3}$ alkylene-$C_{3-4}$ cycloalkyl;

wherein alternatively, two $R^{6a}$, together with the nitrogen to which they attach form a 4- to 8-membered heterocyclic ring containing the nitrogen attached to $R^{6a}$ and optionally 1 additional heteroatom that is O, N, or S, the heterocyclic ring being optionally substituted with 1-4 substituents independently selected from the group consisting of halogen, $C_{1-2}$ alkyl, and $C_{1-2}$ fluoroalkyl;

$R^7$ is $C_{1-4}$ alkyl, hydrogen, halogen, cyano, $C_{1-4}$ fluoroalkyl, $C_{2-4}$alkenyl, —$OR^{7a}$, —$C_{1-3}$ alkylene-$OR^{7a}$, $CO_2R^{7a}$, $COR^{7a}$, or $C_{3-6}$ cycloalkyl;

alternatively, $R^6$ and $R^7$, together with the atoms to which they are attached, form an aromatic or non-aromatic ring consisting of 5-7 carbon atoms;

$R^{7a}$ is hydrogen, $C_{1-4}$ alkyl, $C_{1-4}$ fluoroalkyl, $C_{3-4}$ cycloalkyl, or —$C_{1-3}$ alkylene-$C_{3-4}$ cycloalkyl;

$R^8$, at each occurrence, is independently halogen, $C_{1-4}$ alkyl, $C_{1-4}$ fluoroalkyl, or $C_{3-4}$ cycloalkyl; and n is 0, 1, 2, 3, or 4;

wherein at least one hydrogen in the compound is the isotope deuterium (2H).

E1.1. The compound of E1, or a pharmaceutically acceptable salt thereof, wherein:
$R^6$ is hydrogen, halogen, cyano, $C_{1-4}$ alkyl, $C_{1-4}$ fluoroalkyl, $C_{2-4}$alkenyl, —$OR^{6a}$, —$N(R^{6a})_2$, —$C_{1-3}$ alkylene-$OR^{6a}$, or $C_{3-4}$ cycloalkyl; and
$R^7$ is $C_{1-4}$ alkyl, hydrogen, halogen, cyano, $C_{1-4}$ fluoroalkyl, $C_{2-4}$alkenyl, —$OR^{7a}$, —$C_{1-3}$ alkylene-$OR^{7a}$, $CO_2R^{7a}$, $COR^{7a}$, or $C_{3-6}$ cycloalkyl.

E1.2. The compound of E1, or a pharmaceutically acceptable salt thereof, wherein $R^6$ and $R^7$, together with the atoms to which they are attached, form the aromatic or non-aromatic ring consisting of 5-7 carbon atoms.

E1.3. The compound of E1 or E1.2, or a pharmaceutically acceptable salt thereof, wherein $R^6$ and $R^7$, together with the atoms to which they are attached, form the non-aromatic ring consisting of 5-7 carbon atoms.

E2. The compound of any of E1-E1.3, or a pharmaceutically acceptable salt thereof, wherein $G^1$ is

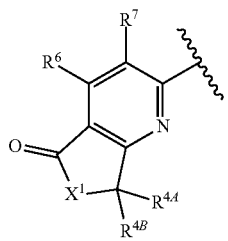

E3. The compound of any of E1-E2, or a pharmaceutically acceptable salt thereof, wherein $R^{4A}$ and $R^{4B}$ are independently hydrogen or $C_{1-4}$ alkyl.

E3.1. The compound of E3, or a pharmaceutically acceptable salt thereof, wherein $R^{4A}$ and $R^{4B}$ are hydrogen.

E3.2. The compound of E3.1, or a pharmaceutically acceptable salt thereof, wherein the hydrogen at $R^{4A}$ and $R^{4B}$ are deuterium (2H).

E3.3. The compound of E3, or a pharmaceutically acceptable salt thereof, wherein $R^{4A}$ is hydrogen and $R^{4B}$ is $C_{1-4}$ alkyl.

E3.4. The compound of any of E1-E3 or E3.3, or a pharmaceutically acceptable salt thereof, wherein the $C_{1-4}$ alkyl at $R^{4A}$ and/or $R^{4B}$ is methyl.

E4. The compound of any of E1-E3.4, or a pharmaceutically acceptable salt thereof, wherein $X^1$ is $NR^5$.

E5. The compound of any of E1-E3.4, or a pharmaceutically acceptable salt thereof, wherein $X^1$ is O.

E6. The compound of any of E1-E1.3, or a pharmaceutically acceptable salt thereof, wherein $G^1$ is

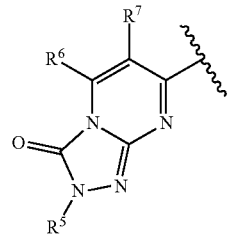

E6.1. The compound of any of E1, E1.2-E1.3, or E6, or a pharmaceutically acceptable salt thereof, wherein $G^1$ is

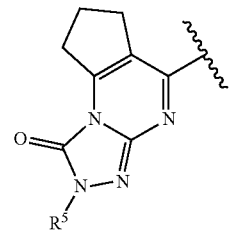

E6.2. The compound of any of E1, E1.2-E1.3, or E6, or a pharmaceutically acceptable salt thereof, wherein $G^1$ is

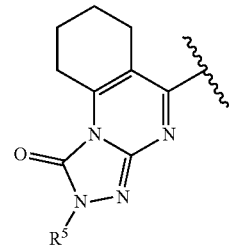

E7. The compound of any of E1-E4 or E6, or a pharmaceutically acceptable salt thereof, wherein $R^5$ is hydrogen, $C_{1-6}$ alkyl, —$C_{1-6}$ alkylene-$R^y$, $G^5$, or —$C_{1-3}$ alkylene-$G^5$.

E7.1. The compound of E7, or a pharmaceutically acceptable salt thereof, wherein $R^5$ is hydrogen.

E7.2. The compound of E7, or a pharmaceutically acceptable salt thereof, wherein $R^5$ is $C_{1-6}$ alkyl.

E7.3. The compound of E7, or a pharmaceutically acceptable salt thereof, wherein $R^5$ is —$C_{1-6}$ alkylene-$R^y$.

E7.4. The compound of any of E1-E4, E6-E7, or E7.3, or a pharmaceutically acceptable salt thereof, wherein —$C_{1-6}$ alkylene-$R^y$ at $R^5$ is —$CH_2CH_2$—$R^y$ or —$CH(CH_3)CH_2$—$R^y$.

E7.5. The compound of E7, or a pharmaceutically acceptable salt thereof, wherein $R^5$ is $G^5$.

E7.6. The compound of E7, or a pharmaceutically acceptable salt thereof, wherein $R^5$ is —$C_{1-3}$ alkylene-$G^5$.

E7.7. The compound of any of E1-E4, E6-E7, or E7.6, or a pharmaceutically acceptable salt thereof, wherein —$C_{1-3}$ alkylene-$G^5$ at $R^5$ is —$CH_2$-$G^5$.

E8. The compound of any of E1-E4, E6-E7, E7.2, E7.4, or E7.7, or a pharmaceutically acceptable salt thereof, wherein the $C_{1-6}$ alkyl at $R^5$ is methyl or ethyl.

E8.1. The compound of E8, or a pharmaceutically acceptable salt thereof, wherein the $C_{1-6}$ alkyl at $R^5$ is methyl.

E8.2. The compound of E8 or E8.1, or a pharmaceutically acceptable salt thereof, wherein the methyl at $R^5$ is CD3.

E9. The compound of any of E1-E4, E6-E7, E7.3-E7.4, E7.7, or E8-E8.2, or a pharmaceutically acceptable salt thereof, wherein $R^y$ is —$OR^{5a}$.

E10. The compound of any of E1-E4, E6-E7, E7.3-E7.4, E7.7, or E8-E9, or a pharmaceutically acceptable salt thereof, wherein $R^{5a}$ is $C_{1-4}$ alkyl.

E10.1. The compound of any of E1-E4, E6-E7, E7.3-E7.4, E7.7, or E8-E10, or a pharmaceutically acceptable salt thereof, wherein the $C_{1-4}$ alkyl at $R^{5a}$ is methyl.

E11. The compound of any of E1-E4, E6-E7, or E7.4-E10.1, or a pharmaceutically acceptable salt thereof, wherein $G^5$ is the optionally substituted 4- to 8-membered heterocyclyl containing 1-2 heteroatoms.

E11.1. The compound of any of E1-E4, E6-E7, or E7.4-E11, or a pharmaceutically acceptable salt thereof, wherein the ring system of the optionally substituted 4- to 8-membered heterocyclyl at $G^5$ is tetrahydrofuran or morpholine.

E11.2. The compound of E11.1, or a pharmaceutically acceptable salt thereof, wherein the ring system of the optionally substituted 4- to 8-membered heterocyclyl at $G^5$ is tetrahydrofuran-3-yl or morpholin-2-yl.

E11.3. The compound of E11.2, or a pharmaceutically acceptable salt thereof, wherein $G^5$ is K or

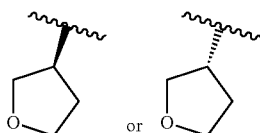

E11.4. The compound of E11.2, or a pharmaceutically acceptable salt thereof, wherein $G^5$ is

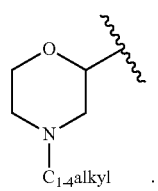

E11.5. The compound of E11.4, or a pharmaceutically acceptable salt thereof, wherein $G^5$ is

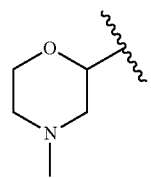

E12. The compound of any of E1-E4, E6-E7, or E7.4-E10.1, or a pharmaceutically acceptable salt thereof, wherein $G^5$ is the optionally substituted $C_{3-6}$ cycloalkyl.

E12.1. The compound of any of E1-E4, E6-E7, E7.4-E10.1, E11.1-E11.2, or E12, or a pharmaceutically acceptable salt thereof, wherein the ring system of the optionally substituted $C_{3-6}$ cycloalkyl at $G^5$ is cyclopropyl or cyclopentyl.

E12.2. The compound of E12.1, or a pharmaceutically acceptable salt thereof, wherein $G^5$ is cyclopropyl or cyclopentyl.

E13. The compound of any of E1-E6 or E7-E12.2, or a pharmaceutically acceptable salt thereof, wherein $R^6$ is hydrogen, $C_{1-4}$ alkyl, halogen, or $C_{3-4}$ cycloalkyl.

E13.1. The compound of E13, or a pharmaceutically acceptable salt thereof, wherein $R^6$ is hydrogen, $C_{1-4}$ alkyl, or halogen.

E13.2. The compound of E13.1, or a pharmaceutically acceptable salt thereof, wherein $R^6$ is hydrogen.

E13.3. The compound of E13.1, or a pharmaceutically acceptable salt thereof, wherein $R^6$ is $C_{1-4}$ alkyl.

E13.4. The compound of any of E1-E6, E7-E13.1 or E13.3, or a pharmaceutically acceptable salt thereof, wherein the $C_{1-4}$ alkyl at $R^6$ is methyl.

E13.5. The compound of E13.1, or a pharmaceutically acceptable salt thereof, wherein $R^6$ is halogen.

E13.6. The compound of any of E1-E6, E7-E13.1, or E13.4-E13.5, or a pharmaceutically acceptable salt thereof, wherein the halogen at $R^6$ is chloro.

E13.7. The compound of E13, or a pharmaceutically acceptable salt thereof, wherein $R^6$ is $C_{3-4}$ cycloalkyl.

E13.8. The compound of any of E1-E6, E7-E13.1, E13.4, or E13.6-E13.7, or a pharmaceutically acceptable salt thereof, wherein the $C_{3-4}$ cycloalkyl at $R^6$ is cyclopropyl.

E14. The compound of any of E1-E6 or E7-E13.8, or a pharmaceutically acceptable salt thereof, wherein $R^7$ is $C_{1-4}$ alkyl.

E14.1. The compound of any of E1-E6 or E7-E14, or a pharmaceutically acceptable salt thereof, wherein the $C_{1-4}$ alkyl at $R^7$ is methyl.

E15. The compound of any of E1-E14.1, or a pharmaceutically acceptable salt thereof, wherein n is 0.

E16. The compound of any of E1-E14.1, or a pharmaceutically acceptable salt thereof, wherein n is 1.

E17. The compound of any of E1-E14.1 or E16, or a pharmaceutically acceptable salt thereof, wherein $R^8$, at each occurrence, is independently $C_{1-4}$ alkyl.

E17.1. The compound of any of E1-E17, or a pharmaceutically acceptable salt thereof, wherein the $C_{1-4}$ alkyl at $R^8$ is methyl.

E18.1. The compound of any of E1-E17.1, or a pharmaceutically acceptable salt thereof, wherein the compound of formula (I) is a compound of formula (Ia):

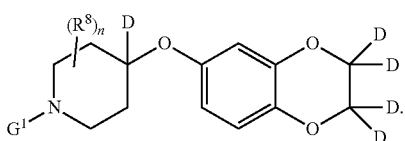

(Ia)

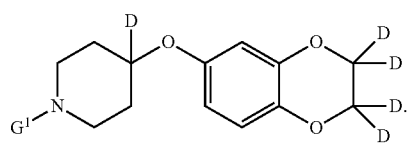

(Ia-1)

E18.2. The compound of any of E1-E17.1, or a pharmaceutically acceptable salt thereof, wherein the compound of formula (I) is a compound of formula (Ib):

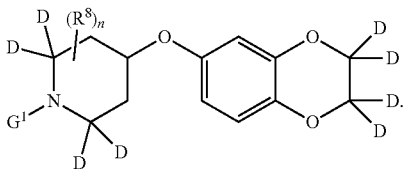

(Ib)

E18.3. The compound of any of E1-E17.1, or a pharmaceutically acceptable salt thereof, wherein the compound of formula (I) is a compound of formula (Ic):

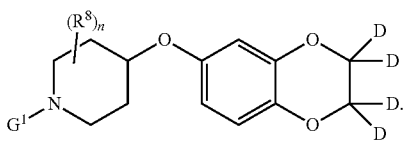

(Ic)

E18.4. The compound of any of E1-E17.1, or a pharmaceutically acceptable salt thereof, wherein the compound of formula (I) is a compound of formula (Id):

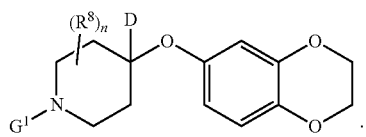

(Id)

E18.5. The compound of any of E1-E17.1, or a pharmaceutically acceptable salt thereof, wherein the compound of formula (I) is a compound of formula (Ie):

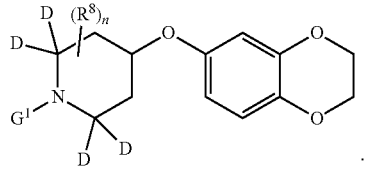

(Ie)

E19.1. The compound of any of E1-E18.1, or a pharmaceutically acceptable salt thereof, wherein the compound of formula (I) is a compound of formula (Ia-1):

E19.2. The compound of any of E1-E18 or E18.2, or a pharmaceutically acceptable salt thereof, wherein the compound of formula (I) is a compound of formula (Ib-1):

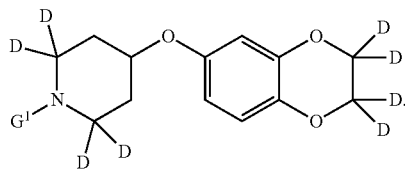

(Ib-1)

E19.3. The compound of any of E1-E18 or E18.3, or a pharmaceutically acceptable salt thereof, wherein the compound of formula (I) is a compound of formula (Ic-1):

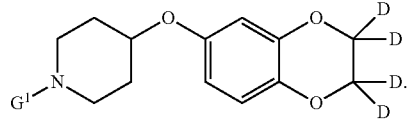

(Ic-1)

E19.4. The compound of any of E1-E18 or E18.3, or a pharmaceutically acceptable salt thereof, wherein the compound of formula (I) is a compound of formula (Ic-2):

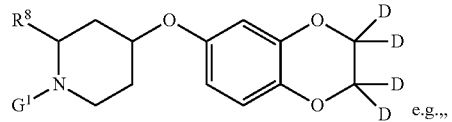

(Ic-2)

e.g.,

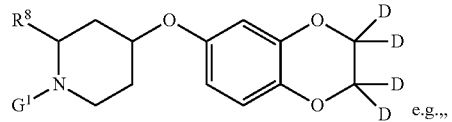

(Ic-2A)

or

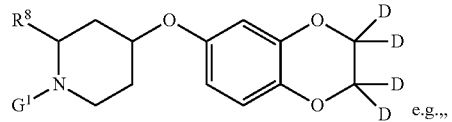

(Ic-2B)

E19.5. The compound of any of E1-E18 or E18.4, or a pharmaceutically acceptable salt thereof, wherein the compound of formula (I) is a compound of formula (Id-1):

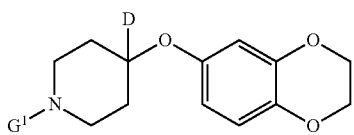

(Id-1)

E19.6. The compound of any of E1-E18 or E18.5, or a pharmaceutically acceptable salt thereof, wherein the compound of formula (I) is a compound of formula (Ie-1):

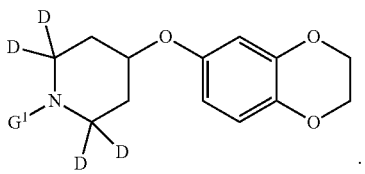

(Ie-1)

E19.7. The compound of any of E1-E19.6, or a pharmaceutically acceptable salt thereof, wherein at least one additional hydrogen in the compound is the isotope deuterium (2H).

E20. The compound of E1 selected from the group consisting of:
2-(4-((2,3-dihydrobenzo[b][1,4]dioxin-6-yl-2,2,3,3-$d_4$)oxy) piperidin-1l-yl-4-d)-3-methyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl-2,2,6,6-$d_4$)-3-methyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl)-3-methyl-6,7-dihydro-5H-pyrrolo[3,4-b]pyridin-5-one;
2-((2R,4S)-4-((2,3-dihydrobenzo[b][1,4]dioxin-6-yl-2,2,3,3-$d_4$)oxy)-2-methylpiperidin-1-yl)-3-methyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl)-3,6-dimethyl-6,7-dihydro-5H-pyrrolo[3,4-b]pyridin-5-one;
6-cyclopropyl-2-(4-((2,3-dihydrobenzo[b][1,4]dioxin-6-yl-2,2,3,3-$d_4$)oxy)piperidin-1-yl)-3-methyl-6,7-dihydro-5H-pyrrolo[3,4-b]pyridin-5-one;
6-cyclopentyl-2-(4-((2,3-dihydrobenzo[b][1,4]dioxin-6-yl-2,2,3,3-$d_4$)oxy)piperidin-1-yl)-3-methyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl)-3-methylfuro[3,4-b]pyridin-5(7H)-one;
2-(4-((2,3-dihydrobenzo[b][1,4]dioxin-6-yl-2,2,3,3-$d_4$)oxy) piperidin-1-yl)-3,7-dimethylfuro[3,4-b]pyridin-5(7H)-one;
2-(4-((2,3-dihydrobenzo[b][1,4]dioxin-6-yl)oxy)piperidin-1-yl-4-d)-3-methyl-6,7-dihydro-5H-pyrrolo[3,4-b]pyridin-5-one;
2-(4-((2,3-dihydrobenzo[b][1,4]dioxin-6-yl)oxy)piperidin-1-yl-2,2,6,6-$d_4$)-3-methyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl)-3,4,6-trimethyl-6,7-dihydro-5H-pyrrolo[3,4-b]pyridin-5-one;
2-(4-((2,3-dihydrobenzo[b][1,4]dioxin-6-yl-2,2,3,3-$d_4$)oxy) piperidin-1-yl)-3,4-dimethyl-6,7-dihydro-5H-pyrrolo[3,4-b]pyridin-5-one;
7-(4-((2,3-dihydrobenzo[b][1,4]dioxin-6-yl-2,2,3,3-$d_4$)oxy) piperidin-1-yl)-6-methyl-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-2-ethyl-6-methyl-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-2-(2-methoxyethyl)-6-methyl-[1,2,4]triazolo[4,3-a]pyrimidin-3(2H)-one;
(R)-7-(4-((2,3-dihydrobenzo[b][1,4]dioxin-6-yl-2,2,3,3-$d_4$) oxy)piperidin-1-yl)-6-methyl-2-(tetrahydrofuran-3-yl)-[1,2,4]triazolo[4,3-a]pyrimidin-3(2H)-one;
(S)-7-(4-((2,3-dihydrobenzo[b][1,4]dioxin-6-yl-2,2,3,3-$d_4$) oxy)piperidin-1-yl)-6-methyl-2-(tetrahydrofuran-3-yl)-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-2,6-dimethyl-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-2-(1-methoxypropan-2-yl)-6-methyl-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-6-methyl-2-((4-methylmorpholin-2-yl) methyl)-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-5,6-dimethyl-[1,2,4]triazolo[4,3-a]pyrimidin-3(2H)-one;
7-(4-((2,3-dihydrobenzo[b][1,4]dioxin-6-yl-2,2,3,3-$d_4$)oxy) piperidin-1-yl)-2,5,6-trimethyl-[1,2,4]triazolo[4,3-a]pyrimidin-3(2H)-one;
5-chloro-7-(4-((2,3-dihydrobenzo[b][1,4]dioxin-6-yl-2,2,3,3-$d_4$)oxy)piperidin-1-yl)-2,6-dimethyl-[1,2,4]triazolo[4,3-a]pyrimidin-3(2H)-one;
5-cyclopropyl-7-(4-((2,3-dihydrobenzo[b][1,4]dioxin-6-yl-2,2,3,3-$d_4$)oxy)piperidin-1-yl)-2,6-dimethyl-[1,2,4]triazolo[4,3-a]pyrimidin-3(2H)-one;
5-cyclopropyl-7-(4-((2,3-dihydrobenzo[b][1,4]dioxin-6-yl-2,2,3,3-$d_4$)oxy)piperidin-1-yl)-6-methyl-2-(methyl-$d_3$)-[1,2,4]triazolo[4,3-a]pyrimidin-3(2H)-one;
5-(4-((2,3-dihydrobenzo[b][1,4]dioxin-6-yl-2,2,3,3-$d_4$)oxy) piperidin-1-yl)-2-methyl-2,6,7,8-tetrahydro-1H-cyclopenta[e][1,2,4]triazolo[4,3-a]pyrimidin-1-one;
5-(4-((2,3-dihydrobenzo[b][1,4]dioxin-6-yl-2,2,3,3-$d_4$)oxy) piperidin-1-yl)-2-methyl-6,7,8,9-tetrahydro-[1,2,4]triazolo[4,3-a]quinazolin-1(2H)-one;
5-(4-((2,3-dihydrobenzo[b][1,4]dioxin-6-yl-2,2,3,3-$d_4$)oxy) piperidin-1-yl)-2,6,7,8-tetrahydro-1H-cyclopenta[e][1,2,4]triazolo[4,3-a]pyrimidin-1-one;
5-(4-((2,3-dihydrobenzo[b][1,4]dioxin-6-yl-2,2,3,3-$d_4$)oxy) piperidin-1-yl)-6,7,8,9-tetrahydro-[1,2,4]triazolo[4,3-a]quinazolin-1(2H)-one;
7-(4-((2,3-dihydrobenzo[b][1,4]dioxin-6-yl-2,2,3,3-$d_4$)oxy) piperidin-1-yl)-5,6-dimethyl-2-(methyl-$d_3$)-[1,2,4]triazolo[4,3-a]pyrimidin-3(2H)-one;
or a pharmaceutically acceptable salt thereof.

E21. A compound of any of E1-E20, or a pharmaceutically acceptable salt thereof, that has at least 50% deuterium incorporation at each deuterium label.

E21.1. The compound of E21, or pharmaceutically acceptable salt thereof, that has at least 55% deuterium incorporation at each deuterium label.

E21.2. The compound of E21.1, or pharmaceutically acceptable salt thereof, that has at least 60% deuterium incorporation at each deuterium label.

E21.3. The compound of E21.2, or pharmaceutically acceptable salt thereof, that has at least 70% deuterium incorporation at each deuterium label.

E21.4. The compound of E21.3, or pharmaceutically acceptable salt thereof, that has at least 75% deuterium incorporation at each deuterium label.

E21.5. The compound of E21.4, or pharmaceutically acceptable salt thereof, that has at least 80% deuterium incorporation at each deuterium label.

E21.6. The compound of E21.5, or pharmaceutically acceptable salt thereof, that has at least 85% deuterium incorporation at each deuterium label.

E21.7. The compound of E21.6, or pharmaceutically acceptable salt thereof, that has at least 90% deuterium incorporation at each deuterium label.

E21.8. The compound of E21.7, or pharmaceutically acceptable salt thereof, that has at least 95% deuterium incorporation at each deuterium label.

E21.9. The compound of E21.8, or pharmaceutically acceptable salt thereof, that has at least 96% deuterium incorporation at each deuterium label.

E21.10. The compound of E21.9, or pharmaceutically acceptable salt thereof, that has at least 97% deuterium incorporation at each deuterium label.

E21.11. The compound of E21.10, or pharmaceutically acceptable salt thereof, that has at least 98% deuterium incorporation at each deuterium label.

E21.12. The compound of E21.11, or pharmaceutically acceptable salt thereof, that has at least 99% deuterium incorporation at each deuterium label.

E21.13. The compound of E21.12, or pharmaceutically acceptable salt thereof, that has at least 99.5% deuterium incorporation at each deuterium label.

E21.14. The compound of E21.13, or pharmaceutically acceptable salt thereof, that has at least 99.9% deuterium incorporation at each deuterium label.

E21.15. The compound of any of E21-E21.14, or pharmaceutically acceptable salt thereof, that has 99-99.9% deuterium incorporation at each deuterium label.

E22. The compound of any of E1-E21.15, or a pharmaceutically acceptable salt thereof, wherein any hydrogen atom in the compound not specified as deuterium represents hydrogen at its natural level of isotopic abundance.

E23. A pharmaceutical composition comprising the compound of any of E1-E22, or a pharmaceutically acceptable salt thereof, and a pharmaceutically acceptable carrier.

E24. A method for treating a neurological and/or psychiatric disorder associated with muscarinic acetylcholine receptor dysfunction in a mammal, comprising administering to the mammal a therapeutically effective amount of the compound of any of E1-E22, or pharmaceutically acceptable salt thereof, or the pharmaceutical composition of E23.

E25. The method of E24, wherein the disorder is associated with a mAChR $M_4$ dysfunction.

E26. The method of E24 or E25, wherein the disorder is a neurological and/or psychiatric disorder associated with mAChR $M_4$ dysfunction.

E27. The method of any of E24-E26, wherein the disorder is selected from the group consisting of Alzheimer's disease, schizophrenia, a sleep disorder, a pain disorder, and a cognitive disorder.

E28. The method of E27, wherein the disorder is Alzheimer's disease.

E29. The method of any of E24-E26, wherein the disorder is selected from the group consisting of psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

E30. A kit comprising the compound of any of E1-E22, or a pharmaceutically acceptable salt thereof, and one or more of: (a) at least one agent known to increase mAChR $M_4$ activity; (b) at least one agent known to decrease mAChR $M_4$ activity; (c) at least one agent known to treat a disorder associated with cholinergic activity; (d) instructions for treating a disorder associated with cholinergic activity; (e) instructions for treating a disorder associated with mAChR $M_4$ receptor activity; and (f) instructions for administering the compound in connection with cognitive or behavioral therapy.

E31. The compound of any of E1-E22, or a pharmaceutically acceptable salt thereof, or the pharmaceutical composition of E23, for use in the treatment of a neurological and/or psychiatric disorder associated with muscarinic acetylcholine receptor dysfunction in a mammal.

E32. The use of the compound of any of E1-E22, or a pharmaceutically acceptable salt thereof, or the pharmaceutical composition of E23 for the preparation of a medicament for the treatment of a neurological and/or psychiatric disorder associated with muscarinic acetylcholine receptor dysfunction in a mammal.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure includes an isotopically-labeled compound, which is identical to those recited in formula (I), but for the fact that one or more atoms are specified as an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O $^{31}$P, $^{32}$P, $^{35}$S $^{18}$F, and $^{36}$Cl, respectively.

Deuterium-labeled compounds disclosed herein may possess certain therapeutic advantages compared to non-labeled analogs, as a result of greater metabolic stability. For example, the disclosed compounds may possess improved pharmacokinetics properties such as increased in vivo half-life, reduced clearance rate, and/or increased bioavailability compared to non-labeled analogs. The improved pharmacokinetic properties may allow for reduced dosage requirements, greater therapeutic index, and/or less frequent dosing to achieve or maintain a therapeutic effect.

The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F.

Isotopically-enriched forms of compounds of formula (I), or any subformulas, may generally be prepared by conventional techniques known to those skilled in the art or by processes analogous to those described in the accompanying Examples using an appropriate isotopically-enriched reagent in place of a non-isotopically-enriched reagent. The extent of isotopic enrichment can be characterized as a percent incorporation of a particular isotope at an isotopically-labeled atom (e.g., % deuterium incorporation at a deuterium label). While the synthetic techniques to access isotopically-enriched compounds can be conventional, the resulting compounds may possess unexpected properties, such as those described herein.

It is understood that some variation of natural isotopic abundance occurs in a synthesized compound depending upon the origin of materials used in the synthesis. The concentration of naturally abundant stable hydrogen and carbon isotopes, notwithstanding this variation, is small and immaterial as compared to the degree of stable isotopic substitution of the deuterated compounds described herein.

In the compounds of formula (I), or any subformulas, any deuterium label, such as "$^2$H", "D" or "deuterium" represents deuterium at an abundance of at least greater than natural abundance of deuterium (e.g., 25%, 50%, 75%, 90%, 99% deuterium incorporation). The amount of deuterium incorporation at a designated position may be measured by analytical methods known to one of ordinary skill in the art, for example, by proton NMR. Any hydrogen atom not specifically designated as deuterium represents hydrogen at its natural isotopic abundance.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Compounds of formula (I) may be synthesized using the processes shown in Schemes 1-5, using suitably deuterium-labeled intermediates and/or reagents.

Scheme 1

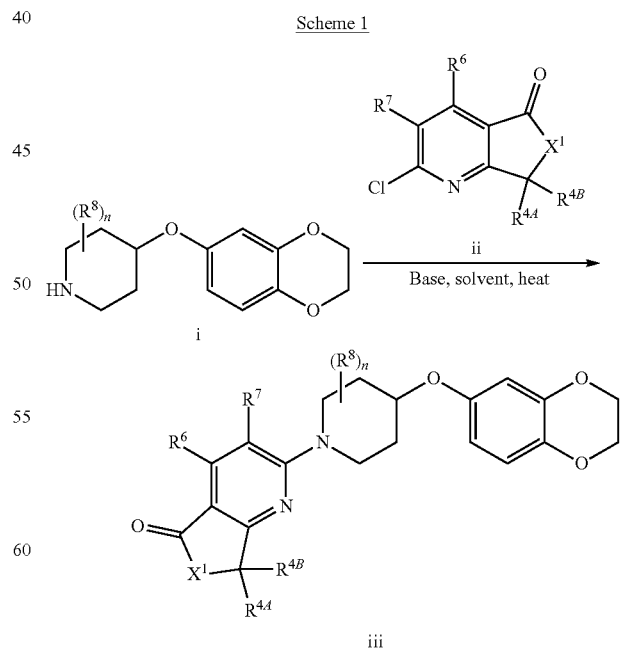

As illustrated in Scheme 1, intermediate i may be subjected to intermediate ii and base (e.g., DIEA or TEA) in solvent (e.g., NMP, DMF) with heating to about 120-160° C. to provide compounds of formula iii.

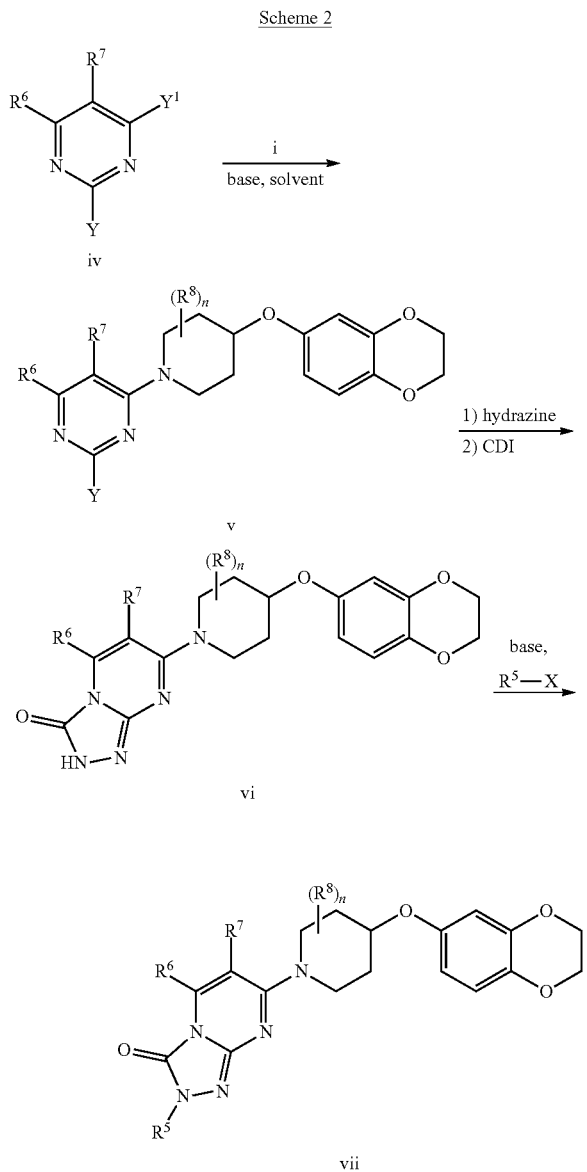

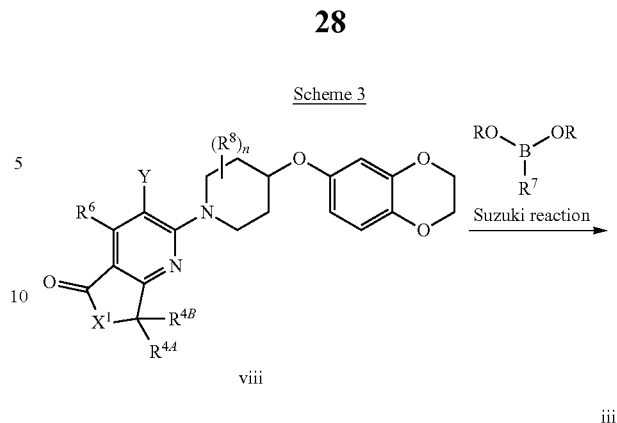

As shown in Scheme 3, intermediates of formula viii (wherein Y is a halogen) may be coupled with a boronic acid or ester under Suzuki coupling conditions, generally known in the art. Coupling reactions may be conducted with a palladium catalyst, such as Pd(dppf)Cl$_2$, and a base (e.g., K$_2$CO$_3$, Cs$_2$CO$_3$) in a solvent mixture of organic solvent, such as DMF or 1,4-dioxane, and water with heating to about 70-90° C. to form compounds of formula iii. Reactions may be facilitated with microwave irradiation.

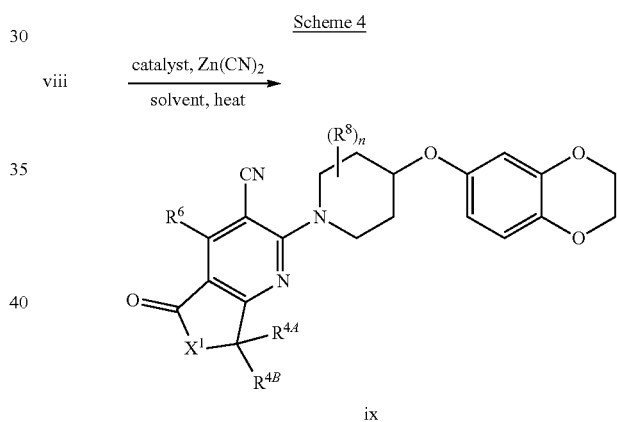

Shown in Scheme 4, intermediates of formula viii (wherein Y is a halogen) may be subjected to catalyst (e.g., Pd(PPh$_3$)$_4$), a cyanide source (e.g., Zn(CN)$_2$) and solvent (e.g., DMF) with heating up to 120-140° C. to afford compounds of formula ix. The reaction may be facilitated with microwave irradiation.

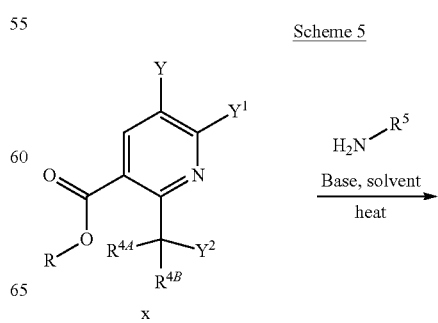

As shown in Scheme 2, intermediate compounds of formula iv (wherein Y and Y$^1$ are fluorine, chlorine, or bromine) may be subjected to standard nucleophilic substitution conditions with amine i, base (e.g., DIEA, Et$_3$N, etc.), and solvent (e.g., NMP, DMF) with heating to about 60-75° C. to provide compounds of formula v. Intermediates of formula v (wherein Y is a halogen) may be subjected to hydrazine in solvent (e.g., ethanol) with heating up to 70-80° C. The intermediate may be subjected to CDI (CAS #530-62-1) in solvent (e.g., 1,4-dioxane) with heat up to 70-85° C. to form compounds of formula vi. Under standard alkylating conditions, generally known in the art, intermediates of formula vi may be subjected to alkylating reagent (R$^5$—X; wherein X is halogen, mesylate or tosylate), base (e.g., K$_2$CO$_3$) in solvent (e.g., DMF) to provide compounds of formula vii.

-continued

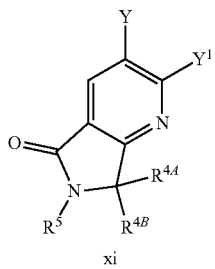

xi

As shown in Scheme 5, ester intermediate x (wherein Y, $Y^1$ and $Y^2$ is a $C_1$, Br, or I) may be subjected to amines, base (e.g., DIEA) and solvent (e.g., THF) with no heating or heating up to 40-50° C. to provide compounds xi.

Suitable boronic acids/esters, amines, and alcohols for coupling reactions described herein may be readily obtained from commercial sources or prepared by standard methods well known to those skilled in the art.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, aerotactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above-described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity

In some embodiments, the disclosed compounds potentiate the agonist response (e.g., acetylcholine) of mAChR $M_4$. In some embodiments, the disclosed compounds increase mAChR $M_4$ response to non-maximal concentrations of agonist in the presence of compound compared to the response to agonist in the absence of compound. The potentiation of mAChR $M_4$ activity can be demonstrated by methodology known in the art. For example, activation of mAChR $M_4$ activity can be determined by measurement of calcium flux in response to agonist, e.g. acetylcholine, in cells loaded with a $Ca^{2+}$-sensitive fluorescent dye (e.g., Fluo-4) and co-expression of a chimeric or promiscuous G protein. In some embodiments, the calcium flux was measured as an increase in fluorescent static ratio. In some embodiments, positive allosteric modulator activity was analyzed as a concentration-dependent increase in the $EC_{20}$ acetylcholine response (i.e. the response of mAChR $M_4$ at a concentration of acetylcholine that yields 20% of the maximal response).

In some embodiments, the disclosed compounds activate mAChR $M_4$ response as an increase in calcium fluorescence in mAChR $M_4$-transfected CHO-K1 cells in the presence of the compound, compared to the response of equivalent CHO-K1 cells in the absence of the compound. In some embodiments, a disclosed compound activates the mAChR $M_4$ response with an $EC_{50}$ of less than about 10 μM, less than about 5 μM, less than about 1 μM, less than about 500 nM, of less than about 100 nM, or less than about 50 nM. In some embodiments, the mAChR $M_4$-transfected CHO-K1 cells are transfected with human mAChR $M_4$ In some embodiments, the mAChR $M_4$-transfected CHO-K1 cells are transfected with rat mAChR $M_4$.

The disclosed compounds may exhibit positive allosteric modulation of mAChR $M_4$ response to acetylcholine as an increase in response to non-maximal concentrations of acetylcholine in CHO-K1 cells transfected with a mAChR $M_4$ in the presence of the compound, compared to the response to acetylcholine in the absence of the compound. In some embodiments, the disclosed compounds exhibit positive allosteric modulation of the mAChR $M_4$ response to acetylcholine with an $EC_{50}$ of less than about 10 μM, less than about 5 μM, less than about 1 μM, less than about 500 nM, or less than about 100 nM. In some embodiments, the $EC_{50}$ for positive allosteric modulation is determined in CHO-K1 cells are transfected with a mAChR $M_4$. In some embodiments, the mAChR $M_4$ transfected human mAChR $M_4$. In some embodiments, the mAChR $M_4$ transfected rat mAChR $M_4$.

A disclosed compound can have selectivity for the mAChR $M_4$ receptor vis-à-vis one or more of the mAChR $M_1$, $M_2$, $M_3$ or $M_5$ receptors. For example, the disclosed compounds may activate mAChR $M_4$ response in mAChR $M_4$-transfected CHO-K1 cells with an $EC_{50}$ less than the $EC_{50}$ for one or more of mAChR $M_1$, $M_2$, $M_3$ or $M_5$-transfected CHO-K1 cells. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_1$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, a disclosed compound can activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, a disclosed compound can activate mAChR $M_4$ response with an $EC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, or greater than about 500-fold less than that for the mAChR $M_1$, $M_2$, $M_3$, or $M_5$ receptors.

The disclosed compounds may activate mAChR $M_4$ response in $M_4$-transfected CHO-K1 cells with an $EC_{50}$ of less than about 10 μM and exhibits a selectivity for the $M_4$ receptor vis-à-vis one or more of the mAChR $M_1$, $M_2$, $M_3$, or $M_5$ receptors. For example, in some embodiments, the compound can have an $EC_{50}$ of less than about 10 μM, of less than about 5 M, of less than about 1 μM, of less than about 500 nM, of less than about 100 nM, or of less than about 50 nM; and the compound can also activate mAChR $M_4$ response with an $EC_{50}$ of about 5-fold less, 10-fold less, 20-fold less, 30-fold less, 50-fold less, 100-fold less, 200-fold less, 300-fold less, 400-fold less, or greater than about 500-fold less than that for mAChR $M_1$. In some embodiments, the compound can have an $EC_{50}$ of less than about 10 μM, of less than about M, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with an $EC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with $EC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, $M_2$, $M_3$, or $M_5$ receptors, or greater than about 500-fold less than that for the mAChR $M_1$, $M_2$, $M_3$, or $M_5$ receptors.

In vivo efficacy for disclosed compounds can be measured in a number of preclinical rat behavioral models where known, clinically useful antipsychotics display similar positive responses. For example, disclosed compounds may reverse amphetamine-induced hyperlocomotion in male Sprague-Dawley rats at doses ranging from 1 to 100 mg/kg p.o.

3. Pharmaceutical Compositions and Formulations

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition or formulation may exhibit positive allosteric modulation of mAChR $M_4$ with an $EC_{50}$ of less than about 10 µM, less than about 5 µM, less than about 1 µM, less than about 500 nM, or less than about 100 nM. The pharmaceutical composition or formulation may exhibit positive allosteric modulation of mAChR $M_4$ with an $EC_{50}$ of between about 10 µM and about 1 nM, about 1 µM and about 1 nM, about 100 nM and about 1 nM, or between about 10 nM and about 1 nM.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I).

4. Methods of Use

The disclosed compounds, pharmaceutical compositions and formulations may be used in methods for treatment of disorders, such as neurological and/or psychiatric disorders, associated with muscarinic acetylcholine receptor dysfunction. The disclosed compounds and pharmaceutical compositions may also be used in methods for the potentiation of muscarinic acetylcholine receptor activity in a mammal, and in methods for enhancing cognition in a mammal. The methods further include cotherapeutic methods for improving treatment outcomes in the context of cognitive or behavioral therapy. In the methods of use described herein, additional therapeutic agent(s) may be administered simultaneously or sequentially with the disclosed compounds and compositions.

a. Treating Disorders

The disclosed compounds, pharmaceutical compositions and formulations may be used for treating disorders, or used in methods for treatment of disorders, such as neurological and/or psychiatric disorders, associated with muscarinic acetylcholine receptor dysfunction. The methods of treatment may comprise administering to a subject in need of such treatment a therapeutically effective amount of the compound of formula (I), or a pharmaceutical composition comprising a therapeutically effective amount of a compound of formula (I).

In some embodiments, the disclosure provides a method for enhancing cognition in a mammal comprising the step of administering to the mammal a therapeutically effective amount of the compound of formula (I), or a pharmaceutical composition comprising a therapeutically effective amount of a compound of formula (I).

The compounds and compositions disclosed herein may be useful for treating, preventing, ameliorating, controlling or reducing the risk of a variety of disorders associated with selective mAChR $M_4$ receptor activation. For example, a treatment can include selective mAChR $M_4$ receptor activation to an extent effective to affect cholinergic activity. A disorder can be associated with cholinergic activity, for example cholinergic hypofunction. Thus, provided is a method of treating or preventing a disorder in a subject comprising the step of administering to the subject at least one disclosed compound or at least one disclosed pharmaceutical composition, in an amount effective to treat the disorder in the subject.

Also provided is a method for the treatment of one or more disorders associated with mAChR $M_4$ receptor activity in a subject comprising the step of administering to the subject a therapeutically effective amount of the compound of formula (I), or a pharmaceutically acceptable salt thereof, or a pharmaceutical composition comprising a therapeutically effective amount of a compound of formula (I), or a pharmaceutically acceptable salt thereof.

In some embodiments, the disclosure provides a compound of formula (I), or a pharmaceutically acceptable salt thereof, for use in a method for the treatment of a disorder associated with the mAChR $M_4$ receptor. In some embodiments, the disclosure provides a pharmaceutical composition comprising a compound of formula (I), or a pharmaceutically acceptable salt thereof, for use in a method for the treatment of a disorder associated with the mAChR $M_4$ receptor.

In some embodiments, the disclosure provides a compound of formula (I), or a pharmaceutically acceptable salt thereof, for use in the manufacture of a medicament for the treatment of a disorder associated with the mAChR M$_4$ receptor.

In some embodiments, the disclosure provides a method for the treatment of a disorder associated with muscarinic acetylcholine receptor dysfunction in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, the disclosure provides a compound of formula (I), or a pharmaceutically acceptable salt thereof, for use in a method for the treatment of a disorder associated with muscarinic acetylcholine receptor dysfunction in a mammal.

In some embodiments, the disclosure provides a pharmaceutical composition comprising a compound of formula (I), or a pharmaceutically acceptable salt thereof, for use in a method for the treatment of a disorder associated with muscarinic acetylcholine receptor dysfunction in a mammal.

In some embodiments, the disclosure provides a compound of formula (I), or a pharmaceutically acceptable salt thereof, for use in the manufacture of a medicament for the treatment of a disorder associated with muscarinic acetylcholine receptor dysfunction in a mammal.

In some embodiments, the disclosed compounds and compositions have utility in treating a variety of neurological, psychiatric and cognitive disorders associated with the mAChR M$_4$ receptor, including one or more of the following conditions or diseases: schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In some embodiments, the psychotic disorder is a psychosis associated with an illness selected from major depressive disorder, affective disorder, bipolar disorder, electrolyte disorder, Alzheimer's disease, neurological disorder, hypoglycemia, AIDS, lupus, and post-traumatic stress disorder.

In some embodiments, the disclosure provides a compound of formula (I), or a pharmaceutically acceptable salt thereof, for use in a method for the treatment of a neurological, psychiatric, or cognitive disorder associated with the mAChR M$_4$ receptor, in particular, the disorders described herein. In some embodiments, the disclosure provides a pharmaceutical composition comprising a compound of formula (I), or a pharmaceutically acceptable salt thereof, for use in a method for the treatment of a neurological, psychiatric, or cognitive disorder associated with the mAChR M$_4$ receptor, in particular, the disorders described herein. In some embodiments, the disclosure provides a compound of formula (I), or a pharmaceutically acceptable salt thereof, for use in the manufacture of a medicament for the treatment of a neurological, psychiatric, or cognitive disorder associated with the mAChR M$_4$ receptor, in particular, the disorders described herein.

In some embodiments, the disorder is a neurological disorder selected from brain tumor, dementia with Lewy bodies, multiple sclerosis, sarcoidosis, Lyme disease, syphilis, Alzheimer's disease, Parkinson's disease, and anti-NMDA receptor encephalitis.

In some embodiments, the disorder is a psychotic disorder selected from schizophrenia, brief psychotic disorder, schizophreniform disorder, schizoaffective disorder, delusional disorder, and shared psychotic disorder. In some embodiments, the schizophrenia is selected from catastrophic schizophrenia, catatonic schizophrenia, paranoid schizophrenia, residual schizophrenia, disorganized schizophrenia, and undifferentiated schizophrenia. In some embodiments, the disorder is selected from schizoid personality disorder, schizotypal personality disorder, and paranoid personality disorder. In some embodiments, the psychotic disorder is due to a general medical condition and is substance-induced or drug-induced (phencyclidine, ketamine and other dissociative anesthetics, amphetamine and other psychostimulants, and cocaine).

In some embodiments, the present disclosure provides a method for treating a cognitive disorder, comprising administering to a patient in need thereof an effective amount of a compound or a composition of the present disclosure. In some embodiments, cognitive disorders include dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse), delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

The text revision of the fourth edition of the Diagnostic and Statistical Manual of Mental Disorders (DSM-IV-TR) (2000, American Psychiatric Association, Washington DC) provides a diagnostic tool that includes cognitive disorders including dementia, delirium, amnestic disorders and age-related cognitive decline. The fifth edition of the Diagnostic and Statistical Manual of Mental Disorders (DSM-5) (2013, American Psychiatric Association, Washington DC) provides a diagnostic tool for neurocognitive disorders (NCDs) that include delirium, followed by the syndromes of major NCD, mild NCD, and their etiological subtypes. The major or mild NCD subtypes include NCD due to Alzheimer's disease, vascular NCD, NCD with Lewy bodies, NCD due to Parkinson's disease, frontotemporal NCD, NCD due to traumatic brain injury, NCD due to HIV infection, substance/medication-induced NCD, NCD due to Huntington's disease, NCD due to prion disease, NCD due to another medical condition, NCD due to multiple etiologies, and unspecified NCD. The NCD category in DSM-5 encompasses the group of disorders in which the primary clinical deficit is in cognitive function, and that are acquired rather than developmental. As used herein, the term "cognitive disorders" includes treatment of those cognitive disorders and neurocognitive disorders as described in DSM-IV-TR or DSM-5. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In some embodiments, the present disclosure provides a method for treating schizophrenia or psychosis, comprising administering to a patient in need thereof an effective amount of a compound or composition of the present disclosure. Particular schizophrenia or psychosis pathologies are paranoid, disorganized, catatonic or undifferentiated schizophrenia and substance-induced psychotic disorder. DSM-IV-TR provides a diagnostic tool that includes paranoid, disorganized, catatonic, undifferentiated or residual schizophrenia, and substance-induced psychotic disorder. DSM-5 eliminated the subtypes of schizophrenia, and instead includes a dimensional approach to rating severity for the core symptoms of schizophrenia, to capture the heterogeneity in symptom type and severity expressed across individuals with psychotic disorders. As used herein, the term "schizophrenia or psychosis" includes treatment of those mental disorders as described in DSM-IV-TR or DSM-5. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In some embodiments, the present disclosure provides a method for treating pain, comprising administering to a patient in need thereof an effective amount of a compound or composition of the present disclosure. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

The compounds and compositions may be further useful in a method for the prevention, treatment, control, amelioration, or reduction of risk of the diseases, disorders and conditions noted herein. The compounds and compositions may be further useful in a method for the prevention, treatment, control, amelioration, or reduction of risk of the aforementioned diseases, disorders and conditions, in combination with other agents.

In the treatment of conditions which require activation of mAChR $M_4$, an appropriate dosage level may be about 0.01 to 500 mg per kg patient body weight per day, which can be administered in single or multiple doses. The dosage level may be about 0.1 to about 250 mg/kg per day, or about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the disclosure relates to a method for activating mAChR $M_4$ receptor activity in at least one cell, comprising the step of contacting the at least one cell with at least one disclosed compound or at least one product of a disclosed method in an amount effective to activate mAChR $M_4$ in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for activating mAChR $M_4$ activity in a subject, comprising the step of administering to the subject at least one disclosed compound or at least one product of a disclosed method in a dosage and amount effective to activating mAChR $M_4$ activity in the subject. In some embodiments, the subject is mammalian, for example, human. In some embodiments, the mammal has been diagnosed with a need for mAChR $M_4$ agonism prior to the administering step. In some embodiments, the mammal has been diagnosed with a need for mAChR $M_4$ activation prior to the administering step. In some embodiments, the method further comprises the step of identifying a subject in need of mAChR $M_4$ agonism.

In some embodiments, the invention relates to a method for the treatment of a disorder associated with selective mAChR $M_4$ activation, for example, a disorder associated with cholinergic activity, in a mammal comprising the step of administering to the mammal at least one disclosed compound or at least one product of a disclosed method in a dosage and amount effective to treat the disorder in the mammal. In some embodiments, the mammal is a human. In some embodiments, the mammal has been diagnosed with a need for treatment for the disorder prior to the administering step. In some embodiments, the method further comprises the step of identifying a subject in need of treatment for the disorder.

In some embodiments, the disorder can be selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

In some embodiments, the disorder is Alzheimer's disease.

b. Potentiation of Muscarinic Acetylcholine Receptor Activity

In some embodiments, the disclosure relates to a method for potentiation of muscarinic acetylcholine receptor activity in a mammal comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, the disclosure provides a compound of formula (I), or a pharmaceutically acceptable salt thereof, for use in a method for the potentiation of muscarinic acetylcholine receptor activity in a mammal. In some embodiments, the disclosure provides a pharmaceutical composition comprising a compound of formula (I), or a pharmaceutically acceptable salt thereof, for use in a method for the potentiation of muscarinic acetylcholine receptor activity in a mammal.

In some embodiments, the disclosure provides a compound of formula (I), or a pharmaceutically acceptable salt thereof, for use in the manufacture of a medicament for the potentiation of muscarinic acetylcholine receptor activity in a mammal.

In some embodiments, potentiation of muscarinic acetylcholine receptor activity increases muscarinic acetylcholine receptor activity. In some embodiments, potentiation of muscarinic acetylcholine receptor activity is partial agonism of the muscarinic acetylcholine receptor. In some embodiments, potentiation of muscarinic acetylcholine receptor activity is positive allosteric modulation of the muscarinic acetylcholine receptor.

In some embodiments, the compound administered exhibits potentiation of mAChR $M_4$ with an $EC_{50}$ of less than about 10 µM, less than about 5 µM, less than about 1 µM, less than about 500 nM, or less than about 100 nM. In some embodiments, the compound administered exhibits potentiation of mAChR $M_4$ with an $EC_{50}$ of between about 10 µM and about 1 nM, about 1 µM and about 1 nM, about 100 nM and about 1 nM, or about 10 nM and about 1 nM.

In some embodiments, the mammal is a human. In some embodiments, the mammal has been diagnosed with a need for potentiation of muscarinic acetylcholine receptor activity prior to the administering step. In some embodiments, the method further comprises the step of identifying a mammal in need of potentiating muscarinic acetylcholine receptor activity. In some embodiments, the potentiation of muscarinic acetylcholine receptor activity treats a disorder associated with muscarinic acetylcholine receptor activity in the mammal. In some embodiments, the muscarinic acetylcholine receptor is mAChR $M_4$.

In some embodiments, potentiation of muscarinic acetylcholine receptor activity in a mammal is associated with the treatment of a neurological and/or psychiatric disorder associated with a muscarinic receptor dysfunction, such as a neurological or psychiatric disorder disclosed herein. In some embodiments, the muscarinic receptor is mAChR $M_4$.

In some embodiments, the disclosure provides to a method for potentiation of muscarinic acetylcholine receptor activity in a cell, comprising the step of contacting the cell with an effective amount of at least one disclosed compound or a pharmaceutically acceptable salt thereof. In some embodiments, the cell is mammalian (e.g., human). In some embodiments, the cell has been isolated from a mammal prior to the contacting step. In some embodiments, contacting is via administration to a mammal.

c. Enhancing Cognition

In some embodiments, the invention relates to a method for enhancing cognition in a mammal comprising the step of administering to the mammal an effective amount of least one disclosed compound; or a pharmaceutically acceptable salt, hydrate, solvate, or polymorph thereof.

In some embodiments, the disclosure provides a compound of formula (I), or a pharmaceutically acceptable salt thereof, for use in a method for the enhancement of cognition in a mammal. In some embodiments, the disclosure provides a pharmaceutical composition comprising a compound of formula (I), or a pharmaceutically acceptable salt thereof, for use in a method for the enhancement of cognition in a mammal.

In some embodiments, the disclosure provides a compound of formula (I), or a pharmaceutically acceptable salt thereof, for use in the manufacture of a medicament for the enhancement of cognition in a mammal.

In some embodiments, the mammal is a human. In some embodiments, the mammal has been diagnosed with a need for cognition enhancement prior to the administering step. In some embodiments, the method further comprises the step of identifying a mammal in need of cognition enhancement. In some embodiments, the need for cognition enhancement is associated with a muscarinic receptor dysfunction. In some embodiments, the muscarinic receptor is mAChR $M_4$.

In some embodiments, the cognition enhancement is a statistically significant increase in Novel Object Recognition. In some embodiments, the cognition enhancement is a statistically significant increase in performance of the Wisconsin Card Sorting Test.

d. Cotherapeutic Methods

The present invention is further directed to administration of a selective mAChR $M_4$ activator for improving treatment outcomes in the context of cognitive or behavioral therapy. That is, in some embodiments, the invention relates to a cotherapeutic method comprising a step of administering to a mammal an effective amount and dosage of at least one disclosed compound, or a pharmaceutically acceptable salt thereof.

In some embodiments, the disclosure provides a compound of formula (I), or a pharmaceutically acceptable salt thereof, for use in a cotherapeutic method with cognitive or behavioral therapy in a mammal. In some embodiments, the disclosure provides a pharmaceutical composition comprising a compound of formula (I), or a pharmaceutically acceptable salt thereof, for use in a cotherapeutic method with cognitive or behavioral therapy in a mammal.

In some embodiments, the disclosure provides a compound of formula (I), or a pharmaceutically acceptable salt thereof, for use in the manufacture of a medicament for a cotherapeutic method with cognitive or behavioral therapy in a mammal.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

e. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In some embodiments, the compound can be employed in combination with anti-Alzheimer's agents, beta-secretase inhibitors, cholinergic agents, gamma-secretase inhibitors, HMG-CoA reductase inhibitors, $M_1$ allosteric agonists, $M_1$ positive allosteric modulators, NSAIDs including ibuprofen, vitamin E, and anti-amyloid antibodies. In another embodiment, the subject compound can be employed in combination with sedatives, hypnotics, anxiolytics, antipsychotics (typical and atypical), antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carboclo-ral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound can be administered in conjunction with the use of physical methods such as with light therapy or electrical stimulation.

In some embodiments, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In some embodiments, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In some embodiments, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In some embodiments, the compounds can be coadministered with orthosteric muscarinic agonists, muscarinic potentiators, or cholinesterase inhibitors. In some embodiments, the compounds can be coadministered with GlyT1 inhibitors and the like such as, but not limited to: risperidone, clozapine, haloperidol, fluoxetine, prazepam, xanomeline, lithium, phenobarbital, and salts thereof and combinations thereof.

f. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire.™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. Kits

In one aspect, the disclosure provides kits comprising at least one disclosed compound or a pharmaceutically acceptable salt thereof, and one or more of:
(a) at least one agent known to increase mAChR $M_4$ activity;
(b) at least one agent known to decrease mAChR $M_4$ activity;
(c) at least one agent known to treat a disorder associated with cholinergic activity;
(d) instructions for treating a disorder associated with cholinergic activity;
(e) instructions for treating a disorder associated with $M_4$ receptor activity; or
(f) instructions for administering the compound in connection with cognitive or behavioral therapy.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

The disclosed kits can be employed in connection with disclosed methods of use.

The kits may further comprise information, instructions, or both that use of the kit may provide treatment for medical conditions in mammals (particularly humans). The information and instructions may be in the form of words, pictures, or both, and the like. In addition or in the alternative, the kit may include the compound, a composition, or both; and information, instructions, or both; regarding methods of application of compound, or of composition, for example with the benefit of treating or preventing medical conditions in mammals (e.g., humans).

The compounds and processes of the invention will be better understood by reference to the following examples, which are intended as an illustration of and not a limitation upon the scope of the invention.

6. Examples

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostated column compartment, C18 column, diode-array detector (DAD) and an Agilent 6150 MSD with the following parameters. The gradient conditions were 5% to 95% acetonitrile with the aqueous phase 0.1% TFA in water over 1.4 minutes, hold at 95% acetonitrile for 0.1 min, 0.5 mL/min, 55° C. ("90 sec method"). Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

a. Preparation of Intermediates

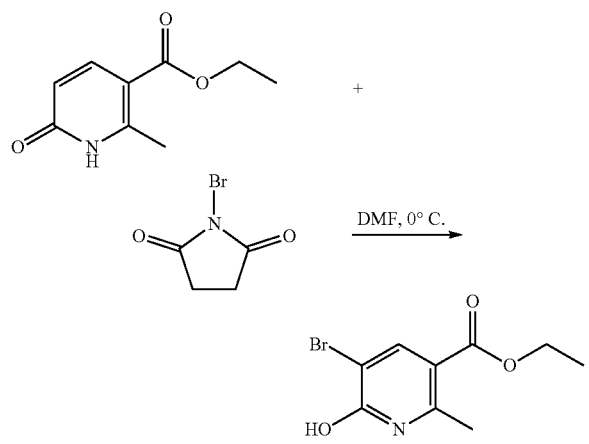

Ethyl 5-bromo-6-hydroxy-2-methylnicotinate. To a solution of ethyl-2-methyl-6-oxo-1,6-dihydropyridine-3-carboxylate (10 g, 55.2 mmol) in DMF (185 mL) at 0° C. was slowly added N-bromosuccinimide (10.8 g, 60.7 mmol) portionwise. The ice bath was removed. After 18 h, to the reaction was added saturated sodium bisulfite (aq) and stirred for 30 min. The reaction was filtered and the collected solid was dried by vacuum oven to afford the title compound (14.2 g). H NMR (400 MHz, DMSO) δ 8.15 (s, 1H), 4.20 (q, J=7.1 Hz, 2H), 3.32 (s, 3H), 2.55 (s, 1H), 1.27 (t, J=7.1 Hz, 3H); ES-MS [M+1]+: 260.0/262.0.

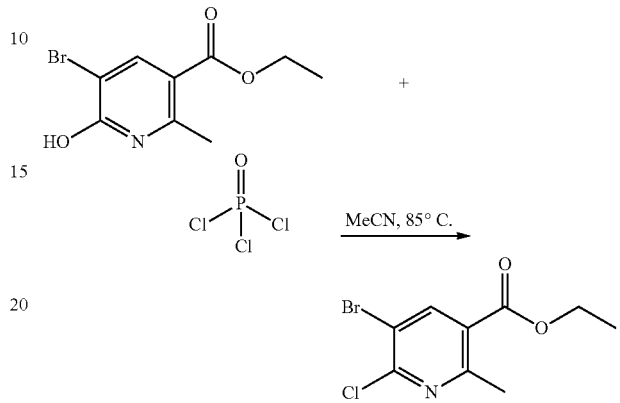

Ethyl 5-bromo-6-chloro-2-methylnicotinate. To a 500 mL round bottom flask was added ethyl 5-bromo-6-hydroxy-2-methylnicotinate (14.2 g, 54.6 mmol) in MeCN (300 mL) followed by phosphorous (V) oxychloride (29.4 mL, 316 mmol). The reaction was equipped with a condenser and heated at 85° C. After 18 h, the mixture was cooled to room temperature and concentrated. The residue was dissolved in DCM (10 mL) and slowly added dropwise to a stirred solution of saturated aqueous NaHCO$_3$ solution, keeping the pH>7. Additional DCM (25 mL) was added and the mixture was allowed to stir for 30 min. The organic layer was separated and the aqueous layer was re-extracted with 3:1 chloroform/IPA (3×20 mL). The combined organic layers were dried (MgSO$_4$), filtered, and concentrated. The crude residue was purified by normal-phase chromatography (0-25% EtOAc/Hexanes) to afford the title compound (12 g). $^1$H NMR (400 MHz, CDCl$_3$) δ 8.40 (s, 1H), 4.38 (q, J=7.1 Hz, 2H), 2.76 (s, 3H), 1.40 (t, J=7.1 Hz, 3H); ES-MS [M+1]+: 277.9/279.9.

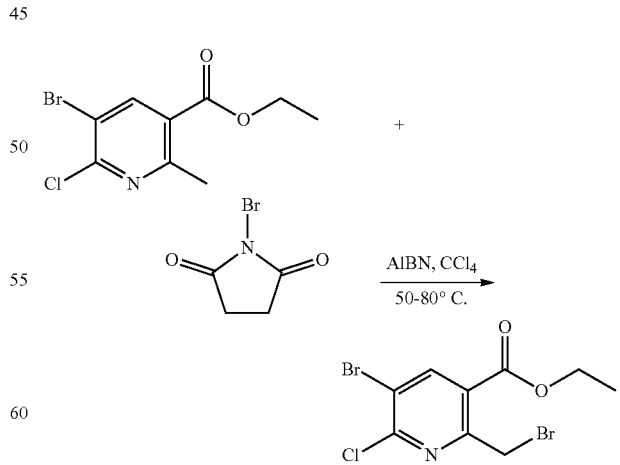

Ethyl 5-bromo-2-(bromomethyl)-6-chloronicotinate. To a solution of ethyl 5-bromo-6-chloro-2-methylnicotinate (12 g, 43.1 mmol) and 2,2'-azobis(2-methylpropionitrile) (0.71 g, 4.3 mmol) in carbon tetrachloride (287 mL) at 50° C. was added portionwise N-bromosuccinimide (8.43 g, 47.4 mmol). After 30 min, the reaction was heated to 80° C. After 18 h, the reaction was cooled to room temperature, diluted with water, and the organic layer was separated. The aqueous layer was extracted with DCM (3×50 mL). The combined organic layers were dried (MgSO$_4$), filtered, and concentrated. The crude residue was purified by normal-phase chromatography (04% EtOAc/Hexanes) to afford the title compound (13.6 g). $^1$H NMR (400 MHz, CDCl$_3$) δ 8.48 (s, 1H), 4.91 (s, 2H), 4.44 (q, J=7.1 Hz, 2H), 1.43 (t, J=7.1 Hz, 3H); ES-MS [M+1]$^+$: 357.9/359.9.

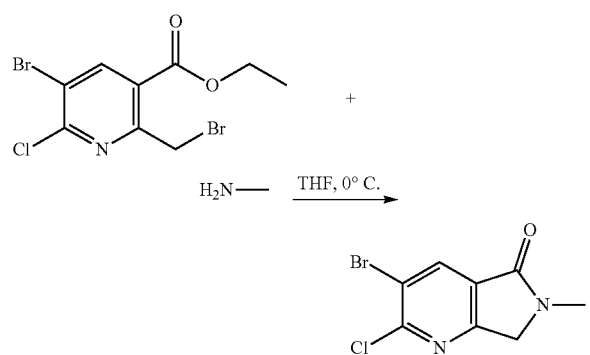

3-Bromo-2-chloro-6-methyl-6,7-dihydro-5H-pyrrolo[3,4-b]pyridin-5-one. To a solution of ethyl 5-bromo-2-(bromomethyl)-6-chloronicotinate (2.5 g, 6.99 mmol) in THF (140 mL) at 0° C. was added a 2.0 M solution of methylamine (17.5 mL, 35.0 mmol) and the reaction stirred for 30 min. The reaction was concentrated at rt and purified by normal-phase chromatography (0-30% EtOAc/DCM) to afford the title compound. $^1$H NMR (400 MHz, DMSO) δ 8.49 (s, 1H), 4.50 (s, 2H), 3.09 (s, 3H); ES-MS [M+1]$^+$: 261.1/263.1.

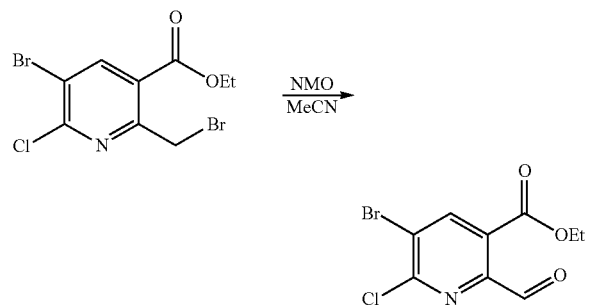

Ethyl 5-bromo-6-chloro-2-formylnicotinate. To a solution of ethyl 5-bromo-2-(bromomethyl)-6-chloronicotinate (1.36 g, 3.8 mmol) in MeCN (21.5 mL) was added 4-methylmorpholine N-oxide (893 μL, 8.6 mmol) and the mixture was stirred at ambient temperature for 2 hr. The solution was diluted with EtOAc and washed with water. The organic layer was separated, dried (MgSO$_4$), filtered, and concentrated. The crude product was purified via normal phase column chromatography (0-30% EtOAc/Hexanes) to give the title compound (668 mg). ES-MS [M+1]$^+$: 292/294; $^1$H NMR (400 MHz, CDCl$_3$) δ 10.22 (s, 1H), 8.34 (d, J=0.5 Hz, 1H), 4.45 (q, J=7.2 Hz, 2H), 1.41 (t, J=7.1 Hz, 3H).

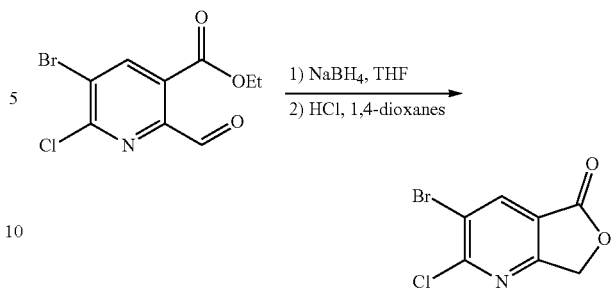

3-Bromo-2-chlorofuro[3,4-b]pyridin-5(7H)-one. To a solution of ethyl 5-bromo-6-chloro-2-formylnicotinate (668 mg, 1.76 mmol) in THF (8.8 mL) at −40° C. was added sodium borohydride (27 mg, 0.70 mmol). The reaction was allowed to stir at −40° C. for 45 minutes. To the reaction mixture was added water and the reaction was warmed to room temperature. After the reaction was extracted with EtOAc (3×), the combined organic layers were dried (MgSO$_4$), filtered, and concentrated. The residue was taken up in 1,4-dioxane (4 mL) then hydrochloric acid (879 μL, 3.52 mmol; 4 Min 1,4-dioxane) was added and the mixture was heated to 50° C. for 18 hr. Additional 4 M HCl in 1,4-dioxane (400 μL, 1.6 mmol) was added and the mixture was heated to 50° C. After 4 hr, the mixture was concentrated under vacuum and the residue was dissolved in DCM. The solution was washed with an aqueous saturated NaHCO$_3$ solution. The organic layer was separated, dried (MgSO$_4$), and concentrated. The crude residue was purified via normal phase column chromatography (0-0.5% MeOH/DCM) to give the title compound. ES-MS [M+1]$^+$: 248/250; $^1$H NMR (400 MHz, CDCl$_3$) δ 8.42 (t, J=0.5 Hz, 1H), 5.28 (d, J=0.5 Hz, 2H).

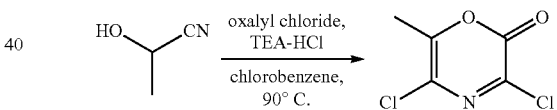

3,5-Dichloro-6-methyl-2H-1,4-oxazin-2-one. To a cooled solution of oxalyl chloride (49.1 mL, 563 mmol) in chlorobenzene (75 mL) under inert atmosphere at 0° C. was added dropwise a solution of DL-lactonitrile (10 g, 140.7 mmol) in chlorobenzene (11 mL). The solution was then heated to 90° C. where triethylamine hydrochloride (1.43 g, 10.4 mmol) was added in portions at 90° C. The resulting mixture was then stirred for 3 hours then cooled to ambient temperature and concentrated in vacuo. The resulting solution was then diluted with Et$_2$O (~300 mL) and solids were filtered out. The filtrate was concentrated and normal phase column chromatography on silica gel (0-15% EtOAc/Hex) afforded 16.8 g of title compound. $^1$H NMR (400 MHz, CDCl$_3$) δ 2.38 (s, 1H).

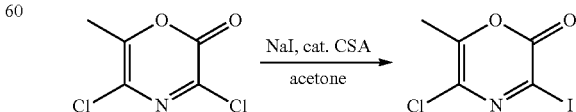

5-Chloro-3-iodo-6-methyl-2H-1,4-oxazin-2-one. To a solution of 3,5-dichloro-6-methyl-2H-1,4-oxazin-2-one (16.8 g, 93.4 mmol) in acetone (359 mL) was added sodium iodide (56.4 g, 374 mmol) and (1S,4R)-10-camphorsulfonic acid (1.52 g, 6.5 mmol) under inert atmosphere. The mixture was stirred at ambient temperature for 18 hours. The reaction mixture was concentrated then diluted with water and extracted with DCM (3×). After washing sequentially with an aqueous saturated solution of $Na_2S_2O_3$ and brine, the combined organics were dried ($MgSO_4$), filtered, and concentrated to afford 22 g of title compound. The material was carried forward without further purification. $^1$H NMR (400 MHz, $CDCl_3$) δ 2.30 (s, 3H); ES-MS $[M+1]^+$: 272.

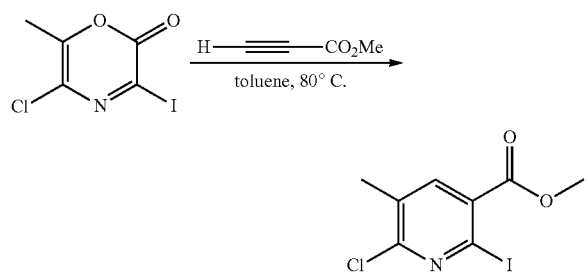

Methyl 6-chloro-2-iodo-5-methylnicotinate. A solution of 5-chloro-3-iodo-6-methyl-2H-1,4-oxazin-2-one (22 g, 81.1 mmol) and methyl propiolate (21.6 mL, 243 mmol) in toluene (80 mL) was heated to 80° C. for 42 h. The reaction was cooled to ambient temperature and the volatiles were removed under reduced pressure. Normal phase column chromatography on silica gel (0-10% EtOAc/hexanes, second to elute off column) gave 15.0 g of title compound. $^1$H NMR (400 MHz, $CDCl_3$) δ 7.86 (d, J=0.8 Hz, 1H), 3.95 (s, 3H), 2.36 (d, J=0.8 Hz, 3H); ES-MS $[M+1]^+$: 312.

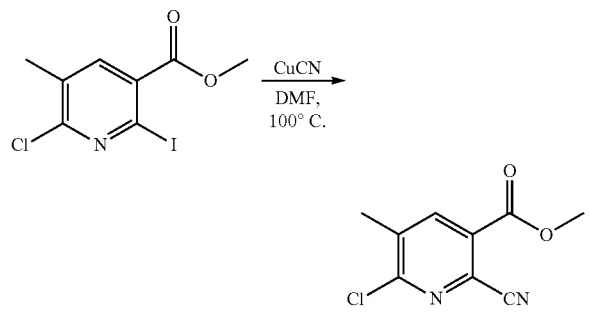

Methyl 6-chloro-2-cyano-5-methylnicotinate. A solution of methyl 6-chloro-2-iodo-5-methylnicotinate (15.0 g, 48.2 mmol) and copper(I) cyanide (6.48 g, 72.3 mmol) in DMF (112 mL) was heated at 100° C. for 1 hour. After cooling to ambient temperature, the mixture was filtered over Celite® washing with EtOAc. The filtrate was added to a saturated aqueous $NaHCO_3$ solution (~150 mL) and extracted with EtOAc (3×). The combined organics were then washed sequentially with an aqueous saturated solution of $NH_4Cl$ (100 mL) and brine. The organics were then dried ($MgSO_4$), filtered, and concentrated. Normal phase column chromatography on silica gel (0-40% EtOAc/hexanes) afforded 8.1 g of title compound. $^1$H NMR (400 MHz, $CDCl_3$) δ 8.26 (d, J=0.9 Hz, 1H), 4.04 (s, 3H), 2.52 (d, J=0.8 Hz, 3H); ES-MS $[M+1]^+$: 211.

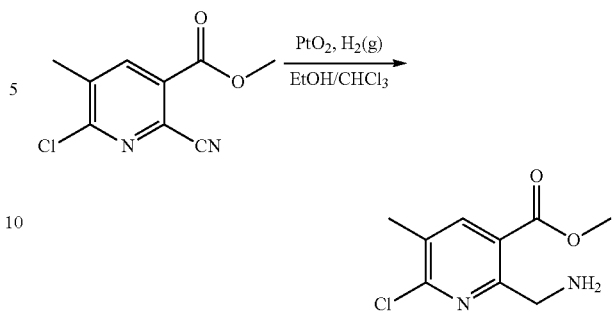

Methyl 2-(aminomethyl)-6-chloro-5-methylnicotinate. Platinum(IV) oxide (1.48 g, 6.5 mmol) was added to a round bottom flask under nitrogen. Next, a solution of methyl 6-chloro-2-cyano-5-methylnicotinate (8.1 g, 38.5 mmol) in ethanol/chloroform (240 mL; 3:1) was added. The flask was evacuated under vacuum and purged with $H_2$(g) (3×). The mixture was stirred under an atmosphere of hydrogen (balloon) for 36 hours. The solids were removed by filtration over Celite®, washing with DCM, and the filtrate was concentrated. The residue was dissolved in MeOH and purified by a SCX cartridge, eluting with MeOH solution to give the title compound. $^1$H NMR (400 MHz, MeOD) δ 8.38 (d, J=0.8 Hz, 1H), 4.62 (s, 2H), 3.96 (s, 3H), 2.47 (q, J=0.7 Hz, 3H); ES-MS $[M+H]^+$=215. The SCX cartridge was then flushed with $NH_3$/MeOH (7N) to give 3.4 g of an impure 2-chloro-3-methyl-6,7-dihydro-5H-pyrrolo[3,4-b]pyridin-5-one, which was purified using normal-phase column chromatography (3.5% MeOH/DCM/1% $NH_4$O H additive) (84.4 mg). $^1$H NMR (400 MHz, DMSO) δ 8.82 (s, 1H), 8.11 (d, J=0.9 Hz, 1H), 4.39 (s, 2H), 2.42 (d, J=0.8 Hz, 3H); ES-MS $[M+H]^+$=183.

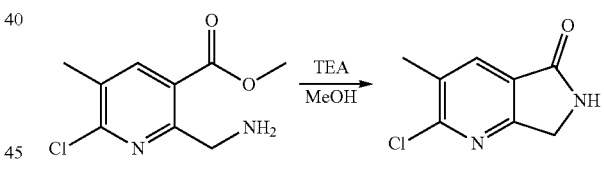

2-Chloro-3-methyl-6,7-dihydro-5H-pyrrolo[3,4-b]pyridin-5-one. To a vial was added a solution of methyl methyl 2-(aminomethyl)-6-chloro-5-methylnicotinate (5.46 g, 25.4 mmol) and triethylamine (17.7 mL, 127 mmol) in methanol (127 mL). The solution was allowed to stir at room temperature for 18 hours. The reaction mixture was concentrated in vacuo by half then the solids were removed by vacuum filtration, washing with MeOH to give 1.99 g of desired product. $^1$H NMR (400 MHz, DMSO) δ 8.82 (s, 1H), 8.11 (d, J=0.9 Hz, 1H), 4.39 (s, 2H), 2.42 (d, J=0.8 Hz, 3H); ES-MS $[M+1]^+$: 183.

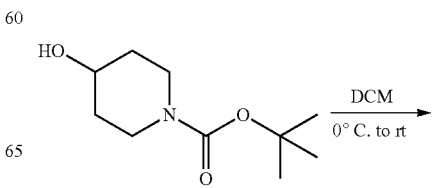

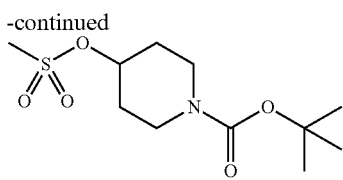

tert-Butyl 4-methylsulfonyloxypiperidine-1-carboxylate. To a solution of tert-butyl-4-hydroxypiperidine-1-carboxylate (2.5 g) in DCM (40 mL) at 0° C. was added triethylamine (2.42 mL) followed by dropwise addition of methanesulfonyl chloride (1.35 mL). The ice bath was removed and the reaction was stirred for 18 h at room temperature. The reaction mixture was diluted with 3:1 CHCl$_3$/IPA and water. The layers were separated and the aqueous layer was extracted with 3:1 CHCl$_3$/IPA (2×). The combined organic layers were washed with brine, dried over MgSO$_4$, filtered, and concentrated to afford the title compound (3.4 g). $^1$H NMR (400 MHz, CDCl$_3$) δ 4.91-4.85 (m, 1H), 3.73-3.67 (m, 2H), 3.33-3.26 (m, 2H), 3.03 (s, 3H), 1.99-1.93 (m, 2H), 1.85-1.77 (m, 2H), 1.45 (s, 9H).

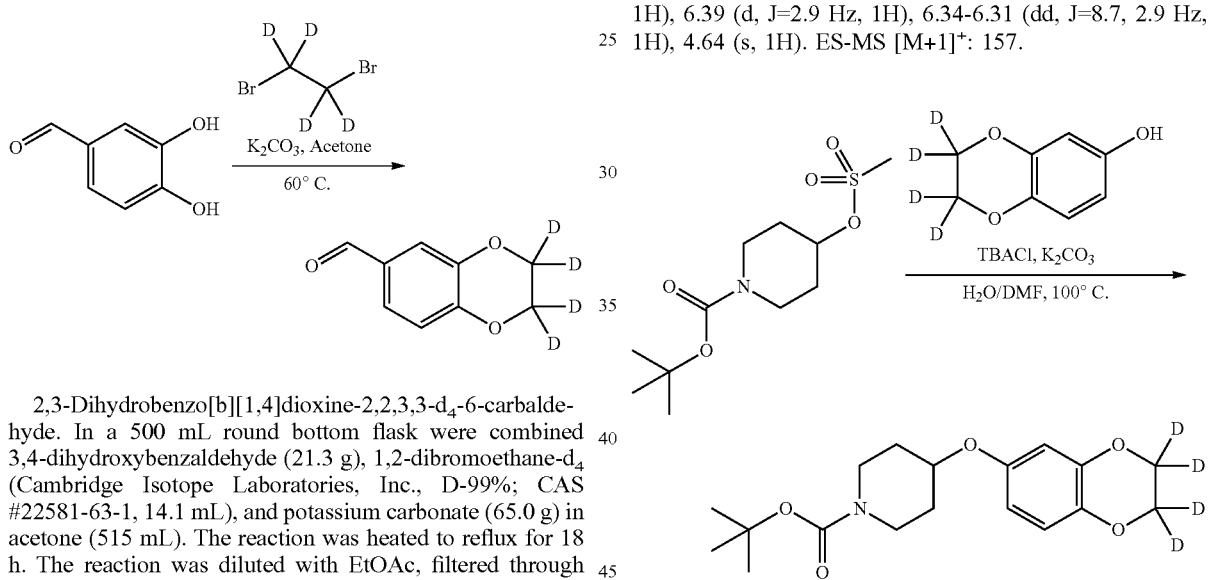

2,3-Dihydrobenzo[b][1,4]dioxine-2,2,3,3-d$_4$-6-carbaldehyde. In a 500 mL round bottom flask were combined 3,4-dihydroxybenzaldehyde (21.3 g), 1,2-dibromoethane-d$_4$ (Cambridge Isotope Laboratories, Inc., D-99%; CAS #22581-63-1, 14.1 mL), and potassium carbonate (65.0 g) in acetone (515 mL). The reaction was heated to reflux for 18 h. The reaction was diluted with EtOAc, filtered through Celite®, and the filtrate was concentrated in vacuo. The crude sample was purified by normal-phase column chromatography (0-40% EtOAc/hexanes) to afford the title compound (15.4 g). $^1$H NMR (400 MHz, CDCl$_3$) δ 9.82 (s, 1H), 7.41-7.38 (m, 2H), 6.97 (d, J=8.8 Hz, 1H). ES-MS [M+1]$^+$: 169.

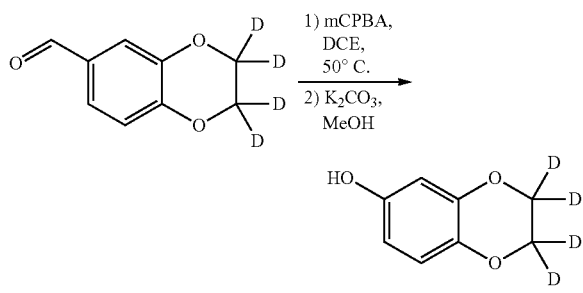

2,3-Dihydrobenzo[b][1,4]dioxin-2,2,3,3-d$_4$-6-ol. Step 1. To a solution of 2,3-dihydrobenzo[b][1,4]dioxine-2,2,3,3-d$_4$-6-carbaldehyde (15.4 g) in DCE (250 mL) was added 3-chloroperoxybenzoic acid (47.6 g, <77% CAS #937-14-4; Sigma-Aldrich). The reaction mixture was heated to 50° C. for 18 h. The reaction was diluted with DCM and saturated NaHCO$_3$ solution. The layers were separated. The aqueous layer was extracted with DCM (2×) and the combined organic layers were washed with brine, dried (MgSO$_4$), filtered, and concentrated to afford 2,3-dihydrobenzo[b][1,4]dioxin-6-yl-2,2,3,3-d$_4$ formate (15.1 g). ES-MS [M+1]$^+$: 185. Step 2. 2,3-Dihydrobenzo[b][1,4]dioxin-6-yl-2,2,3,3-d$_4$ formate (15.1 g) was dissolved in methanol (250 mL) and potassium carbonate (15.5 g) was added. After 3 h, the solvent was removed and water/DCM (1:1) were added. The aqueous layer was slowly acidified by dropwise addition of 6N aqueous HCl to pH<4. The layers were separated, the aqueous layer was extracted with DCM (2×) and the combined organic layers were washed with brine, dried (MgSO$_4$), filtered, and concentrated. The filtrate was purified by flash chromatography on silica gel (0-40% EtOAc/Hexanes). The desired fractions were concentrated and co-evaporated (2× with toluene) to afford the title compound (12.3 g). $^1$H NMR (400 MHz, CDCl$_3$) δ 6.72 (d, J=8.8 Hz, 1H), 6.39 (d, J=2.9 Hz, 1H), 6.34-6.31 (dd, J=8.7, 2.9 Hz, 1H), 4.64 (s, 1H). ES-MS [M+1]$^+$: 157.

tert-Butyl 4-((2,3-dihydrobenzo[b][1,4]dioxin-6-yl-2,2,3,3-d$_4$)oxy)piperidine-1-carboxylate. To a 1000 mL round bottom flask were added tert-butyl 4-methylsulfonyloxypiperidine-1-carboxylate (18 g), 2,3-dihydrobenzo[b][1,4]dioxin-2,2,3,3-d$_4$-6-ol (6.0 g), potassium carbonate (16.2 g), and tetrabutylammonium chloride (2.1 g) in water (360 mL) and DMF (18 mL). The reaction was heated to reflux. After 24 h, the reaction was cooled to room temperature, diluted with EtOAc and washed with water (3×), brine (2×). The organic layer was dried (MgSO$_4$), filtered, and concentrated in vacuo. The crude residue was purified by normal-phase column chromatography (0-40% EtOAc/Hexanes) to afford the title compound (3.1 g). $^1$H NMR (400 MHz, CDCl$_3$) δ 6.76 (d, J=8.7 Hz, 1H), 6.46 (d, J=2.8 Hz, 1H), 6.44-6.41 (dd, J=8.7, 2.8 Hz, 1H), 4.32-4.27 (m, 1H), 3.72-3.66 (m, 2H), 3.31-3.25 (m, 2H), 1.90-1.85 (m, 2H), 1.74-1.66 (m, 2H), 1.46 (s, 9H). ES-MS [M+1]$^+$: 340.

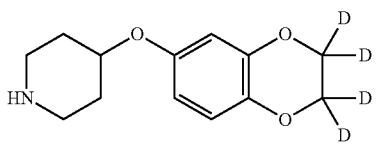 [SMILES: [2H]C1([2H])Oc2ccc(OC3CCNCC3)cc2OC1([2H])[2H]]

4-((2,3-Dihydrobenzo[b][1,4]dioxin-6-yl-2,2,3,3-d₄)oxy) piperidine. To a round bottom flask containing tert-butyl 4-((2,3-dihydrobenzo[b][1,4]dioxin-6-yl-2,2,3,3-d₄)oxy)piperidine-1-carboxylate (760 mg) in DCM (6 mL) was added trifluoroacetic acid (2 mL). After 2 h at room temperature, the solvents were removed and the crude residue was dissolved in DCM and concentrated in vacuo (3×) to afford the title compound (802 mg), as the TFA salt. ¹H NMR (400 MHz, CDCl₃) δ 6.78 (d, J=8.9 Hz, 1H), 6.45 (d, J=2.8 Hz, 1H), 6.43-6.40 (dd, J=8.8, 2.9 Hz, 1H), 4.51-4.50 (m, 1H), 3.44-3.37 (m, 2H), 3.28-3.25 (m, 2H), 2.16-2.07 (m, 4H). ES-MS [M+1]⁺: 240.

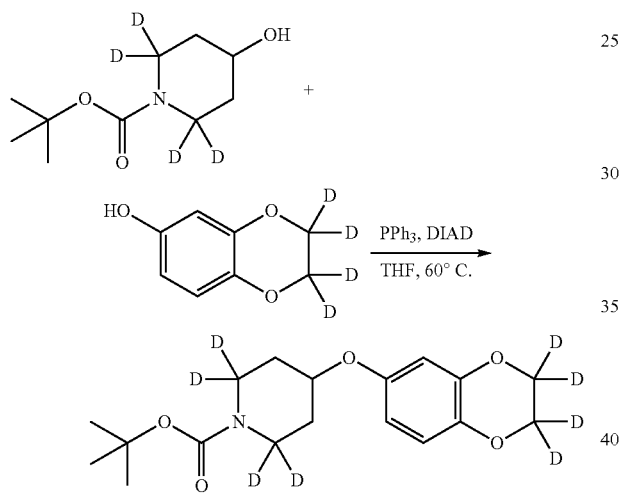

tert-Butyl 4-((2,3-dihydrobenzo[b][1,4]dioxin-6-yl-2,2,3,3-d₄)oxy)piperidine-1-carboxylate-2,2,6,6-d₄. In a vial were combined tert-butyl 4-hydroxypiperidine-1-carboxylate-2,2,6,6-d₄ (100 mg, 0.49 mmol)[Reference: J. of Labelled Compounds and Radiopharmaceuticals 2018, 61, 1036-1042], triphenylphosphine (180 mg, 0.68 mmol), and 2,3-dihydrobenzo[b][1,4]dioxin-2,2,3,3-d₄-6-ol (107 mg, 0.68 mmol) in THF (2 mL). The vessel was degassed followed by addition of diisopropyl azodicarboxylate (0.13 mL, 0.68 mmol). The reaction was heated at 60° C. for 18 h. The reaction was dissolved in 3:1 CHCl₃:IPA and concentrated with Celite®. The solid was dry loaded for purification on silica gel using normal-phase column chromatography (0-25% EtOAc/Hexanes). The desired fractions were concentrated to afford the title compound (123 mg). ¹H NMR (400 MHz, CDCl₃) δ 6.75 (d, J=8.7 Hz, 1H), 6.45 (d, J=2.8 Hz, 1H), 6.42 (dd, J=8.8, 2.9 Hz, 1H), 4.31-4.26 (m, 1H), 1.87-1.83 (m, 2H), 1.71-1.66 (m, 2H), 1.45 (s, 9H). ES-MS [M+1]⁺: 344.

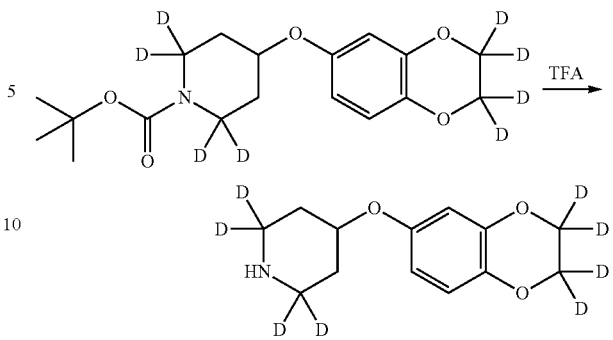

4-((2,3-Dihydrobenzo[b][1,4]dioxin-6-yl-2,2,3,3-d₄)oxy) piperidine-2,2,6,6-d₄. In a vial were combined tert-butyl 4-((2,3-dihydrobenzo[b][1,4]dioxin-6-yl-2,2,3,3-d₄)oxy)piperidine-1-carboxylate-2,2,6,6-d₄ (123 mg, 0.36 mmol) and trifluoroacetic acid (0.5 mL) in dichloromethane (2 mL). The reaction stirred for 1 h and was concentrated. The residue was purified by SCX Cartridge (5G), washed with MeOH, and eluted with 7N NH₃/MeOH solution. The solvents were removed to afford the title compound (55 mg). ¹H NMR (400 MHz, CDCl₃) δ 6.75 (d, J=8.8 Hz, 1H), 6.46 (d, J=2.8 Hz, 1H), 6.43 (dd, J=8.8, 2.8 Hz, 1H), 4.24-4.18 (m, 1H), 1.99 (d, J=3.8 Hz, 1H), 1.96 (d, J=3.7 Hz, 1H), 1.63 (d, J=8.4 Hz, 1H) 1.60 (d, J=8.6 Hz, 1H). ES-MS [M+1]⁺: 244.

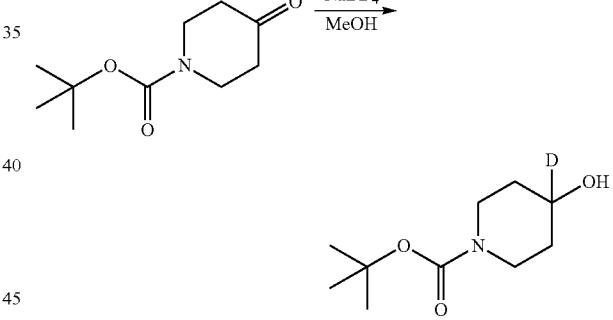

tert-Butyl 4-hydroxypiperidine-1-carboxylate-4-d. To a 0° C. solution of 1-tert-butyl-4-piperidone (10 g, 50 mmol) in methanol (250 mL) was added sodium borodeuteride (3.2 mL, 100 mmol). The resulting mixture was stirred for 4 h at room temperature. The reaction was quenched with saturated NH₄Cl (aq) and extracted with EtOAc (3×). The combined organic layers were dried (MgSO₄), filtered, and concentrated to afford the title compound (10 g). ¹H NMR (400 MHz, CDCl₃) δ 3.85 (d, J=12.4 Hz, 2H), 3.06-3.00 (m, 2H), 1.87-1.82 (m, 2H), 1.48-1.42 (m, 2H), 1.46 (s, 9H).

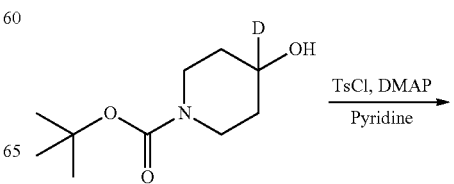

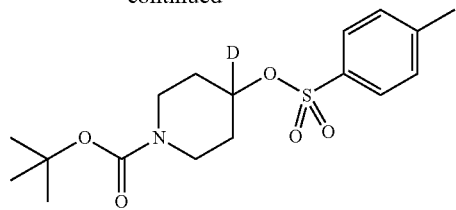

tert-Butyl 4-(tosyloxy)piperidine-1-carboxylate-4-d. To a suspension of tert-butyl 4-hydroxypiperidine-1-carboxylate-4-d (10 g) and 4-dimethyl-aminopyridine (0.6 g) in pyridine (45 mL) was added tosyl chloride (11.8 g). The mixture stirred at room temperature for 18 h. The reaction was quenched with saturated NaHCO₃ solution and extracted with EtOAc (2×). The combined organic layers were washed with water (2×), brine (2×), dried (MgSO₄), filtered, and concentrated. The crude oil was purified by normal phase column chromatography (0-20% EtOAc/hexanes). After removal of solvent, the desired compound was obtained (14.3 g). $^1$H NMR (400 MHz, CDCl₃) δ 7.79 (d, J=8.4 Hz, 2H), 7.34 (d, J=8.0 Hz, 2H), 3.61-3.55 (m, 2H), 3.28-3.22 (m, 2H), 2.45 (s, 3H), 1.79-1.73 (m, 2H), 1.70-1.64 (m, 2H), 1.43 (s, 9H). ES-MS [M+Na]⁺: 379.

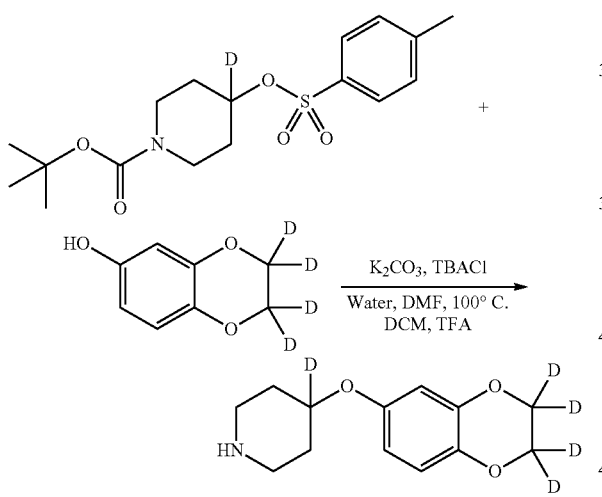

4-((2,3-Dihydrobenzo[b][1,4]dioxin-6-yl-2,2,3,3-d₄)oxy)piperidine-4-d. To a round bottom flask were added 2,3-dihydrobenzo[b][1,4]dioxin-2,2,3,3-d₄-6-ol (1.0 g, 6.7 mmol), tert-butyl 4-(tosyloxy)piperidine-1-carboxylate-4-d (2.0 g, 5.6 mmol), potassium carbonate (2.4 g, 16.8 mmol), and tetrabutylammonium chloride (0.31 g, 1.1 mmol) in water (25 mL) and DMF (1.3 mL). The reaction was heated at reflux for 18 h. The reaction was diluted with 3:1 CHCl₃/IPA and the layers were separated. The aqueous layer was extracted with 3:1 CHCl₃/IPA (2×) and the combined organic layers were washed with water, brine, then dried (MgSO₄), filtered, and concentrated. The crude residue was purified by normal-phase column chromatography (0-20% EtOAc/hexanes). After the removal of solvent, the residue was dissolved in DCM (9 mL) followed by addition of trifluoroacetic acid (2.1 mL). After 1 h, the solvents were removed in vacuo. The residue was dissolved in MeOH and loaded onto SCX Cartridge. The cartridge was rinsed with MeOH and 7N NH₃/MeOH solution. The solvents were removed to afford the title compound (725 mg). $^1$H NMR (400 MHz, CDCl₃) δ 6.75 (d, J=8.7, 1H), 6.45 (d, J=2.8, 1H), 6.41 (dd, J=8.8, 2.9 Hz, 1H), 3.21-3.15 (m, 2H), 2.87-2.81 (m, 2H), 2.07-2.00 (m, 2H), 1.78-1.72 (m, 2H). ES-MS [M+1]⁺: 241.

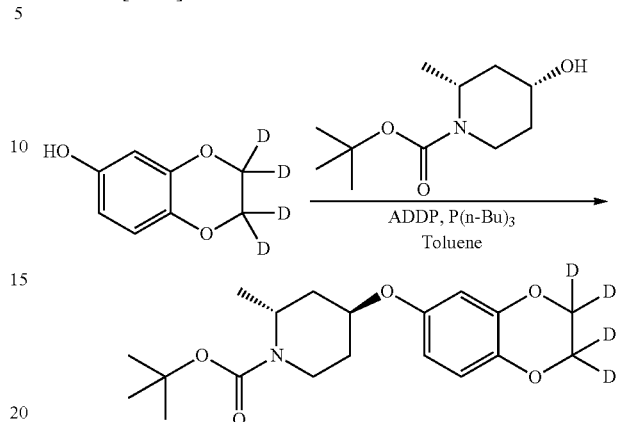

tert-Butyl (2R,4S)-4-((2,3-Dihydrobenzo[b][1,4]dioxin-6-yl-2,2,3,3-d₄)oxy)-2-methylpiperidine-1-carboxylate. To a mixture of 2,3-dihydrobenzo[b][1,4]dioxin-2,2,3,3-d₄-6-ol (8.4 g), (2R,4R)-tert-butyl 4-hydroxy-2-methylpiperidine-1-carboxylate (9.5 g) and P(n-Bu)₃ (13.5 mL) in toluene (300 mL) was added ADDP (13.6 g) portionwise. The reaction mixture was heated to 90° C. After 18 hours, the reaction was concentrated in vacuo and the residue was dissolved in CHCl₃:IPA (3:1) and saturated NaHCO₃ (aq) solution. The layers were separated and the aqueous layer was extracted with CHCl₃:IPA (3×). The combined organic layers were dried (MgSO₄), filtered and concentrated. The residue was purified by normal phase column chromatography (0-30%, ethyl acetate in petroleum ether) to give the title compound. $^1$H NMR (400 MHz, CDCl₃) δ 6.77 (d, J=8.8 Hz, 1H), 6.46 (s, 1H), 6.42 (dd, J=8.8 Hz, 1.6 Hz, 1H), 4.61-4.46 (m, 1H), 4.41-4.31 (m, 1H), 4.13-4.06 (m, 1H), 2.96-2.89 (m, 1H), 2.14-2.04 (m, 1H), 2.01-1.90 (m, 1H), 1.74-1.64 (m, 1H), 1.52-1.42 (s, 10H), 1.19 (d, J=7.2 Hz, 3H).

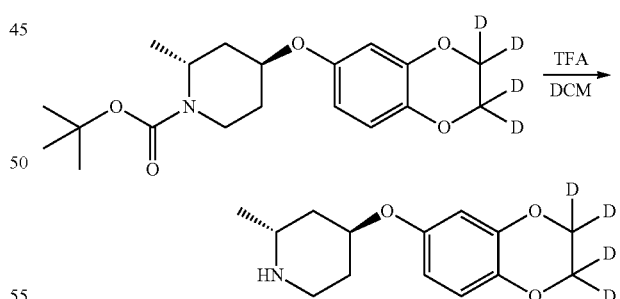

(2R,4S)-4-((2,3-Dihydrobenzo[b][1,4]dioxin-6-yl-2,2,3,3-d₄)oxy)-2-methylpiperidine. To a solution of tert-butyl (2R,4S)-4-((2,3-dihydrobenzo[b][1,4]dioxin-6-yl-2,2,3,3-d₄)oxy)-2-methylpiperidine-1-carboxylate (3.7 g) in DCM (20 mL) was added TFA (4 mL) and the reaction was stirred at 20° C. for 3 hours. The reaction was quenched with sat. aq. Na₂CO₃ to pH 8-9 at 0° C. and extracted with DCM (20 mL×2). The combined organic layers were washed with brine (20 mL), dried over Na₂SO₄ and concentrated to give the title compound (2.6 g, crude). ES-MS [M+1]⁺: 254.2.

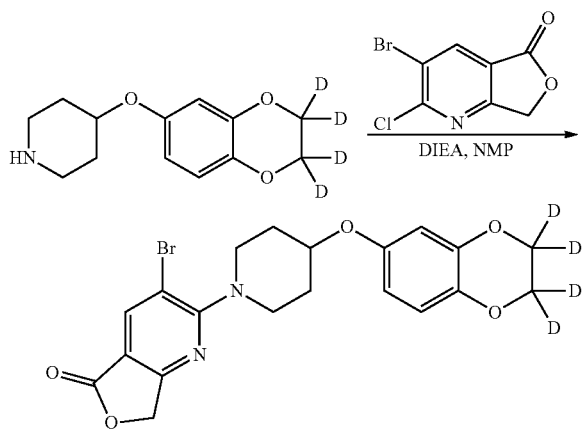

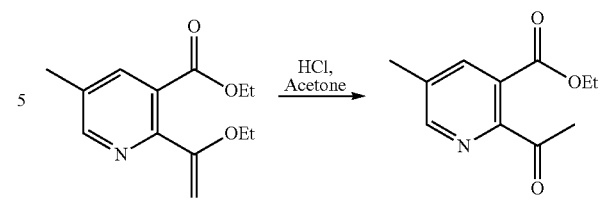

3-Bromo-2-(4-((2,3-dihydrobenzo[b][1,4]dioxin-6-yl-2,2,3,3-d₄)oxy)piperidin-1-yl)furo[3,4-b]pyridin-5(7H)-one. To a solution of 4-((2,3-dihydrobenzo[b][1,4]dioxin-6-yl-2,2,3,3-d₄)oxy)piperidine (170 mg, 0.36 mmol) in DMSO (5.6 mL) was added 3-bromo-2-chlorofuro[3,4-b]pyridin-5(7H)-one (80 mg, 0.30 mmol) and N,N-diisopropylethylamine (155 μL, 0.89 mmol). The mixture was stirred at ambient temperature for 18 h. The mixture was added to water and extracted with EtOAc (3×). The combined organics were dried (MgSO₄), filtered, and concentrated. The crude residue was purified via normal phase column chromatography (0-30% EtOAc/DCM) to give the title compound (131 mg). ES-MS [M+1]⁺: 451/453; ¹H NMR (400 MHz, CDCl₃) δ 8.16 (s, 1H), 6.78 (d, J=8.8 Hz, 1H), 6.50 (d, J=2.8 Hz, 1H), 6.46 (dd, J=8.7, 2.9 Hz, 1H), 5.11 (s, 2H), 4.43 (tt, J=7.0, 3.6 Hz, 1H), 3.81 (ddd, J=12.2, 8.0, 3.4 Hz, 2H), 3.51 (ddd, J=13.2, 7.4, 3.5 Hz, 2H), 2.08 (ddq, J=10.6, 6.6, 3.3 Hz, 2H), 1.96 (dtd, J=13.7, 7.1, 3.5 Hz, 2H).

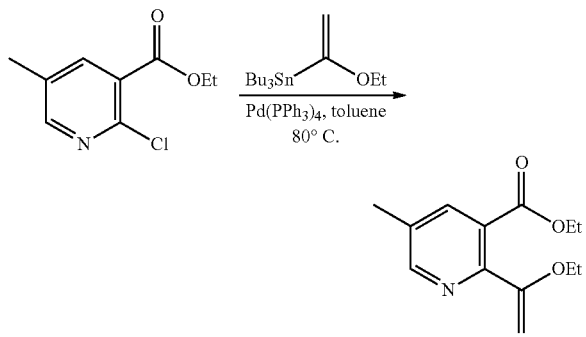

Ethyl 2-(1-ethoxyvinyl)-5-methylnicotinate. To a solution of ethyl 2-chloro-5-methylnicotinate (500 mg, 2.5 mmol) and tetrakis(triphenylphosphine)palladium(0) (159 mg, 0.14 mmol) in toluene (8.7 mL) under nitrogen atmosphere was added tributyl(1-ethoxyvinyl)tin (1.39 mL, 4.12 mmol). The mixture was heated to 80° C. for 18 h. After cooling to ambient temperature, the crude product was purified via normal phase column chromatography (0-50% EtOAc/Hexanes) to give the title compound (342 mg). ES-MS [M+1]⁺: 235; ¹H NMR (400 MHz, CDCl₃) δ 8.46 (dd, J=2.2, 0.8 Hz, 1H), 7.69 (dd, J=2.2, 0.8 Hz, 1H), 4.88 (d, J=2.4 Hz, 1H), 4.39 (d, J=2.4 Hz, 1H), 4.33 (q, J=7.1 Hz, 2H), 3.90 (q, J=7.0 Hz, 2H), 2.37 (t, J=0.7 Hz, 3H), 1.36 (t, J=7.2 Hz, 3H), 1.34 (t, J=7.0 Hz, 3H).

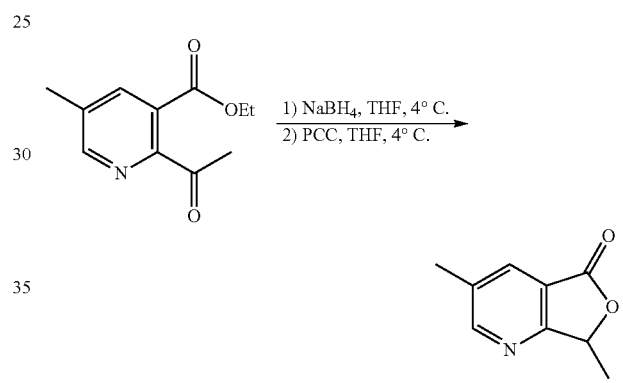

Ethyl 2-acetyl-5-methylnicotinate. To a mixture of ethyl 2-(1-ethoxyvinyl)-5-methylnicotinate (342 mg, 1.45) in acetone (6.5 mL) was added 2 M hydrochloric acid in water (8.0 mL, 16.1 mmol) and the mixture was stirred for 18 h at ambient temperature. Solvents were removed in vacuo. The residue was dissolved in EtOAc and washed with saturated aqueous NaHCO₃. The organics were isolated and the aqueous layer was further extracted with EtOAc (3×). The organics were pooled, dried (MgSO₄), filtered and concentrated. The material was carried forward without further purification. ES-MS [M+1]⁺: 208; ¹H NMR (400 MHz, CDCl₃) δ 8.52 (dd, J=2.1, 0.8 Hz, 1H), 7.75 (dq, J=1.5, 0.7 Hz, 1H), 4.39 (q, J=7.2 Hz, 2H), 2.68 (s, 3H), 2.43 (t, J=0.7 Hz, 3H), 1.37 (t, J=7.2 Hz, 3H).

3,7-Dimethylfuro[3,4-b]pyridin-5(7H)-one. To a solution of ethyl 2-acetyl-5-methylnicotinate (253 mg, 1.22 mmol) in THF (30 mL) at 4° C. was added sodium borohydride (46 mg, 1.22 mmol). The mixture was stirred at 4° C. for 16 h. Water (20 mL) was added and the mixture was extracted with EtOAc (3×). The combined organics were dried (MgSO₄), filtered, and concentrated. Next, the residue was dissolved in DCM (10 mL) and cooled to 4° C. where pyridinium chlorochromate (612 mg, 2.81 mmol) was added. The mixture was stirred at 4° C. for 16 h. The reaction mixture was filtered through a pad of Celite® and concentrated. The crude product was purified via normal phase column chromatography (0-20% EtOAc/DCM) to give the title compound (114 mg). ES-MS [M+1]⁺: 164; ¹H NMR (400 MHz, CDCl₃) δ 8.68 (dd, J=1.9, 0.8 Hz, 1H), 7.97 (dd, J=2.2, 1.0 Hz, 1H), 5.52 (q, J=6.8 Hz, 1H), 2.48 (q, J=0.7 Hz, 3H), 1.69 (d, J=6.8 Hz, 3H).

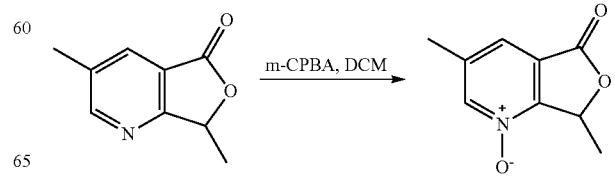

3,7-Dimethyl-5-oxo-5,7-dihydrofuro[3,4-b]pyridine 1-oxide. To a solution of 3,7-dimethylfuro[3,4-b]pyridin-5(7H)-one (84.7 mg, 0.52 mmol) in DCM (2.6 mL) at 0° C. was slowly added 3-chloroperoxybenzoic acid (108 mg, 0.62 mmol) and the reaction was allowed to stir at ambient temperature for 18 h. A saturated aqueous Na$_2$S$_2$O$_3$ solution was then added and the mixture was stirred 1 hr. The organic layer was isolated and the aqueous layer was further extracted with DCM (3×) then with chloroform/IPA (3:1) (2×). The organics were pooled, washed with 1 M NaOH, then passed through a phase separator, and concentrated to give the title compound (46 mg). The material was carried forward without further purification. ES-MS [M+1]$^+$: 180; $^1$H NMR (400 MHz, CDCl$_3$) δ 8.23 (t, J=1.0 Hz, 1H), 7.55 (s, 1H), 5.68 (q, J=6.7 Hz, 1H), 2.45 (d, J=0.9 Hz, 3H), 1.83 (d, J=6.7 Hz, 3H).

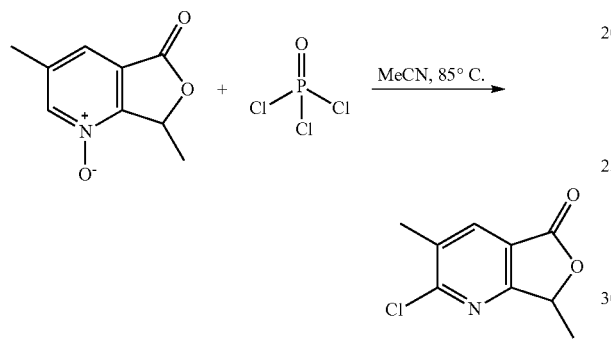

2-Chloro-3,7-dimethylfuro[3,4-b]pyridin-5(7H)-one. To a vial was added 3,7-dimethyl-5-oxo-5,7-dihydrofuro[3,4-b]pyridine 1-oxide (42 mg, 0.24 mmol) in MeCN (1.2 mL) followed by phosphorus(V) oxychloride (110 µL, 1.18 mmol). The vial was sealed and the mixture was heated to 85° C. for 1 h. The mixture was cooled to ambient temperature and slowly added to a stirred solution of saturated aqueous NaHCO$_3$, keeping the pH alkaline. DCM was added and the mixture was allowed to stir for 30 minutes. The organic layer was isolated and the aqueous layer was back extracted with chloroform/IPA (3:1) (3×). The combined organic layers were passed through a phase separator and concentrated. The residue was carried forward without further purification. ES-MS [M+1]$^+$: 198.

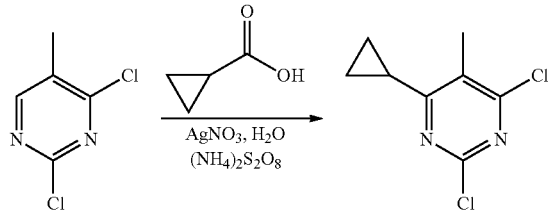

2,4-Dichloro-6-cyclopropyl-5-methylpyrimidine. A solution of 2,4-dichloro-5-methylpyrimidine (1.0 g, 6.1 mmol), silver nitrate (521 mg, 3.1 mmol) and cyclopropanecarboxylic acid (1.47 mL, 18.4 mmol) in water (31 mL) was heated to 72° C. Ammonium persulfate (2.1 g, 9.2 mmol) was added portion wise over 15 minutes. After heating an additional 20 minutes at 72° C., sulfuric acid (491 µL, 9.2 mmol) was added and the mixture was heated to 90° C. for 1 h. After cooling to ambient temperature, the reaction mixture was slowly poured into a solution of saturated aqueous bicarbonate and DCM and stirred for an additional 20 minutes. The organic layer was isolated and the aqueous layer was further extracted with DCM (3×). The combined organic layers were dried (MgSO$_4$), filtered, and concentrated. Purification via normal phase column chromatography (0-25% EtOAc/Hexanes) afforded the title compound (872 mg). ES-MS [M+1]+: 203/205; $^1$H NMR (400 MHz, CDCl$_3$) δ 2.45 (s, 3H), 2.11 (tt, J=7.9, 4.6 Hz, 1H), 1.29-1.23 (m, 2H), 1.18-1.12 (m, 2H).

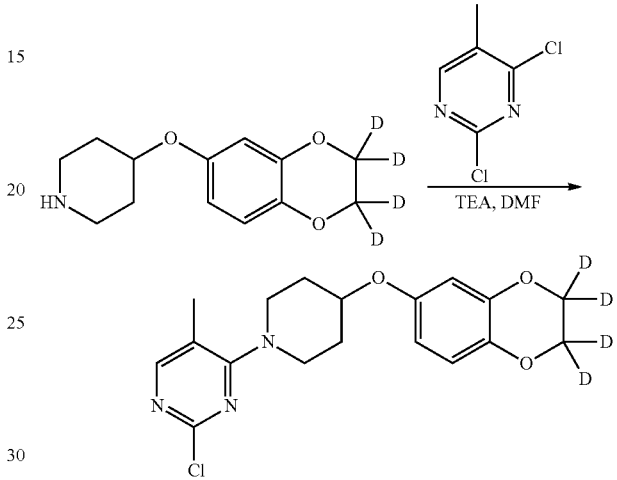

2-Chloro-4-(4-((2,3-dihydrobenzo[b][1,4]dioxin-6-yl-2,2,3,3-d$_4$)oxy)piperidin-1-yl)-5-methylpyrimidine. To a solution of 4-((2,3-dihydrobenzo[b][1,4]dioxin-6-yl-2,2,3,3-d$_4$)oxy)piperidine (50 mg, 0.21 mmol) in DMF (1 mL) was added triethylamine (146 µL, 1.04 mmol) and 2,4-dichloro-5-methylpyrimidine (37.5 mg, 0.23 mmol). The mixture was stirred at ambient temperature for 18 h. The mixture was added to water (20 mL) and extracted with EtOAc (3×). The organics were pooled, dried (MgSO$_4$), filtered and concentrated. The crude material was purified by normal-phase column chromatography (0-30% EtOAc/DCM) to afford the title compound (26 mg). $^1$H NMR (400 MHz, CDCl$_3$) δ 7.94 (q, J=0.8 Hz, 1H), 6.78 (d, J=8.7 Hz, 1H), 6.49 (d, J=2.8 Hz, 1H), 6.45 (dd, J=8.7, 2.9 Hz, 1H), 4.41 (tt, J=6.9, 3.6 Hz, 1H), 3.77 (ddd, J=12.2, 7.9, 3.5 Hz, 2H), 3.46 (ddd, J=13.4, 7.5, 3.6 Hz, 2H), 2.20 (d, J=0.8 Hz, 3H), 2.02 (ddd, J=16.3, 7.5, 3.8 Hz, 2H), 1.88 (dtd, J=13.8, 7.1, 3.5 Hz, 2H). ES-MS [M+1]$^+$: 366.

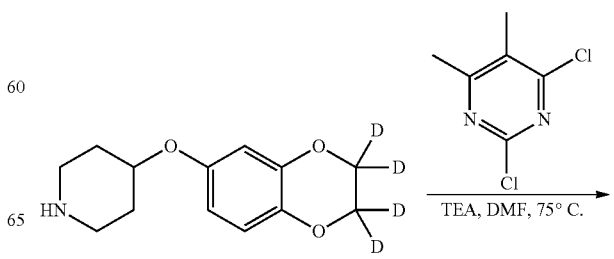

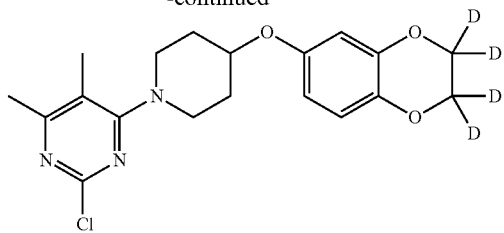

2-Chloro-4-(4-((2,3-dihydrobenzo[b][1,4]dioxin-6-yl-2,2,3,3-d₄)oxy)piperidin-1-yl)-5,6-dimethylpyrimidine. To a solution of 4-((2,3-dihydrobenzo[b][1,4]dioxin-6-yl-2,2,3,3-d₄)oxy)piperidine (50 mg, 0.21 mmol) in DMF (1 mL) was added triethylamine (146 μL, 1.04 mmol) and 2,4-dichloro-5,6-dimethylpyrimidine (41 mg, 0.23 mmol). The mixture was stirred at 75° C. for 18 h. The mixture was added to water (20 mL) and extracted with EtOAc (3×). The collected organic layers were dried (Na₂SO₄), filtered and concentrated. The crude material was purified by normal-phase column chromatography on silica gel (0-30% EtOAc/DCM) to afford the title compound (54 mg). $^1$H NMR (400 MHz, CDCl₃) δ 6.78 (d, J=8.7 Hz, 1H), 6.49 (d, J=2.8 Hz, 1H), 6.45 (dd, J=8.7, 2.8 Hz, 1H), 4.37 (tt, J=7.2, 3.7 Hz, 1H), 3.62 (ddd, J=11.9, 7.6, 3.6 Hz, 2H), 3.25 (ddd, J=12.6, 7.9, 3.5 Hz, 2H), 2.38 (s, 3H), 2.12 (s, 3H), 2.10-1.97 (m, 2H), 1.87 (ddt, J=17.1, 7.4, 3.5 Hz, 2H). ES-MS [M+1]⁺: 380.

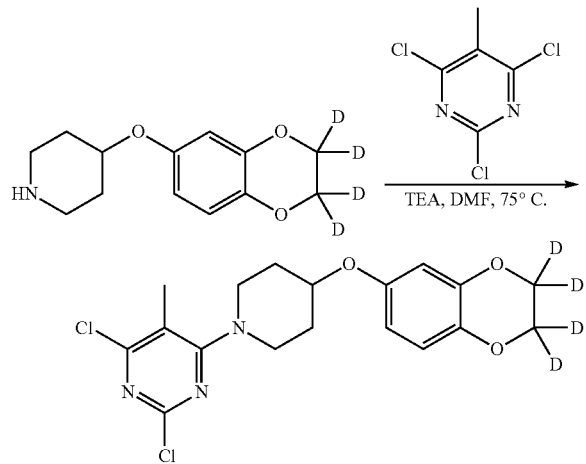

2,4-Dichloro-6-(4-((2,3-dihydrobenzo[b][1,4]dioxin-6-yl-2,2,3,3-d₄)oxy)piperidin-1-yl)-5-methylpyrimidine. To a solution of 4-((2,3-dihydrobenzo[b][1,4]dioxin-6-yl-2,2,3,3-d₄)oxy)piperidine (121 mg, 0.50 mmol) in DMF (1.5 mL) was added triethylamine (352 μL, 0.35 mmol) and 2,4,6-trichloro-5-methylpyrimidine (110 mg, 0.56 mmol). The mixture was stirred at 70° C. for 18 h. The mixture was added to water (20 mL) and extracted with EtOAc (3×). The collected organic layers were dried (MgSO₄), filtered, and concentrated. The crude residue was purified by normal-phase column chromatography (0-80% EtOAc/DCM) to afford the title compound (173 mg). $^1$H NMR (400 MHz, CDCl₃) δ 6.78 (d, J=8.7 Hz, 1H), 6.48 (d, J=2.8 Hz, 1H), 6.44 (dd, J=8.8, 2.8 Hz, 1H), 4.41 (tt, J=7.0, 3.6 Hz, 1H), 3.69 (ddd, J=12.3, 8.1, 3.5 Hz, 2H), 3.40 (ddd, J=13.4, 7.2, 3.7 Hz, 2H), 2.23 (s, 3H), 2.08-1.96 (m, 2H), 1.89 (dtd, J=13.6, 6.9, 3.5 Hz, 2H). ES-MS [M+1]⁺: 400.2/402.2.

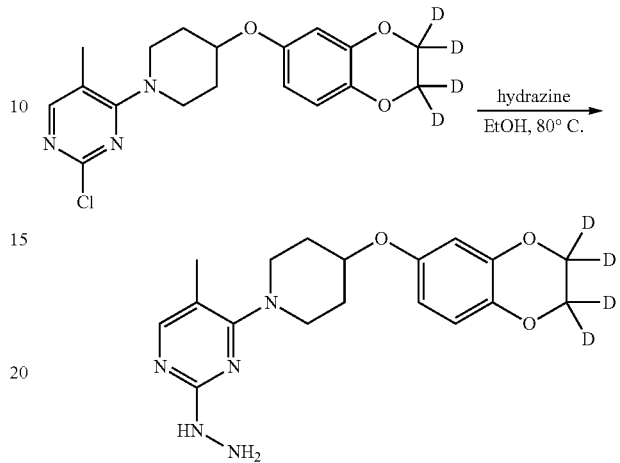

4-(4-((2,3-Dihydrobenzo[b][1,4]dioxin-6-yl-2,2,3,3-d₄)oxy)piperidin-1-yl)-2-hydrazineyl-5-methylpyrimidine. To a solution of hydrazine (46 μL, 1.45 mmol) in ethanol (483 μL) was added 2-chloro-4-(4-((2,3-dihydrobenzo[b][1,4]dioxin-6-yl-2,2,3,3-d₄)oxy)piperidin-1-yl)-5-methylpyrimidine (27 mg, 0.07 mmol) and the mixture was stirred at 80° C. for 4 h. The mixture was cooled to ambient temperature and an additional 30 μL of hydrazine was added and the mixture was stirred an additional 3 h at 80° C. After cooling to ambient temperature, the mixture was concentrated and carried forward without further purification. ES-MS [M+1]⁺: 362.

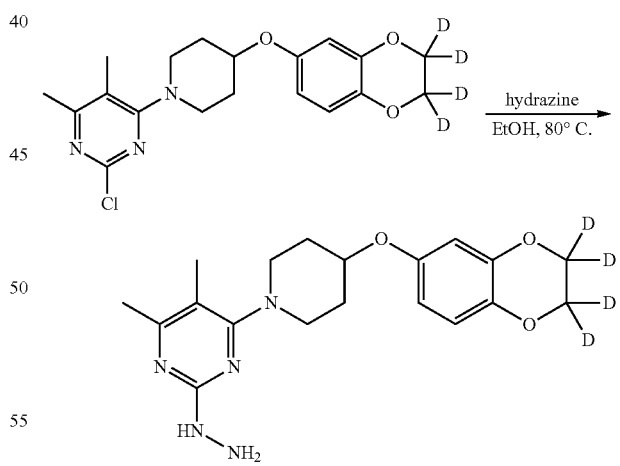

4-(4-((2,3-Dihydrobenzo[b][1,4]dioxin-6-yl-2,2,3,3-d₄)oxy)piperidin-1-yl)-2-hydrazineyl-5-methylpyrimidine. To a solution of 2-chloro-4-(4-((2,3-dihydrobenzo[b][1,4]dioxin-6-yl-2,2,3,3-d₄)oxy)piperidin-1-yl)-5,6-dimethylpyrimidine (54 mg, 0.14 mmol) in ethanol (950 μL) was added hydrazine (89 μL, 2.83 mmol) and the mixture was stirred at 80° C. for 9 h. After cooling to ambient temperature, the mixture was concentrated and carried forward without further purification. ES-MS [M+1]⁺: 376.

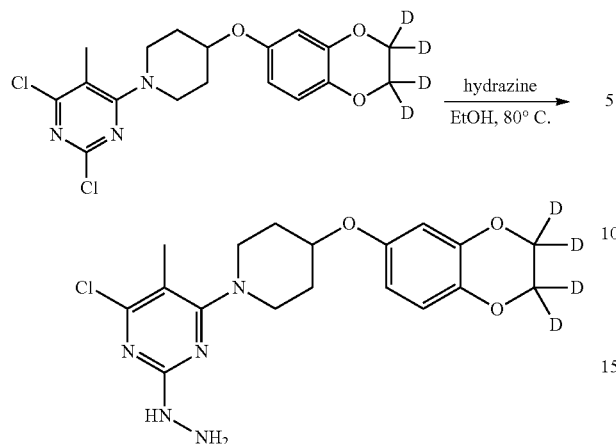

4-Chloro-6-(4-((2,3-dihydrobenzo[b][1,4]dioxin-6-yl-2,2,3,3-d₄)oxy)piperidin-1-yl)-2-hydrazineyl-5-methylpyrimidine. To a solution of hydrazine (271 μL, 8.64 mmol) in ethanol (3.0 mL) was added 2,4-dichloro-6-(4-((2,3-dihydrobenzo[b][1,4]dioxin-6-yl-2,2,3,3-d₄)oxy)piperidin-1-yl)-5-methylpyrimidine (173 mg, 0.43 mmol) and the mixture was stirred at 80° C. for 4 h. After cooling to ambient temperature, the mixture was concentrated and carried forward without further purification. ES-MS [M+1]⁺: 396.3.

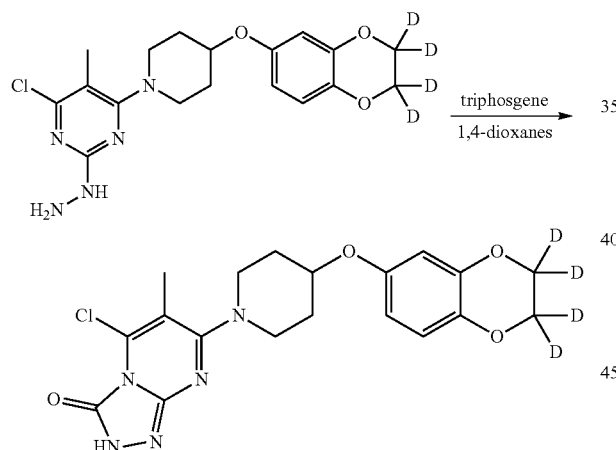

5-Chloro-7-(4-((2,3-dihydrobenzo[b][1,4]dioxin-6-yl-2,2,3,3-d₄)oxy)piperidin-1-yl)-6-methyl-[1,2,4]triazolo[4,3-a]pyrimidin-3(2H)-one. To a solution of 4-chloro-6-(4-((2,3-dihydrobenzo[b][1,4]dioxin-6-yl-2,2,3,3-d₄)oxy)piperidin-1-yl)-2-hydrazineyl-5-methylpyrimidine (170 mg, 0.43 mmol) in 1,4-dioxane (2.8 mL) was added triphosgene (127 mg, 0.43 mmol). The reaction was stirred at ambient temperature for 30 min. The mixture was diluted with water, and the formed precipitate was collected by vacuum filtration. The solid was dissolved in DCM (2 mL) and purified via normal phase column chromatography (0-40% MeOH/DCM) to afford the title compound. ¹H NMR (400 MHz, CDCl₃) δ 8.86 (s, 1H), 6.78 (d, J=8.7 Hz, 1H), 6.48 (d, J=2.8 Hz, 1H), 6.44 (dd, J=8.8, 2.9 Hz, 1H), 4.41 (tt, J=6.8, 3.5 Hz, 1H), 3.71-3.60 (m, 2H), 3.37 (ddd, J=13.4, 7.2, 3.7 Hz, 2H), 2.20 (s, 3H), 2.04 (ddt, J=12.0, 7.8, 3.6 Hz, 2H), 1.91 (dtd, J=13.7, 6.9, 3.5 Hz, 2H). ES-MS [M+1]⁺: 422.3.

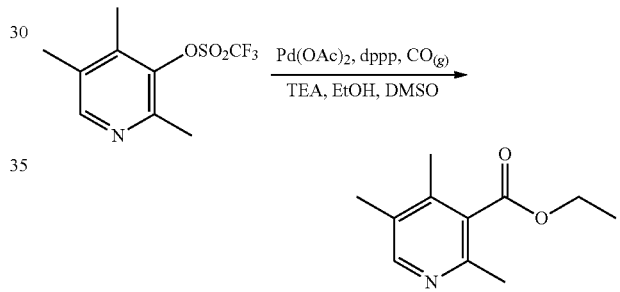

2,4,5-Trimethylpyridin-3-yl trifluoromethanesulfonate. A solution of 2,4,5-trimethylpyridin-3-ol (1.0 g, 7.29 mmol), triethylamine (2.03 mL, 14.6 mmol), and 4-dimethylaminopyridine (178 mg, 1.46 mmol) in DCM (21 mL) was cooled to 0° C. where N-phenylbis(trifluoromethanesulfonimide) (2.76 g, 7.73 mmol) was added. The solution was warmed to ambient temperature and stirred for 18 hours. The reaction mixture was concentrated onto Celite® and purified by normal-phase chromatography (0-15% EtOAc/Hex) to provide the title compound. ¹H NMR (400 MHz, CDCl₃) δ 8.25 (s, 1H), 2.57 (s, 3H), 2.30 (s, 3H), 2.28 (s, 3H). ES-MS [M+1]⁺: 270.

Ethyl 2,4,5-trimethylnicotinate. To a solution of 2,4,5-trimethylpyridin-3-yl trifluoromethanesulfonate (1.9 g, 7.06 mmol) in ethanol (12 mL) and DMSO (6 mL) was added triethylamine (9.8 mL, 70.6 mmol), 1,3-bis(diphenylphosphino)propane (437 mg, 1.06 mmol) and palladium(II) acetate (240 mg, 1.06 mmol). The mixture was placed under an atmosphere of CO$_{(g)}$ (50 psi) and heated to 80° C. for 18 hours. The reaction mixture was filtered over a pad of Celite® then washed with DCM/MeOH and concentrated. The residue was then diluted with water (~150 mL) and extracted with EtOAc (4×). The combined organic layers were dried (MgSO₄), filtered, and concentrated. The crude residue was purified by normal-phase chromatography (0-60% EtOAc/Hex) to afford the title compound. ¹H NMR (400 MHz, CDCl₃) δ 8.25 (s, 1H), 4.42 (q, J=7.1 Hz, 2H), 2.49 (s, 3H), 2.23 (s, 3H), 2.21 (s, 3H), 1.40 (t, J=7.1 Hz, 3H). ES-MS [M+1]⁺: 194.

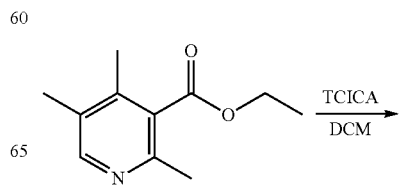

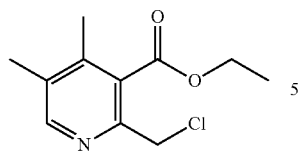

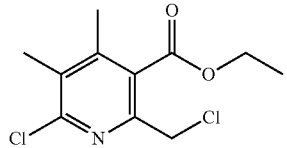

Ethyl 2-(chloromethyl)-4,5-dimethylnicotinate. To a stirred solution of ethyl 2,4,5-trimethylnicotinate (752 mg, 3.89 mmol) in DCM (19.5 mL) was added trichloroisocyanuric acid (1085 mg, 4.67 mmol) and the mixture was allowed to stir at ambient temperature for 12 h. Additional TCICA (226 mg, 0.97 mmol) was added and stirred for an additional 18 hours. Additional TCICA (300 mg, 1.29 mmol) was added and the mixture was allowed to stir for 3 hours. The pH was adjusted to 8 with a saturated aqueous $Na_2CO_3$ solution. The organic layer was isolated and the aqueous layer was further extracted with DCM (3×). The combined organics were dried ($MgSO_4$), filtered, and concentrated. The crude residue was purified by normal-phase chromatography (0-5% MeOH/DCM) to afford the title compound. $^1$H NMR (400 MHz, $CDCl_3$) δ 8.35 (s, 1H), 4.71 (s, 2H), 4.46 (q, J=7.2 Hz, 2H), 2.29 (s, 3H), 2.28 (s, 3H), 1.43 (t, J=7.1 Hz, 3H). ES-MS [M+1]$^+$: 228.

Ethyl 6-chloro-2-(chloromethyl)-4,5-dimethylnicotinate. To a solution of 2-(chloromethyl)-3-(ethoxycarbonyl)-4,5-dimethylpyridine 1-oxide (182 mg, 0.75 mmol) in MeCN (1.6 mL) was added phosphorus(V) oxychloride (348 μL, 3.73 mmol). The vial was sealed and the mixture was heated to 90° C. for 20 hours. After cooling to ambient temperature, the reaction mixture was slowly added to a stirred solution of saturated aqueous $NaHCO_3$, keeping the pH alkaline. DCM was added and the mixture was allowed to stir for 30 minutes. The organic layer was isolated and the aqueous layer was back extracted with chloroform/IPA (3:1) (3×). The combined organic layers were dried ($MgSO_4$), filtered, and concentrated. The crude residue was purified by normal-phase chromatography (0-15% EtOAc/hexanes) to afford the title compound. $^1$H NMR (400 MHz, $CDCl_3$) δ 4.66 (s, 2H), 4.46 (q, J=7.2 Hz, 2H), 2.39 (s, 3H), 2.33 (s, 3H), 1.42 (t, J=7.2 Hz, 3H). ES-MS [M+1]$^+$: 262/264.

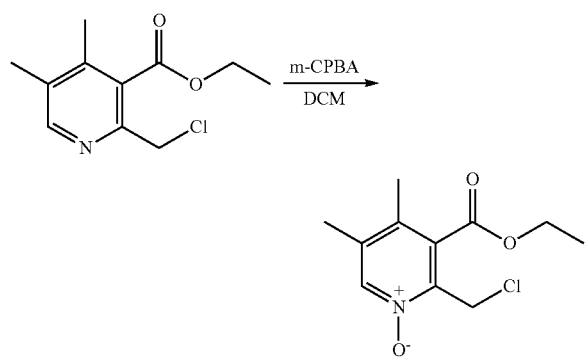

2-(Chloromethyl)-3-(ethoxycarbonyl)-4,5-dimethylpyridine 1-oxide. To a solution of ethyl 2-(chloromethyl)-4,5-dimethylnicotinate (216 μL, 1.38 mmol) in DCM (6.9 mL) at 0° C. was added 3-chloroperoxybenzoic acid (285 mg, 1.65 mmol) portionwise. The ice bath was removed and after 18 hours at rt, the mixture was concentrated directly onto Celite® and purified by normal-phase chromatography (0-80% EtOAc/DCM then 0-10% MeOH/DCM) to afford the title compound. $^1$H NMR (400 MHz, $CDCl_3$) δ 8.15 (s, 1H), 4.84 (s, 2H), 4.48 (q, J=7.2 Hz, 2H), 2.25 (s, 3H), 2.22 (s, 3H), 1.44 (t, J=7.2 Hz, 3H). ES-MS [M+1]$^+$: 244.

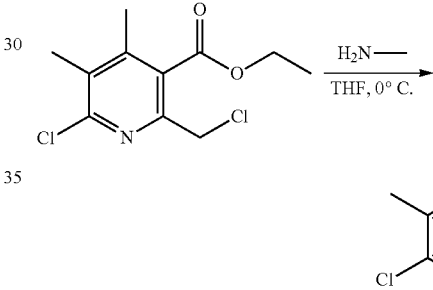

2-Chloro-3,4,6-trimethyl-6,7-dihydro-5H-pyrrolo[3,4-b]pyridin-5-one. To a solution of ethyl 6-chloro-2-(chloromethyl)-4,5-dimethylnicotinate (68 mg, 0.26 mmol) in THF (1.3 mL) was added methylamine (2.0 M solution in THF) (650 μL, 1.3 mmol) and the reaction was heated to 30° C. for 18 hours. The reaction was concentrated in vacuo to afford the title compound. $^1$H NMR (400 MHz, $CDCl_3$) δ 4.29 (s, 3H), 3.18 (s, 2H), 2.73 (s, 3H), 2.39 (s, 3H). ES-MS [M+1]$^+$: 211.

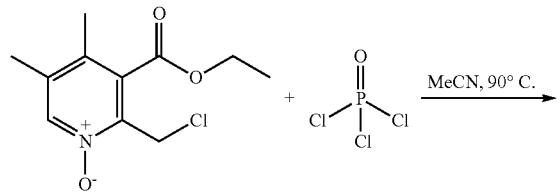

6-Hydroxy-4,5-dimethyl-2-oxo-1,2-dihydropyridine-3-carbonitrile. To a solution of 2-cyanoacetamide (2.0 g, 23.8 mmol) dissolved in methanol (30 mL) was added ethyl 2-methyl-3-oxobutanoate (3.37 mL, 23.89 mmol) and potassium hydroxide (2.04 g, 35.7 mmol). The mixture was then stirred at 65° C. for 4 hours before cooling to 4° C. The solids were collected by vacuum filtration rinsing with MeOH. The solid was dissolved in ~175 mL of hot water (70° C.). The solution was adjusted to pH-1 with aqueous HCl (5 M) and a precipitate was observed. The solids were collected by vacuum filtration rinsing with water to give the title compound. $^1$H NMR (400 MHz, DMSO) δ 2.23 (s, 1H), 1.90 (s, 1H). ES-MS [M+1]$^+$: 165.

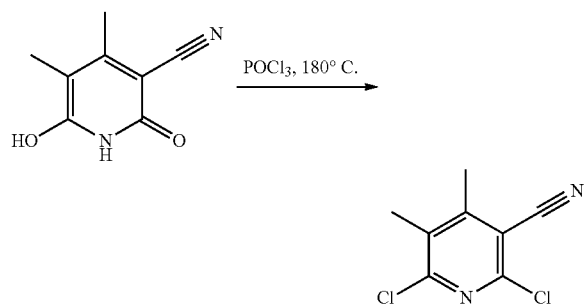

2,6-Dichloro-4,5-dimethylnicotinonitrile. A solution of 6-hydroxy-4,5-dimethyl-2-oxo-1,2-dihydropyridine-3-carbonitrile (2.28 g, 13.88 mmol) in phosphorus(v) oxychloride (10 mL) was heated to 180° C. After 6 hours, the heat source was removed and the reaction mixture at rt was poured into ice water (100 mL). The precipitate was collected by vacuum filtration to afford the title compound. $^1$H NMR (400 MHz, CDCl$_3$) δ 2.58 (s, 3H), 2.39 (s, 3H). ES-MS [M+1]$^+$: 201/203.

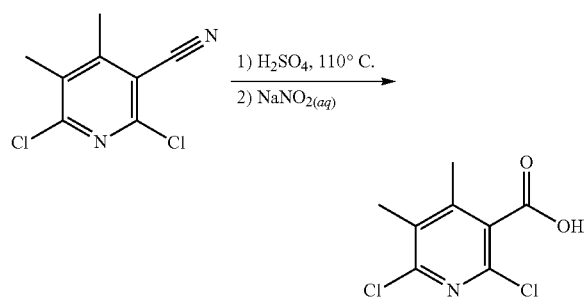

2,6-Dichloro-4,5-dimethylnicotinic acid. A stirred solution of 2,6-dichloro-4,5-dimethylnicotinonitrile (1.48 g, 7.36 mmol) in sulfuric acid (2.0 mL) was heated to 110° C. for 1 hour. After cooling to ambient temperature, the reaction mixture was cooled to 0° C. where an aqueous solution of sodium nitrite (671 mg, 9.58 mmol) (2.6 Min water) was added dropwise over a period of 15 minutes resulting in evolution of heat and a brown gas. The mixture was then warmed to ambient temperature for 15 minutes then heated to 60° C. for 18 hours. After cooling to ambient temperature, the reaction mixture was again cooled to 0° C. where an aqueous solution of sodium nitrite (186 mg, 2.66 mmol) (2.6 M in water) was added dropwise over a period of 15 minutes. The mixture was then warmed to ambient temperature for 15 minutes then heated to 60° C. for and additional 18 hours. After cooling to room temperature, the reaction mixture was added to ice water and the precipitate was collected by vacuum filtration to give the title compound. $^1$H NMR (400 MHz, DMSO) δ 2.32 (s, 3H), 2.31 (s, 3H). ES-MS [M+1]$^+$: 220/222.

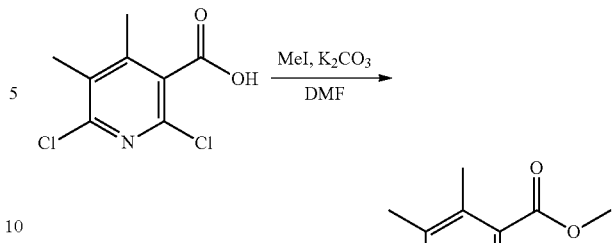

Methyl 2,6-dichloro-4,5-dimethylnicotinate. To a solution of 2,6-dichloro-4,5-dimethylnicotinic acid (960 mg, 4.36 mmol) in DMF (14.5 mL) was added potassium carbonate (918 mg, 6.54 mmol) and iodomethane (543 μL, 8.73 mmol). The mixture was stirred for 1 hour at ambient temperature before diluting with water and extracting with EtOAc (3×). The combined organic layers were dried (MgSO$_4$), filtered, and concentrated. The crude residue was purified by normal-phase chromatography (0-10% EtOAc/Hex) to afford the title compound. $^1$H NMR (400 MHz, CDCl$_3$) δ 3.97 (s, 3H), 2.35 (s, 3H), 2.29 (s, 3H). ES-MS [M+1]$^+$: 234/236.

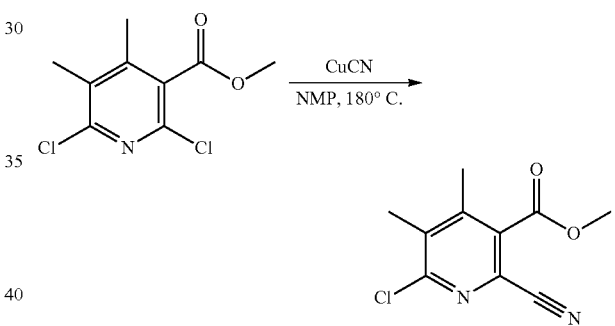

Methyl 6-chloro-2-cyano-4,5-dimethylnicotinate. A solution of methyl 2,6-dichloro-4,5-dimethylnicotinate (868 mg, 3.71 mmol) in NMP (4.4 mL) and copper(I) cyanide (498 mg, 5.56 mmol) was stirred for 3 hours at 180° C. under inert atmosphere. After cooling to ambient temperature, the reaction was poured into ice water and the solids were removed by filtration and washed with EtOAc. The filtrate was then extracted with EtOAc (3×) and the combined organics were dried (MgSO$_4$), filtered, and concentrated. The crude residue was purified by normal-phase chromatography (0-40% EtOAc/Hex) to afford the title compound. ES-MS [M+1]$^+$: 225.

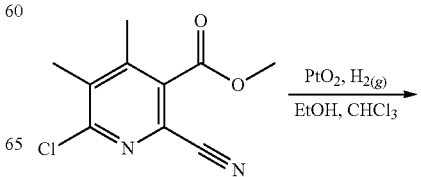

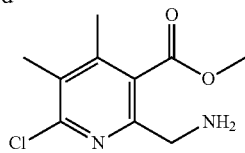

Methyl 2-(aminomethyl)-6-chloro-4,5-dimethylnicotinate. A solution of methyl 6-chloro-2-cyano-4,5-dimethylnicotinate (219 mg, 0.98 mmol) in ethanol (4.6 mL)/chloroform (1.5 mL) (3:1) was added platinum(IV) oxide (38 mg, 0.17 mmol). The flask was evacuated under vacuum and purged with hydrogen gas (process repeated 3×). The mixture was stirred under an atmosphere of hydrogen (balloon) for 25 hours. The reaction mixture was filtered over Celite®, washed with DCM/MeOH, and the filtrate was concentrated and carried forward without further purification. ES-MS [M+1]$^+$: 229.

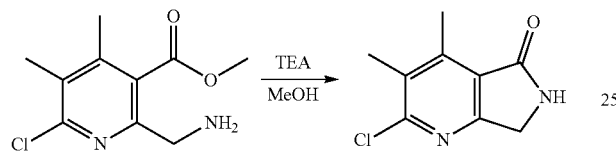

2-Chloro-3,4-dimethyl-6,7-dihydro-5H-pyrrolo[3,4-b]pyridin-5-one. To a vial was added a solution of methyl 2-(aminomethyl)-6-chloro-4,5-dimethylnicotinate (236 mg, 0.97 mmol) and triethylamine (680 μL, 4.88 mmol) in methanol (4.9 mL). The solution was allowed to stir at ambient temperature for 18 hours then concentrated onto Celite® and purified by normal-phase chromatography (0-3% MeOH/DCM) to afford the title compound. $^1$H NMR (400 MHz, CDCl$_3$) δ 6.06 (s, 1H), 4.38 (s, 2H), 2.74 (s, 3H), 2.41 (s, 3H). ES-MS [M+1]$^+$: 197.

b. Exemplified compounds of the invention

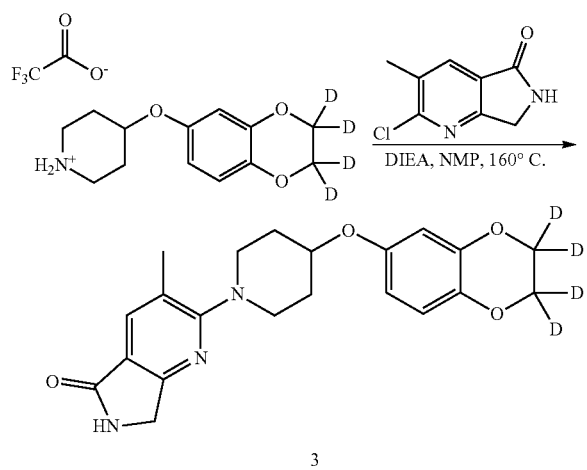

2-(4-((2,3-Dihydrobenzo[b][1,4]dioxin-6-yl-2,2,3,3-d$_4$)oxy)piperidin-1-yl)-3-methyl-6,7-dihydro-5H-pyrrolo[3,4-b]pyridin-5-one (Compound 3). To a solution of 4-((2,3-dihydrobenzo[b][1,4]dioxin-6-yl-2,2,3,3-d$_4$)oxy)piperidin-1-ium 2,2,2-trifluoroacetate (503 mg, 1.42 mmol) in NMP (6.8 mL) was added 2-chloro-3-methyl-6,7-dihydro-5H-pyrrolo[3,4-b]pyridin-5-one (200 mg, 1.10 mmol) and N,N-diisopropylethylamine (1.91 mL, 10.95 mmol). The reaction mixture was heated to 160° C. After 18 hr, the crude material was purified by RP-HPLC (10-55% MeCN/0.05% aqueous NH$_4$OH). The fractions containing the desired product were concentrated and repurified using normal-phase flash column chromatography (0-7% MeOH/DCM) to give the title compound (303 mg). $^1$H NMR (400 MHz, CDCl$_3$) δ 7.79 (d, J=0.9 Hz, 1H), 6.78 (d, J=8.7 Hz, 1H), 6.51 (d, J=2.8 Hz, 1H), 6.47 (dd, J=8.7, 2.9 Hz, 1H), 6.02 (s, 1H), 4.40-4.30 (m, 3H), 3.55 (ddd, J=11.5, 7.0, 3.6 Hz, 2H), 3.14 (ddd, J=12.5, 8.4, 3.3 Hz, 2H), 2.35 (d, J=0.9 Hz, 3H), 2.16-2.07 (m, 2H), 1.92 (dtd, J=12.1, 8.0, 3.5 Hz, 2H); ES-MS [M+1]$^+$: 386.

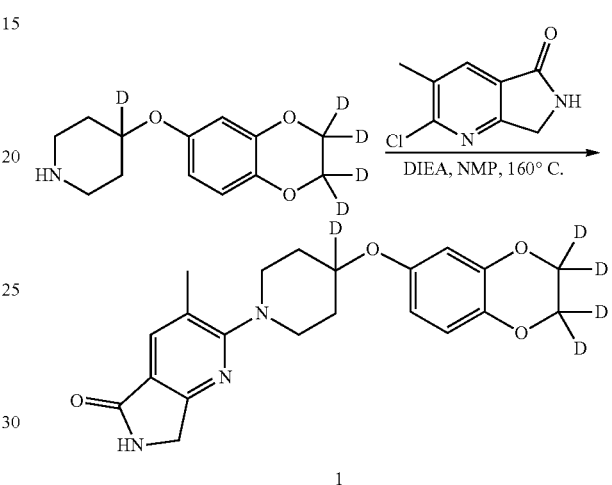

2-(4-((2,3-Dihydrobenzo[b][1,4]dioxin-6-yl-2,2,3,3-d$_4$)oxy)piperidin-1-yl-4-d)-3-methyl-6,7-dihydro-5H-pyrrolo[3,4-b]pyridin-5-one (Compound 1). Prepared in a similar manner as compound 3 to provide the title compound. ES-MS [M+H]$^+$=387. $^1$H NMR (400 MHz, CDCl$_3$) δ 7.79 (d, J=0.9 Hz, 1H), 6.78 (d, J=8.7 Hz, 1H), 6.50 (d, J=2.8 Hz, 1H), 6.46 (dd, J=8.8, 2.9 Hz, 1H), 6.07-5.85 (m, 1H), 4.35 (s, 2H), 3.55 (ddd, J=11.4, 6.9, 3.5 Hz, 2H), 3.14 (ddd, J=18.2, 8.7, 4.5 Hz, 2H), 2.35 (d, J=0.9 Hz, 3H), 2.16-2.00 (m, 2H), 1.92 (ddd, J=12.6, 8.4, 3.5 Hz, 2H).

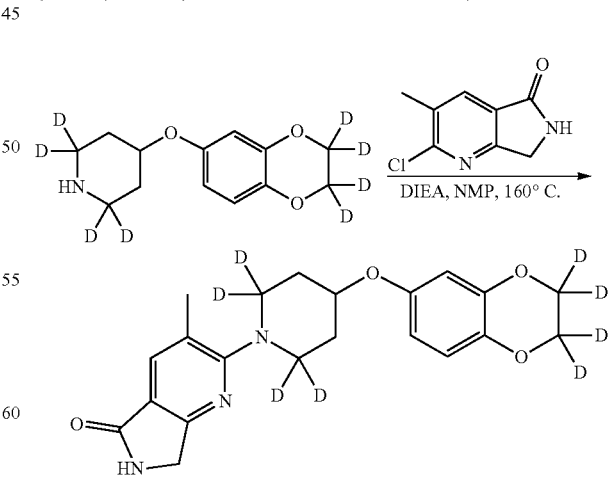

2-(4-((2,3-Dihydrobenzo[b][1,4]dioxin-6-yl-2,2,3,3-d$_4$)oxy)piperidin-1-yl-2,2,6,6-d$_4$)-6,7-dihydro-5H-pyrrolo[3,4- b]pyridin-5-one (Compound 2). Prepared in a similar manner as compound 3 to provide the title compound. ¹H NMR (400 MHz, MeOD) δ 7.79 (d, J=0.9 Hz, 1H), 6.73 (d, J=8.6 Hz, 1H), 6.49 (d, J=2.7 Hz, 1H), 6.47 (dd, J=8.6, 2.9 Hz, 1H), 4.44 (tt, J=7.5, 3.8 Hz, 1H), 4.33 (s, 2H), 2.38 (d, J=0.8 Hz, 3H), 2.08 (dd, J=13.1, 3.7 Hz, 2H), 1.92-1.81 (m, 2H); ES-MS [M+H]⁺=390.

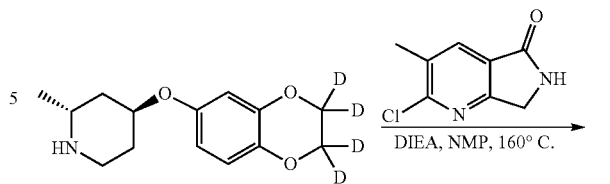

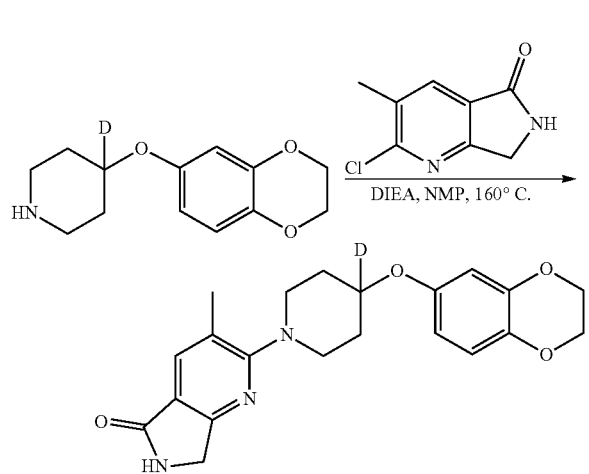

10

2-(4-((2,3-Dihydrobenzo[b][1,4]dioxin-6-yl)oxy)piperidin-1-yl-4-d)-3-methyl-6,7-dihydro-5H-pyrrolo[3,4-b]pyridin-5-one (Compound 10). Prepared in a similar manner as compound 3 to provide the title compound. ¹H NMR (400 MHz, CDCl₃) δ 7.78 (s, 1H), 6.91 (s, 1H), 6.77 (d, J=8.7 Hz, 1H), 6.52-6.42 (m, 2H), 4.36 (s, 2H), 4.28-4.17 (m, 4H), 3.55 (ddd, J=11.6, 7.0, 3.5 Hz, 2H), 3.14 (ddd, J=12.5, 8.4, 3.3 Hz, 2H), 2.34 (s, 3H), 2.09 (ddd, J=13.1, 7.0, 3.3 Hz, 2H), 1.96-1.86 (m, 2H); ES-MS [M+1]⁺: 383.3.

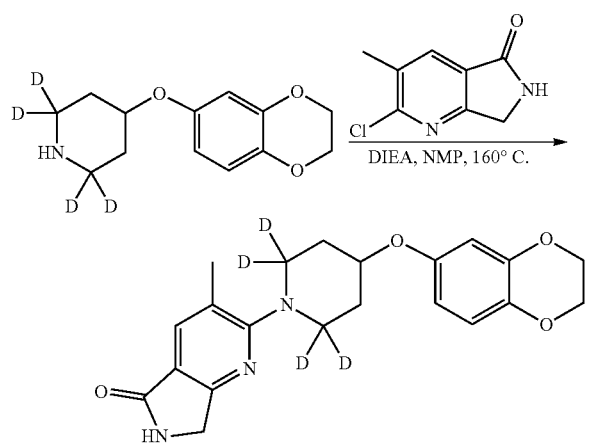

11

2-(4-((2,3-Dihydrobenzo[b][1,4]dioxin-6-yl)oxy)piperidin-1-yl-2,2,6,6-d₄)-3-methyl-6,7-dihydro-5H-pyrrolo[3,4-b]pyridin-5-one (Compound 11). Prepared in a similar manner as compound 3 to provide the title compound. ¹H NMR (400 MHz, CDCl₃) δ 7.79 (s, 1H), 6.77 (d, J=8.8 Hz, 1H), 6.50 (d, J=2.8 Hz, 1H), 6.46 (dd, J=8.7, 2.9 Hz, 1H), 4.41-4.33 (m, 3H), 4.27-4.19 (m, 4H), 2.35 (s, 3H), 2.08 (dd, J=13.2, 3.8 Hz, 2H), 1.91 (dd, J=13.2, 7.5 Hz, 2H); ES-MS [M+1]⁺: 386.3.

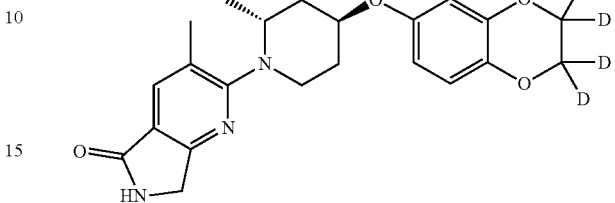

4

2-((2R,4S)-4-((2,3-Dihydrobenzo[b][1,4]dioxin-6-yl-2,2,3,3-d₄)oxy)-2-methylpiperidin-1-yl)-3-methyl-6,7-dihydro-5H-pyrrolo[3,4-b]pyridin-5-one (Compound 4). Prepared in a similar manner as compound 3 to provide the title compound. ES-MS [M+H]⁺=400.

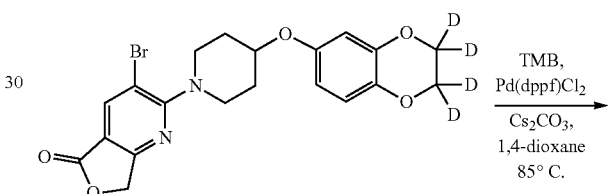

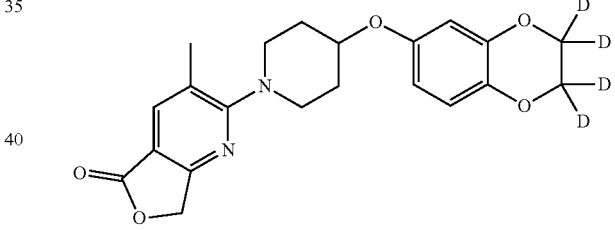

8

2-(4-((2,3-Dihydrobenzo[b][1,4]dioxin-6-yl-2,2,3,3-d₄)oxy)piperidin-1-yl)-3-methylfuro[3,4-b]pyridin-5(7H)-one (Compound 8). 3-Bromo-2-(4-((2,3-dihydrobenzo[b][1,4]dioxin-6-yl-2,2,3,3-d₄)oxy)piperidin-1-yl)furo[3,4-b]pyridin-5(7H)-one (131 mg, 0.25 mmol), cesium carbonate (241 mg, 0.74 mmol), trimethylboroxine (50% wt in THF) (207 µL, 0.74 mmol), [1,1'-bis(diphenylphosphino)ferrocene]dichloropalladium(II) (36 mg, 0.05 mmol), and 1,4-dioxane (1.2 mL) were charged into a vial. The mixture was evacuated and purged with nitrogen and stirred at 85° C. for 17 h. After cooling to ambient temperature, the reaction was filtered through a pad of Celite® which was rinsed thoroughly with DCM/MeOH then concentrated onto Celite®. The crude product was purified via normal phase column chromatography (0-70% EtOAc/Hexanes) to give the title compound (71 mg). ES-MS [M+1]⁺. 387; ¹H NMR (400 MHz, CDCl₃) δ 7.77 (d, J=1.0 Hz, 1H), 6.78 (d, J=8.7 Hz, 1H), 6.50 (d, J=2.8 Hz, 1H), 6.46 (dd, J=8.8, 2.9 Hz, 1H), 5.13 (s, 2H), 4.40 (tt, J=7.3, 3.7 Hz, 1H), 3.64 (ddd, J=11.7, 7.4, 3.5 Hz, 2H), 3.26 (ddd, J=12.5, 8.0, 3.4 Hz, 2H), 2.35 (d, J=0.8 Hz, 3H), 2.14-2.03 (m, 2H), 2.00-1.78 (m, 2H).

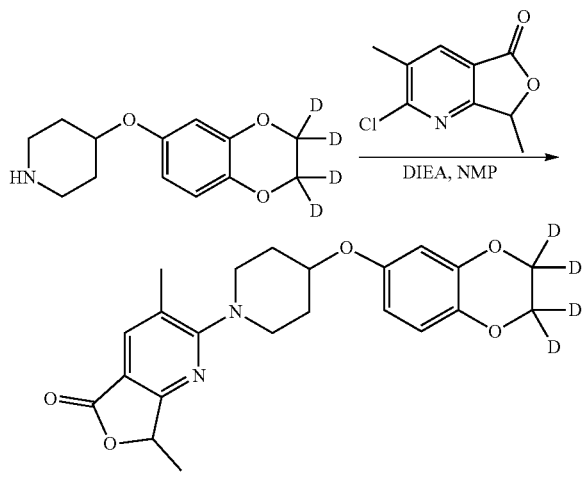

2-(4-((2,3-Dihydrobenzo[b][1,4]dioxin-6-yl-2,2,3,3-d₄) oxy)piperidin-1-yl)-3,7-dimethylfuro[3,4-b]pyridin-5(7H)-one (Compound 9). To a solution of 2-chloro-3,7-dimethylfuro[3,4-b]pyridin-5(7H)-one (17.8 mg, 0.06 mmol) in DMSO (0.5 mL) was added 4-((2,3-dihydrobenzo[b][1,4]dioxin-6-yl-2,2,3,3-d₄)oxy)piperidine (31 mg, 0.07 mmol) and N,N-diisopropylethylamine (38 µL, 0.18 mmol). The mixture was stirred at ambient temperature for 18 h, then 40° C. for 3 h. The crude material was purified via RP-HPLC (5-70% ACN/0.1% aqueous TFA). Fractions containing desired product were basified with saturated aqueous NaHCO₃ then extracted with 3:1 chloroform/IPA (3:1) (3×). The combined organics were passed through a phase separator and the solvents were concentrated to give the title compound. ES-MS [M+1]⁺: 401; ¹H NMR (400 MHz, CDCl₃) δ 7.74 (d, J=1.0 Hz, 1H), 6.78 (d, J=8.7 Hz, 1H), 6.51 (d, J=2.8 Hz, 1H), 6.47 (dd, J=8.7, 2.9 Hz, 1H), 5.33 (q, J=6.8 Hz, 1H), 4.40 (tt, J=7.4, 3.7 Hz, 1H), 3.70-3.60 (m, 2H), 3.27 (ddd, J=12.7, 8.0, 3.4 Hz, 2H), 2.34 (s, 3H), 2.09 (ddd, J=10.9, 7.1, 3.5 Hz, 2H), 1.92 (qd, J=7.9, 3.8 Hz, 2H), 1.61 (d, J=6.7 Hz, 3H).

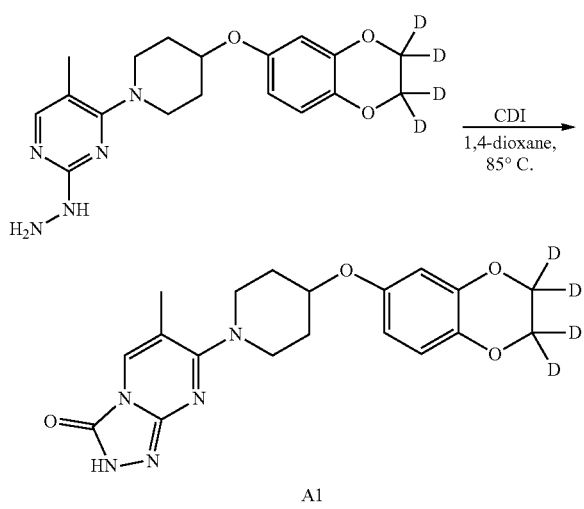

7-(4-((2,3-Dihydrobenzo[b][1,4]dioxin-6-yl-2,2,3,3-d₄) oxy)piperidin-1-yl)-6-methyl-[1,2,4]triazolo[4,3-a]pyrimidin-3(2H)-one (Compound A1). To a solution of 4-(4-((2,3-dihydrobenzo[b][1,4]dioxin-6-yl-2,2,3,3-d₄)oxy)piperidin-1-yl)-2-hydrazineyl-5-methylpyrimidine (26.2 mg, 0.07 mmol) in 1,4-dioxane (130 µL) was added 1,1'-carbonyldiimidazole (18.8 mg, 0.12 mmol). The reaction was heated to 85° C. for 18 h. The reaction was cooled to ambient temperature where another 1.6 eq of CDI was added and the mixture was then stirred at 85° C. for 8 h. After cooling to ambient temperature, the mixture was diluted with water, and the formed precipitate was collected by vacuum filtration. The solid was dissolved in DMSO (2 mL) and purified via RP-HPLC (5-50% ACN/0.1% aqueous TFA). Fractions containing the product were basified with saturated aqueous NaHCO₃ then extracted with chloroform/IPA (3:1) (3×). The combined organics were passed through a phase separator and the solvents were concentrated to afford title compound. ES-MS [M+1]⁺: 388.

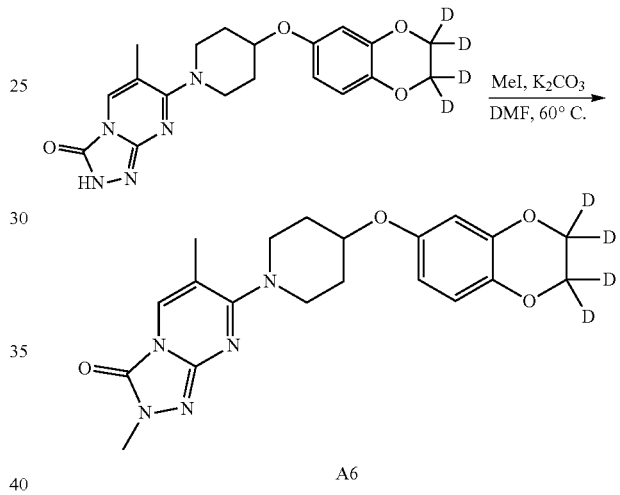

7-(4-((2,3-Dihydrobenzo[b][1,4]dioxin-6-yl-2,2,3,3-d₄) oxy)piperidin-1-yl)-2,6-dimethyl-[1,2,4]triazolo[4,3-a]pyrimidin-3(2H)-one (Compound A6). To a suspension of 7-(4-((2,3-dihydrobenzo[b][1,4]dioxin-6-yl-2,2,3,3-d₄)oxy) piperidin-1-yl)-6-methyl-[1,2,4]triazolo[4,3-a]pyrimidin-3 (2H)-one (797 mg, 2.1 mmol) and potassium carbonate (577 mg, 4.1 mmol) in DMF (30 mL) was added iodomethane (0.22 mL, 3.5 mmol). The reaction was stirred at 60° C. for 18 h. The reaction was diluted with water and 3:1 CHCl₃/IPA. The layers were separated and the aqueous layer was extracted (3×) with CHCl₃/IPA. The combined organic layers were washed with brine (2×), dried (MgSO₄), filtered, and concentrated. The crude sample was purified by reverse-phase chromatography (10-50% MeCN/Water/0.05% NH₄OH) to afford the title compound (472 mg). ¹H NMR (400 MHz, DMSO) δ 7.90 (d, J=1.3 Hz, 1H), 6.75 (d, J=8.8 Hz, 1H), 6.52 (d, J=2.9 Hz, 1H), 6.47 (dd, J=8.8, 2.9 Hz, 1H), 4.49 (tt, J=7.7, 3.7 Hz, 1H), 3.77-3.62 (m, 2H), 3.39 (s, 3H), 3.31-3.25 (m, 2H), 2.16 (d, J=1.2 Hz, 3H), 2.06-1.90 (m, 2H), 1.67 (dtd, J=12.2, 8.2, 3.5 Hz, 2H). ES-MS [M+1]⁺: 402.1.

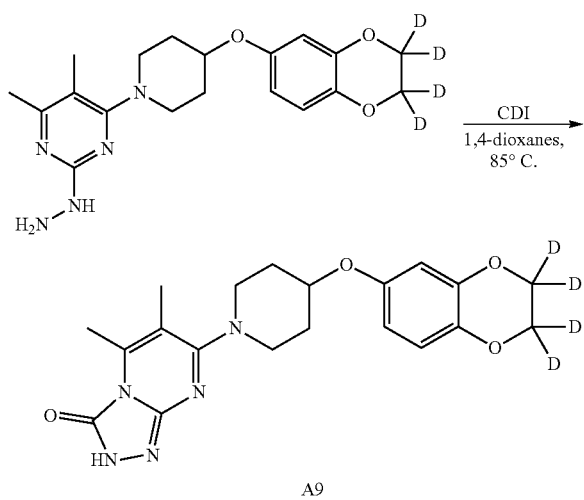

A9

7-(4-((2,3-Dihydrobenzo[b][1,4]dioxin-6-yl-2,2,3,3-d₄)oxy)piperidin-1-yl)-5,6-dimethyl-[1,2,4]triazolo[4,3-a]pyrimidin-3(2H)-one (Compound A9). To a solution of 4-(4-((2,3-dihydrobenzo[b][1,4]dioxin-6-yl-2,2,3,3-d₄)oxy)piperidin-1-yl)-2-hydrazineyl-5,6-dimethylpyrimidine (53 mg, 0.14 mmol) in 1,4-dioxane (250 μL) was added 1,1'-carbonyldiimidazole (37 mg, 0.23 mmol) and the mixture was heated to 85° C. for 18 h. After cooling to ambient temperature, the mixture was diluted with water, and the precipitate formed was collected by vacuum filtration. The solid was then dissolved in DCM/MeOH, dried (Na₂SO₄), filtered, and concentrated to give title compound (51 mg). ¹H NMR (400 MHz, CDCl₃) δ 8.36 (s, 1H), 6.78 (d, J=8.7 Hz, 1H), 6.48 (d, J=2.8 Hz, 1H), 6.44 (dd, J=8.8, 2.9 Hz, 1H), 4.43-4.22 (m, 1H), 3.62 (ddd, J=12.2, 7.7, 3.4 Hz, 2H), 3.27 (ddd, J=12.6, 7.7, 3.6 Hz, 2H), 2.76 (s, 3H), 2.07 (s, 3H), 2.07-2.00 (m, 2H), 1.94-1.81 (m, 2H). ES-MS [M+1]⁺: 402.

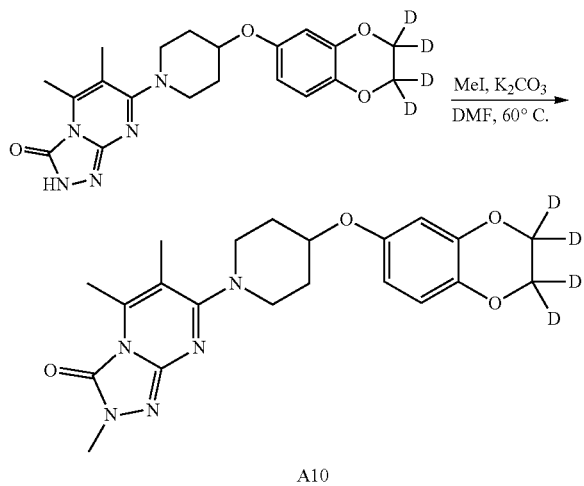

A10

7-(4-((2,3-Dihydrobenzo[b][1,4]dioxin-6-yl-2,2,3,3-d₄)oxy)piperidin-1-yl)-2,5,6-trimethyl-[1,2,4]triazolo[4,3-a]pyrimidin-3(2H)-one (Compound A10). To a solution of 7-(4-((2,3-dihydrobenzo[b][1,4]dioxin-6-yl-2,2,3,3-d₄)oxy)piperidin-1-yl)-5,6-dimethyl-[1,2,4]triazolo[4,3-a]pyrimidin-3(2H)-one (2.05 g, 5.1 mmol) in DMF (25 mL) was added potassium carbonate (1.43 g, 10.2 mmol) followed by iodomethane (0.48 mL, 7.7 mmol). The mixture was heated at 60° C. for 18 h. To the reaction was added 50 mL water, and the resulting precipitate was filtered, washed with water, and dried under high vacuum. The solid was purified by reverse-phase chromatography (10-60% MeCN/Water/0.05% NH₄OH) to afford the title compound (940 mg). ¹H NMR (400 MHz, DMSO) δ 6.75 (d, J=8.8 Hz, 1H), 6.52 (d, J=2.8 Hz, 1H), 6.47 (dd, J=8.8, 2.9 Hz, 1H), 4.46 (dt, J=7.9, 4.0 Hz, 1H), 3.59-3.46 (m, 2H), 3.36 (s, 3H), 3.14 (ddd, J=12.8, 8.8, 3.2 Hz, 2H), 2.65 (s, 3H), 2.01 (s, 3H), 2.01-1.95 (m, 2H), 1.68 (dtd, J=12.2, 8.2, 3.4 Hz, 2H). ES-MS [M+1]⁺: 416.2.

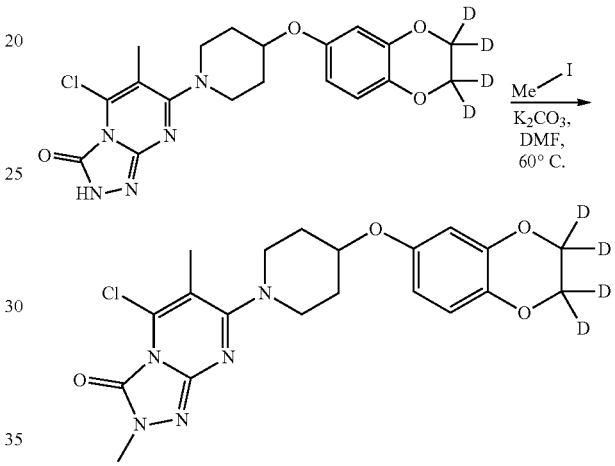

5-Chloro-7-(4-((2,3-dihydrobenzo[b][1,4]dioxin-6-yl-2,2,3,3-d₄)oxy)piperidin-1-yl)-2,6-dimethyl-[1,2,4]triazolo[4,3-a]pyrimidin-3(2H)-one (Compound A11). A solution of 5-chloro-7-(4-((2,3-dihydrobenzo[b][1,4]dioxin-6-yl-2,2,3,3-d₄)oxy)piperidin-1-yl)-6-methyl-[1,2,4]triazolo[4,3-a]pyrimidin-3(2H)-one (20 mg, 0.05 mmol) and potassium carbonate (13 mg, 0.09 mmol) in DMF (0.25 mL) was stirred at ambient temperature for 20 min. Iodomethane (4 μL, 0.07 mmol) was then added, and the mixture was stirred at 60° C. for 18 h. The mixture was added to water (10 mL) and extracted with EtOAc (3×). The collected organic layers were dried (Na₂SO₄), filtered, and concentrated. The crude material was purified via RP-HPLC (15-55% ACN/0.1% aqueous TFA). The fractions containing desired product were basified with saturated aqueous NaHCO₃ then extracted with 3:1 chloroform/IPA (3×). The combined organics were passed through a phase separator and the solvents were concentrated to give the title compound (9 mg). ¹H NMR (400 MHz, CDCl₃) δ 6.77 (d, J=8.7 Hz, 1H), 6.48 (d, J=2.8 Hz, 1H), 6.44 (dd, J=8.7, 2.8 Hz, 1H), 4.40 (tt, J=6.8, 3.5 Hz, 1H), 3.64 (ddd, J=12.3, 8.2, 3.4 Hz, 2H), 3.53 (s, 3H), 3.35 (ddd, J=13.4, 7.2, 3.6 Hz, 2H), 2.19 (s, 3H), 2.03 (ddt, J=12.1, 7.9, 3.8 Hz, 2H), 1.90 (dtd, J=13.6, 6.9, 3.4 Hz, 2H). ES-MS [M+1]⁺: 436.3.

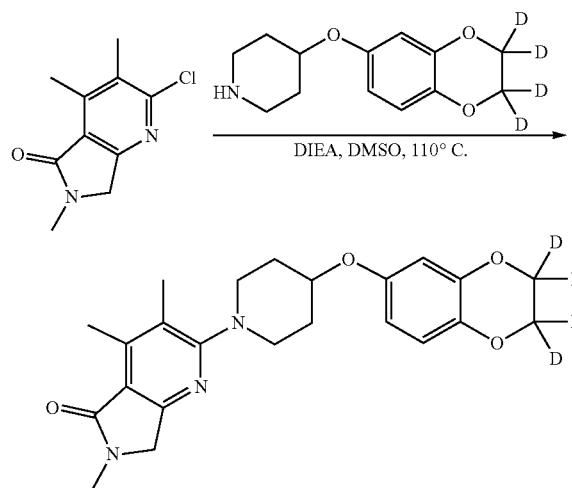

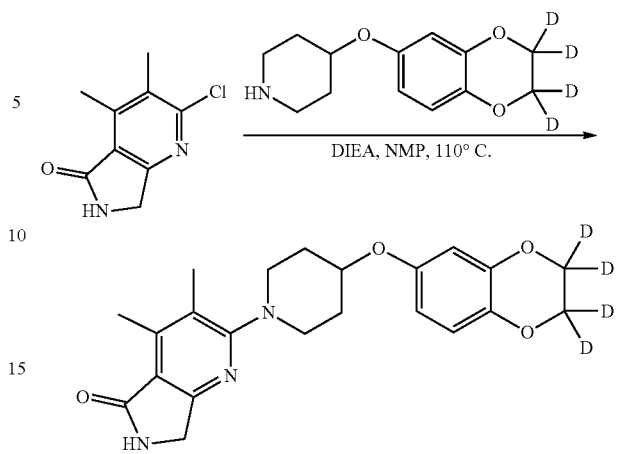

2-(4-((2,3-Dihydrobenzo[b][1,4]dioxin-6-yl-2,2,3,3-$d_4$) oxy)piperidin-1-yl)-3,4,6-trimethyl-6,7-dihydro-5H-pyrrolo [3,4-b]pyridin-5-one (Compound 12). Prepared in a similar manner as Compound 3. $^1$H NMR (400 MHz, CDCl$_3$) δ 6.77 (d, J=8.7 Hz, 1H), 6.51 (d, J=2.8 Hz, 1H), 6.47 (dd, J=8.7, 2.9 Hz, 1H), 4.33 (tt, J=7.8, 3.8 Hz, 1H), 4.21 (s, 2H), 3.44 (ddd, J=11.2, 6.6, 3.7 Hz, 2H), 3.15 (s, 3H), 3.04 (ddd, J=12.5, 8.8, 3.2 Hz, 2H), 2.62 (s, 3H), 2.22 (s, 3H), 2.10 (dtd, J=12.5, 8.0, 4.6 Hz, 2H), 1.92 (dtd, J=12.3, 8.3, 3.5 Hz, 2H). ES-MS [M+1]$^+$: 414.

2-(4-((2,3-Dihydrobenzo[b][1,4]dioxin-6-yl-2,2,3,3-$d_4$) oxy)piperidin-1-yl)-3,4-dimethyl-6,7-dihydro-5H-pyrrolo [3,4-b]pyridin-5-one (Compound 13). Prepared in a similar manner as Compound 3. $^1$H NMR (400 MHz, CDCl$_3$) δ 6.78 (d, J=8.7 Hz, 1H), 6.51 (d, J=2.8 Hz, 1H), 6.47 (dd, J=8.8, 2.8 Hz, 1H), 5.85 (s, 1H), 4.34 (tt, J=7.7, 3.8 Hz, 1H), 4.28 (s, 2H), 3.52-3.41 (m, 2H), 3.06 (ddd, J=12.5, 8.7, 3.2 Hz, 2H), 2.63 (s, 3H), 2.23 (s, 3H), 2.16-2.03 (m, 2H), 1.92 (dtd, J=12.3, 8.2, 3.5 Hz, 2H). ES-MS [M+1]$^+$: 400.

The compounds shown in Table 1 may be prepared using the methods shown in the preceding Schemes and Examples with the appropriate starting materials.

TABLE 1

| Cpd. No. | Name | Structure | ES-MS [M + 1]$^+$ |
|---|---|---|---|
| 1 | 2-(4-((2,3-dihydrobenzo[b][1,4]dioxin-6-yl-2,2,3,3-$d_4$)oxy)piperidin-1-yl-4-d)-3-methyl-6,7-dihydro-5H-pyrrolo[3,4-b]pyridin-5-one | 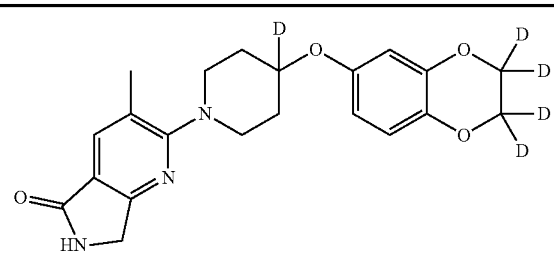 | 387.4 |
| 2 | 2-(4-((2,3-dihydrobenzo[b][1,4]dioxin-6-yl-2,2,3,3-$d_4$)oxy)piperidin-1-yl-2,2,6,6-$d_4$)-3-methyl-6,7-dihydro-5H-pyrrolo[3,4-b]pyridin-5-one | 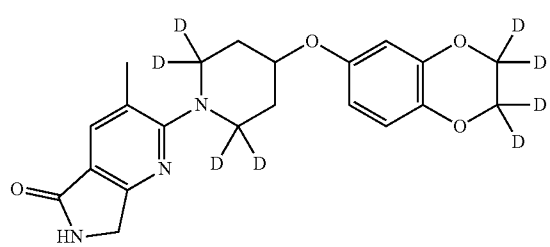 [SMILES: [2H]C1([2H])CC(Oc2ccc3c(c2)OC([2H])([2H])C([2H])([2H])O3)CC([2H])([2H])N1c1nc2c(cc1C)C(=O)NC2] | 390 |
| 3 | 2-(4-((2,3-dihydrobenzo[b][1,4]dioxin-6-yl-2,2,3,3-$d_4$)oxy)piperidin-1-yl)-3-methyl-6,7-dihydro-5H-pyrrolo[3,4-b]pyridin-5-one | 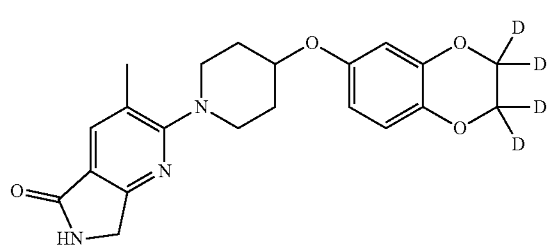 [SMILES: [2H]C1([2H])Oc2ccc(OC3CCN(c4nc5c(cc4C)C(=O)NC5)CC3)cc2OC1([2H])[2H]] | 386.5 |

TABLE 1-continued

| Cpd. No. | Name | Structure | ES-MS [M + 1]+ |
|---|---|---|---|
| 4 | 2-((2R,4S)-4-((2,3-dihydrobenzo[b][1,4]dioxin-6-yl-2,2,3,3-d4)oxy)-2-methylpiperidin-1-yl)-3-methyl-6,7-dihydro-5H-pyrrolo[3,4-b]pyridin-5-one | 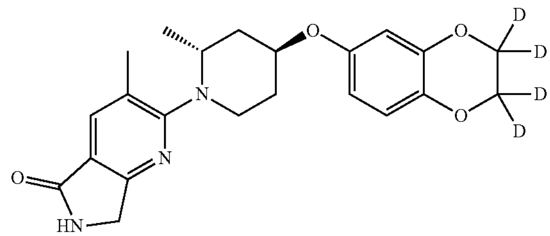 [SMILES: [2H]C1([2H])Oc2ccc(O[C@H]3CCN(c4nc5c(cc4C)C(=O)NC5)[C@H](C)C3)cc2OC1([2H])[2H]] | 400.5 |
| 5 | 2-(4-((2,3-dihydrobenzo[b][1,4]dioxin-6-yl-2,2,3,3-d4)oxy)piperidin-1-yl)-3,6-dimethyl-6,7-dihydro-5H-pyrrolo[3,4-b]pyridin-5-one | 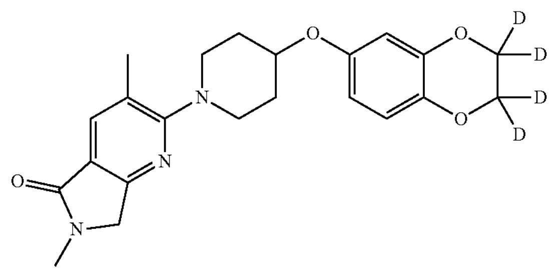 [SMILES: [2H]C1([2H])Oc2ccc(OC3CCN(c4nc5c(cc4C)C(=O)N(C)C5)CC3)cc2OC1([2H])[2H]] | 400.3 |
| 6 | 6-cyclopropyl-2-(4-((2,3-dihydrobenzo[b][1,4]dioxin-6-yl-2,2,3,3-d4)oxy)piperidin-1-yl)-3-methyl-6,7-dihydro-5H-pyrrolo[3,4-b]pyridin-5-one | 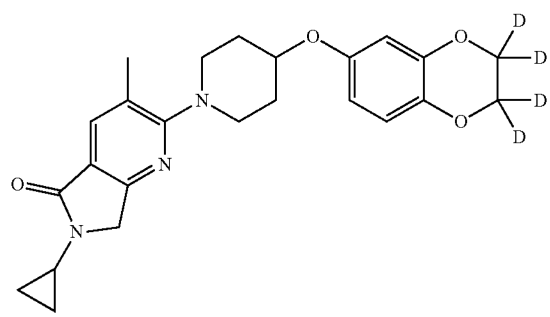 [SMILES: [2H]C1([2H])Oc2ccc(OC3CCN(c4nc5c(cc4C)C(=O)N(C4CC4)C5)CC3)cc2OC1([2H])[2H]] | 426.4 |
| 7 | 6-cyclopentyl-2-(4-((2,3-dihydrobenzo[b][1,4]dioxin-6-yl-2,2,3,3-d4)oxy)piperidin-1-yl)-3-methyl-6,7-dihydro-5H-pyrrolo[3,4-b]pyridin-5-one | 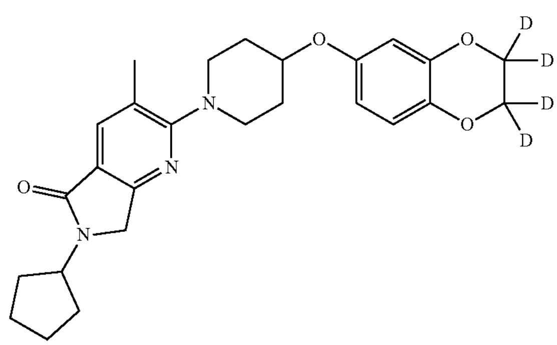 [SMILES: [2H]C1([2H])Oc2ccc(OC3CCN(c4nc5c(cc4C)C(=O)N(C4CCCC4)C5)CC3)cc2OC1([2H])[2H]] | 454.4 |
| 8 | 2-(4-((2,3-dihydrobenzo[b][1,4]dioxin-6-yl-2,2,3,3-d4)oxy)piperidin-1-yl)-3-methylfuro[3,4-b]pyridin-5(7H)-one | 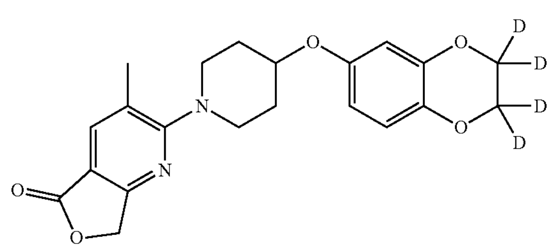 [SMILES: [2H]C1([2H])Oc2ccc(OC3CCN(c4nc5c(cc4C)C(=O)OC5)CC3)cc2OC1([2H])[2H]] | 387.3 |

TABLE 1-continued

| Cpd. No. | Name | Structure | ES-MS [M + 1]+ |
|---|---|---|---|
| 9 | 2-(4-((2,3-dihydrobenzo[b][1,4]dioxin-6-yl-2,2,3,3-d₄)oxy)piperidin-1-yl)-3,7-dimethylfuro[3,4-b]pyridin-5(7H)-one | 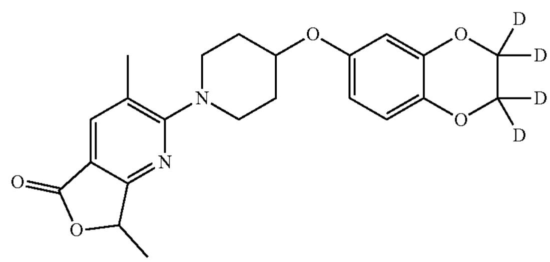 [SMILES: [2H]C1([2H])Oc2ccc(OC3CCN(c4nc5c(cc4C)C(=O)OC5C)CC3)cc2OC1([2H])[2H]] | 401.3 |
| 10 | 2-(4-((2,3-dihydrobenzo[b][1,4]dioxin-6-yl)oxy)piperidin-1-yl-4-d)-3-methyl-6,7-dihydro-5H-pyrrolo[3,4-b]pyridin-5-one | 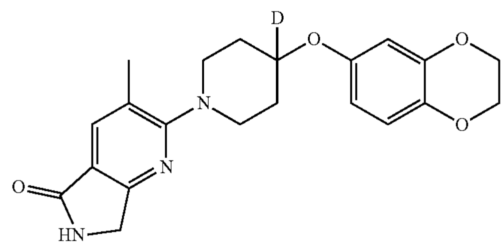 [SMILES: [2H]C1(Oc2ccc3c(c2)OCCO3)CCN(c2nc3c(cc2C)C(=O)NC3)CC1] | 383.3 |
| 11 | 2-(4-((2,3-dihydrobenzo[b][1,4]dioxin-6-yl)oxy)piperidin-1-yl-2,2,6,6-d₄)-3-methyl-6,7-dihydro-5H-pyrrolo[3,4-b]pyridin-5-one | 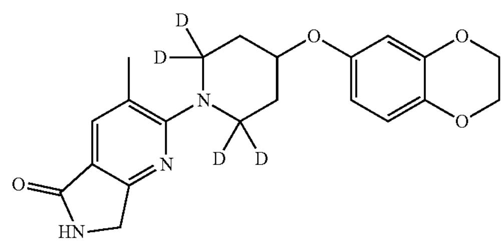 [SMILES: [2H]C1([2H])CC(Oc2ccc3c(c2)OCCO3)CC([2H])([2H])N1c1nc2c(cc1C)C(=O)NC2] | 386.3 |
| 12 | 2-(4-((2,3-dihydrobenzo[b][1,4]dioxin-6-yl-2,2,3,3-d₄)oxy)piperidin-1-yl)-3,4,6-trimethyl-6,7-dihydro-5H-pyrrolo[3,4-b]pyridin-5-one | 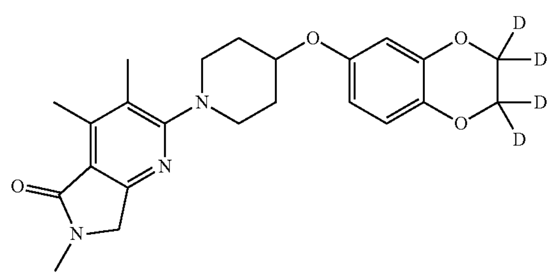 [SMILES: [2H]C1([2H])Oc2ccc(OC3CCN(c4nc5c(c(C)c4C)C(=O)N(C)C5)CC3)cc2OC1([2H])[2H]] | 414.3 |
| 13 | 2-(4-((2,3-dihydrobenzo[b][1,4]dioxin-6-yl-2,2,3,3-d₄)oxy)piperidin-1-yl)-3,4-dimethyl-6,7-dihydro-5H-pyrrolo[3,4-b]pyridin-5-one | 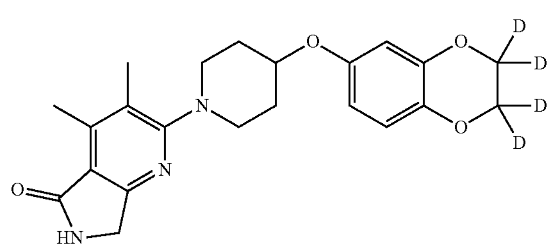 [SMILES: [2H]C1([2H])Oc2ccc(OC3CCN(c4nc5c(c(C)c4C)C(=O)NC5)CC3)cc2OC1([2H])[2H]] | 400.3 |
| A1 | 7-(4-((2,3-dihydrobenzo[b][1,4]dioxin-6-yl-2,2,3,3-d₄)oxy)piperidin-1-yl)-6-methyl-[1,2,4]triazolo[4,3-a]pyrimidin-3(2H)-one | 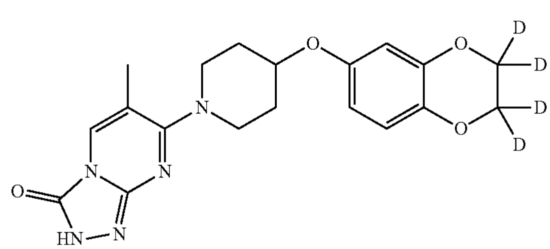 [SMILES: [2H]C1([2H])Oc2ccc(OC3CCN(c4nc5n[nH]c(=O)n5cc4C)CC3)cc2OC1([2H])[2H]] | 388.2 |

TABLE 1-continued

| Cpd. No. | Name | Structure | ES-MS [M + 1]+ |
|---|---|---|---|
| A2 | 7-(4-((2,3-dihydrobenzo[b][1,4]dioxin-6-yl-2,2,3,3-d4)oxy)piperidin-1-yl)-2-ethyl-6-methyl-[1,2,4]triazolo[4,3-a]pyrimidin-3(2H)-one | 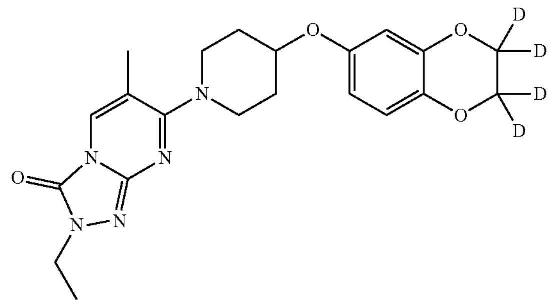 [SMILES: [2H]C1([2H])Oc2ccc(OC3CCN(c4nc5nn(CC)c(=O)n5cc4C)CC3)cc2OC1([2H])[2H]] | 416.4 |
| A3 | 7-(4-((2,3-dihydrobenzo[b][1,4]dioxin-6-yl-2,2,3,3-d4)oxy)piperidin-1-yl)-2-(2-methoxyethyl)-6-methyl-[1,2,4]triazolo[4,3-a]pyrimidin-3(2H)-one | 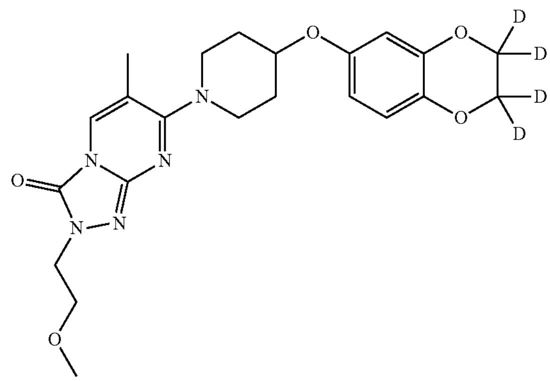 [SMILES: [2H]C1([2H])Oc2ccc(OC3CCN(c4nc5nn(CCOC)c(=O)n5cc4C)CC3)cc2OC1([2H])[2H]] | 446.4 |
| A4 | (R)-7-(4-((2,3-dihydrobenzo[b][1,4]dioxin-6-yl-2,2,3,3-d4)oxy)piperidin-1-yl)-6-methyl-2-(tetrahydrofuran-3-yl)-[1,2,4]triazolo[4,3-a]pyrimidin-3(2H)-one | 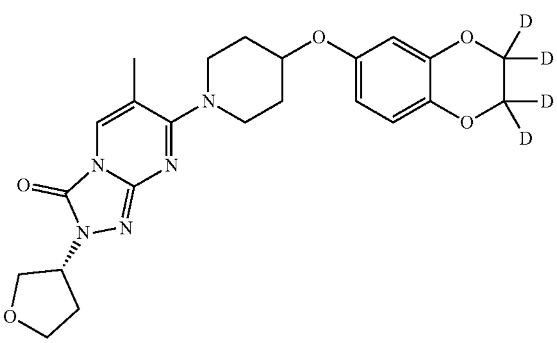 [SMILES: [2H]C1([2H])Oc2ccc(OC3CCN(c4nc5nn([C@@H]6CCOC6)c(=O)n5cc4C)CC3)cc2OC1([2H])[2H]] | 458.4 |
| A5 | (S)-7-(4-((2,3-dihydrobenzo[b][1,4]dioxin-6-yl-2,2,3,3-d4)oxy)piperidin-1-yl)-6-methyl-2-(tetrahydrofuran-3-yl)-[1,2,4]triazolo[4,3-a]pyrimidin-3(2H)-one | 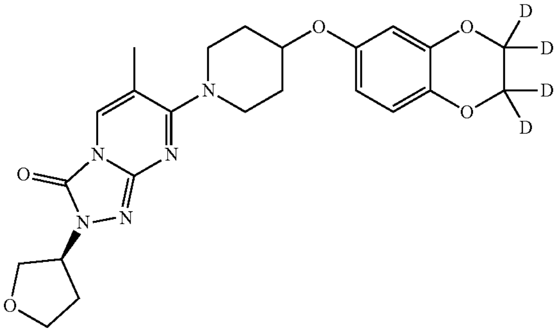 [SMILES: [2H]C1([2H])Oc2ccc(OC3CCN(c4nc5nn([C@H]6CCOC6)c(=O)n5cc4C)CC3)cc2OC1([2H])[2H]] | 458.4 |

TABLE 1-continued

| Cpd. No. | Name | Structure | ES-MS [M + 1]+ |
|---|---|---|---|
| A6 | 7-(4-((2,3-dihydrobenzo[b][1,4]dioxin-6-yl-2,2,3,3-d₄)oxy)piperidin-1-yl)-2,6-dimethyl-[1,2,4]triazolo[4,3-a]pyrimidin-3(2H)-one | 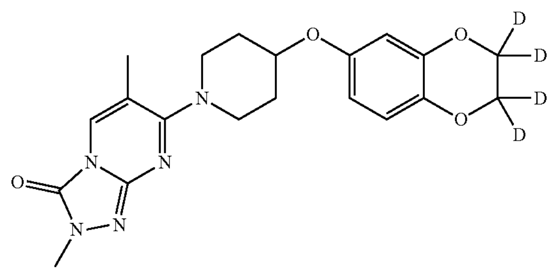 [SMILES: [2H]C1([2H])Oc2ccc(OC3CCN(c4nc5nn(C)c(=O)n5cc4C)CC3)cc2OC1([2H])[2H]] | 402.2 |
| A7 | 7-(4-((2,3-dihydrobenzo[b][1,4]dioxin-6-yl-2,2,3,3-d₄)oxy)piperidin-1-yl)-2-(1-methoxypropan-2-yl)-6-methyl-[1,2,4]triazolo[4,3-a]pyrimidin-3(2H)-one | 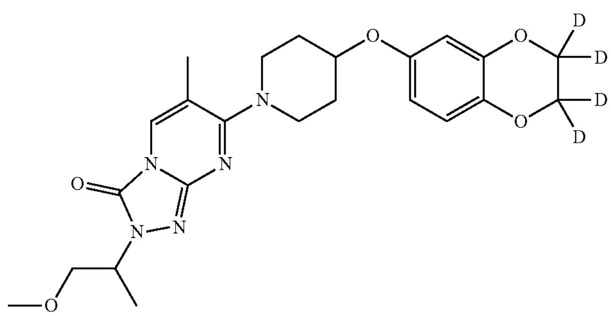 [SMILES: [2H]C1([2H])Oc2ccc(OC3CCN(c4nc5nn(C(C)COC)c(=O)n5cc4C)CC3)cc2OC1([2H])[2H]] | 460.3 |
| A8 | 7-(4-((2,3-dihydrobenzo[b][1,4]dioxin-6-yl-2,2,3,3-d₄)oxy)piperidin-1-yl)-6-methyl-2-((4-methylmorpholin-2-yl)methyl)-[1,2,4]triazolo[4,3-a]pyrimidin-3(2H)-one | 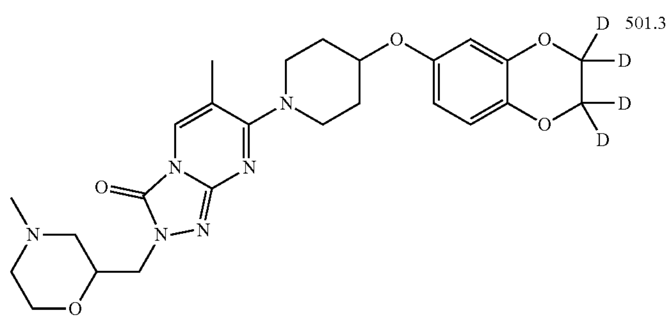 | 501.3 |
| A9 | 7-(4-((2,3-dihydrobenzo[b][1,4]dioxin-6-yl-2,2,3,3-d₄)oxy)piperidin-1-yl)-5,6-dimethyl-[1,2,4]triazolo[4,3-a]pyrimidin-3(2H)-one | 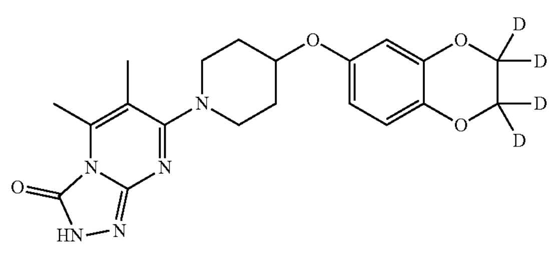 [SMILES: [2H]C1([2H])Oc2ccc(OC3CCN(c4nc5n[nH]c(=O)n5c(C)c4C)CC3)cc2OC1([2H])[2H]] | 402.3 |
| A10 | 7-(4-((2,3-dihydrobenzo[b][1,4]dioxin-6-yl-2,2,3,3-d₄)oxy)piperidin-1-yl)-2,5,6-trimethyl-[1,2,4]triazolo[4,3-a]pyrimidin-3(2H)-one | 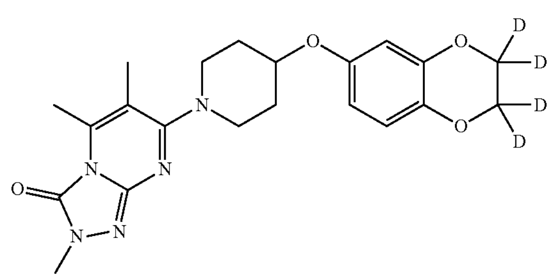 [SMILES: [2H]C1([2H])Oc2ccc(OC3CCN(c4nc5nn(C)c(=O)n5c(C)c4C)CC3)cc2OC1([2H])[2H]] | 416.4 |

TABLE 1-continued

| Cpd. No. | Name | Structure | ES-MS [M + 1]+ |
|---|---|---|---|
| A11 | 5-chloro-7-(4-((2,3-dihydrobenzo[b][1,4]dioxin-6-yl-2,2,3,3-d4)oxy)piperidin-1-yl)-2,6-dimethyl-[1,2,4]triazolo[4,3-a]pyrimidin-3(2H)-one | 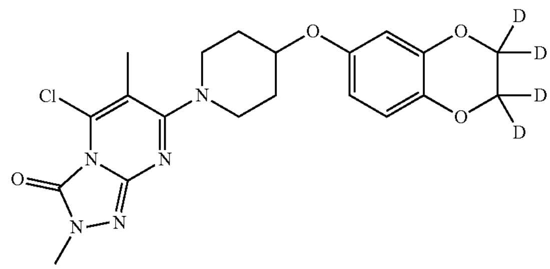 [SMILES: [2H]C1([2H])Oc2ccc(OC3CCN(c4nc5nn(C)c(=O)n5c(Cl)c4C)CC3)cc2OC1([2H])[2H]] | 436.3 |
| A12 | 5-cyclopropyl-7-(4-((2,3-dihydrobenzo[b][1,4]dioxin-6-yl-2,2,3,3-d4)oxy)piperidin-1-yl)-2,6-dimethyl-[1,2,4]triazolo[4,3-a]pyrimidin-3(2H)-one | 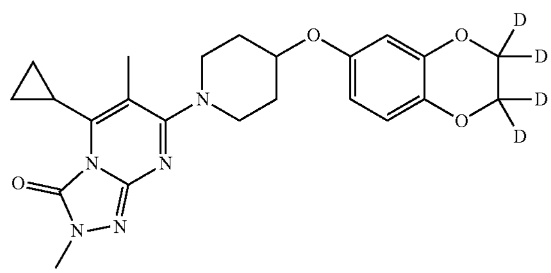 [SMILES: [2H]C1([2H])Oc2ccc(OC3CCN(c4nc5nn(C)c(=O)n5c(C5CC5)c4C)CC3)cc2OC1([2H])[2H]] | 442.3 |
| A13 | 5-cyclopropyl-7-(4-((2,3-dihydrobenzo[b][1,4]dioxin-6-yl-2,2,3,3-d4)oxy)piperidin-1-yl)-6-methyl-2-(methyl-d3)-[1,2,4]triazolo[4,3-a]pyrimidin-3(2H)-one | 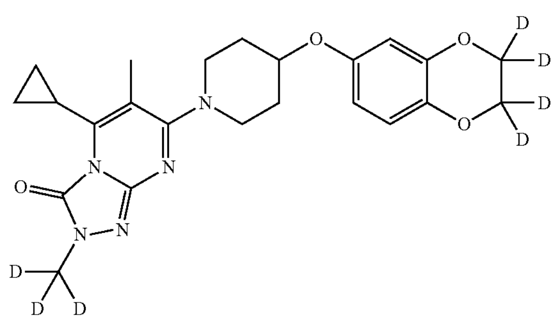 [SMILES: [2H]C([2H])([2H])n1nc2nc(N3CCC(Oc4ccc5c(c4)OC([2H])([2H])C([2H])([2H])O5)CC3)c(C)c(C3CC3)n2c1=O] | 445.4 |
| A14 | 5-(4-((2,3-dihydrobenzo[b][1,4]dioxin-6-yl-2,2,3,3-d4)oxy)piperidin-1-yl)-2-methyl-2,6,7,8-tetrahydro-1H-cyclopenta[e][1,2,4]triazolo[4,3-a]pyrimidin-1-one | 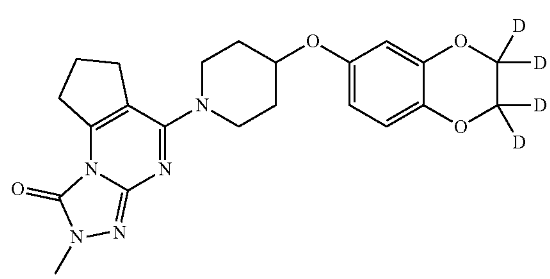 [SMILES: [2H]C1([2H])Oc2ccc(OC3CCN(c4nc5nn(C)c(=O)n5c5c4CCC5)CC3)cc2OC1([2H])[2H]] | 428.3 |
| A15 | 5-(4-((2,3-dihydrobenzo[b][1,4]dioxin-6-yl-2,2,3,3-d4)oxy)piperidin-1-yl)-2-methyl-6,7,8,9-tetrahydro-[1,2,4]triazolo[4,3-a]quinazolin-1(2H)-one | 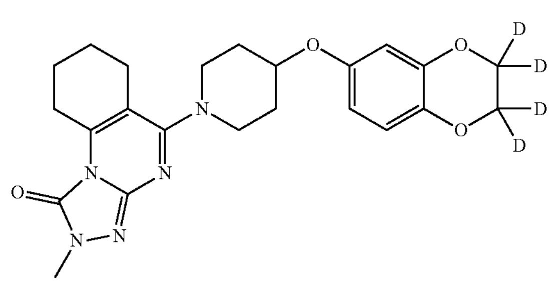 [SMILES: [2H]C1([2H])Oc2ccc(OC3CCN(c4nc5nn(C)c(=O)n5c5c4CCCC5)CC3)cc2OC1([2H])[2H]] | 442.3 |

TABLE 1-continued

| Cpd. No. | Name | Structure | ES-MS $[M + 1]^+$ |
|---|---|---|---|
| A16 | 5-(4-((2,3-dihydrobenzo[b][1,4]dioxin-6-yl-2,2,3,3-d$_4$)oxy)piperidin-1-yl)-2,6,7,8-tetrahydro-1H-cyclopenta[e][1,2,4]triazolo[4,3-a]pyrimidin-1-one | 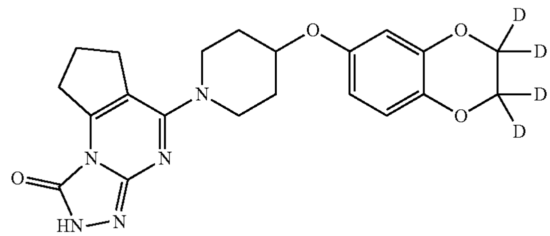 [SMILES: [2H]C1([2H])Oc2ccc(OC3CCN(c4nc5n[nH]c(=O)n5c5c4CCC5)CC3)cc2OC1([2H])[2H]] | 414.3 |
| A17 | 5-(4-((2,3-dihydrobenzo[b][1,4]dioxin-6-yl-2,2,3,3-d$_4$)oxy)piperidin-1-yl)-6,7,8,9-tetrahydro-[1,2,4]triazolo[4,3-a]quinazolin-1(2H)-one | 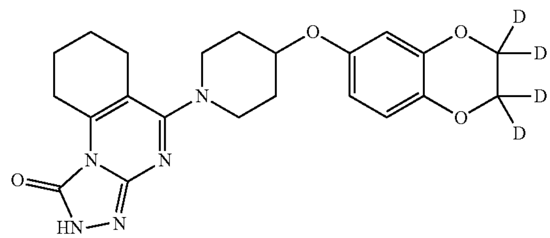 [SMILES: [2H]C1([2H])Oc2ccc(OC3CCN(c4nc5n[nH]c(=O)n5c5c4CCCC5)CC3)cc2OC1([2H])[2H]] | 428.4 |
| A18 | 7-(4-((2,3-dihydrobenzo[b][1,4]dioxin-6-yl-2,2,3,3-d$_4$)oxy)piperidin-1-yl)-5,6-dimethyl-2-(methyl-d$_3$)-[1,2,4]triazolo[4,3-a]pyrimidin-3(2H)-one | 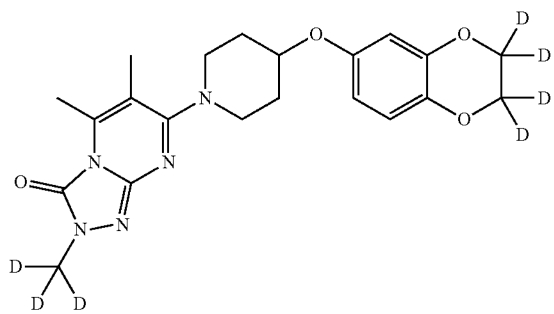 [SMILES: [2H]C([2H])([2H])n1nc2nc(N3CCC(Oc4ccc5c(c4)OC([2H])([2H])C([2H])([2H])O5)CC3)c(C)c(C)n2c1=O] | 419 |

Biological Activity

A. Cell Lines Expressing Muscarinic Acetylcholine Receptors

Human and rat $M_4$ cDNAs, along with the chimeric G protein $G_{qi5}$, were transfected into Chinese hamster ovary (CHO-K1) cells purchased from the American Type Culture Collection using Lipofectamine2000. The transfected cells were subjected to selection antibiotic treatment to generate stable cell lines; G418 sulfate (1 mg/ml) for selecting $M_4$ expressing cells and Hygromycin B (500 µg/mL) for selecting $G_{qi5}$ expressing cells. The resulting polyclones were further screened to obtain monoclones of $hM_4$-$G_{qi5}$ and $rM_4$-$G_{qi5}$ for compound screening assay. Stable monoclone cells were maintained in Ham's F-12 medium containing 10% heat-inactivated fetal bovine serum (FBS), 1× Antibiotic/Antimycotic, 20 mM HEPES, 500 µg/mL G418 sulfate, and 200 µg/mL Hygromycin B in 37° C. humidified incubators in the presence of 5% $CO_2$.

B. Cell-Based Functional Assay of Muscarinic Acetylcholine Receptor Activity

The high throughput assay was employed to measure receptor-induced mobilization of intracellular calcium to determine compound activity. Test compound was added to cells expressing the muscarinic receptors that were loaded with calcium sensitive fluorescent dye. After a ~2.5 minute incubation period, a submaximal ($EC_{20}$) concentration of acetylcholine was added, and the response measured. This kinetic assay allows for simultaneous screening and potency determination of multiple pharmacological modes of action including agonist and potentiator activity. CHO-K1 cells stably expressing muscarinic receptors were plated in growth medium lacking G418 and hygromycin at 15,000 cells/20 µL/well in Greiner 384-well black-walled, tissue culture (TC)-treated, clear-bottom plates (Greiner Bio-One). Cells were incubated overnight at 37° C. and 5% $CO_2$. The next day, calcium assay buffer (Hank's balanced salt solution (HBSS), 20 mM HEPES, 2.5 mM Probenecid, 4.16 mM sodium bicarbonate (Sigma-Aldrich, St. Louis, MO)) was prepared to dilute compounds, agonists, and Fluo-4-acetomethoxyester (Fluo-4-AM), fluorescent calcium indicator dye. Compounds were serially diluted 1:3 into 10 point concentration response curves in DMSO using the Bravo Liquid Handler (Agilent, Santa Clara, CA), transferred to a 384 well daughter plates using an Echo acoustic liquid handler (Beckman Coulter, Indianapolis, Indiana), and diluted in assay Buffer to a 2× final concentration. The agonist plates were prepared using acetylcholine (ACh, Sigma-Aldrich, St. Louis, MO) concentrations for the $EC_{20}$ and $EC_{MAX}$ responses by diluting in assay buffer to a 5× final concentration. The 2× dye solution (2.3 µM) was prepared by mixing a 2.3 mM Fluo-4-AM stock in DMSO with 10% (w/v) pluronic acid F-127 in a 1:1 ratio in assay buffer. Using a microplate washer (BioTek, Winooski, VT), cells were washed with assay buffer for 3 times to remove medium. After the final wash, 20 µL of assay buffer remained in the cell plates. Immediately, 20 µL of the 2× dye solution (final 1.15 µM) was added to each well of the cell plate using a Multidrop Combi dispenser (Thermo Fisher, Waltham, MA).

After cells were incubated with the dye solutions for 45 min at 37° C. in the presence of 5% $CO_2$, the dye solutions were removed and replaced with assay buffer using a microplate washer, leaving 20 μL of assay buffer in the cell plate.

The prepared compound, agonist, and cell plates were placed inside the Functional Drug Screening System uCell (FDSS uCell, Hamamatsu, Japan) to measure the calcium flux. The triple add protocol was used to measure Ca kinetics; Compound, ACh for $EC_{20}$, and ACh for $EC_{50}$ adds in an order. Briefly, after establishment of a fluorescence baseline for 2 seconds (excitation, 480 nm; emission, 530 nm), first add occurred by adding 20 μL of test compound to the cells, and the response was measured for 140 seconds. This is followed by second add; 10 μL (5×) of an $EC_{20}$ concentration of ACh agonist was added to the cells, and the response of the cells was measured for 125 seconds. Immediately, the third add occurred by adding 12 μl (5×) of an $EC_{50}$ concentration of ACh and the response of the cells was measured for 90 seconds. Acetylcholine-mediated maximum response ($EC_{max}$) was measured by adding 1 mM ACh as third add in the control wells. DMSO vehicle was added to the control wells in the first add for assessing ACh $EC_{20}$, $EC_{80}$, and $EC_{max}$ responses. Calcium fluorescence was recorded as fold over basal fluorescence and raw data were normalized to the maximal response to ACh agonist. Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{50}$ acetylcholine response. Concentration-response curves were generated using a four-parameter logistical equation using GraphPad Prism (La Jolla, CA) or the Dotmatics software platform (Woburn, MA).

The above-described assay was also operated in a second mode where an appropriate fixed concentration of the present compounds was added to the cells after establishment of a fluorescence baseline for about 3 seconds, and the response in cells was measured. 140 s later, the appropriate concentration of agonist was added and the calcium response (maximum-local minima response) was measured. The $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

C. Activity of Compounds in a mAChR $M_4$ Cell-Based Assay

Compounds were synthesized as described above. Activity ($EC_{50}$ and $E_{max}$) was determined in the $M_4$ cell-based functional assay as described above and the data are shown in Table 2. Also, selectivity at $M_2$ activity ($EC_{50}$ and $E_{max}$) was shown below as determined in the $M_2$ cell-based functional assay. The compound number corresponds to the compound numbers used in Table 1.

TABLE 2

| No. | Human $M_4$ $EC_{50}$ (nM) | $E_{max}$ (%)* | Human $M_2$ $EC_{50}$ (nM) | $E_{max}$ (%)* |
|---|---|---|---|---|
| 1 | 3 | 108 | 346 | 69 |
| 2 | 3 | 91 | 567 | 57 |
| 3 | 2 | 96 | 658 | 61 |
| 4 | 11 | 85 | 5870 | 57 |
| 5 | 4 | 76 | 219 | 70 |
| 6 | 9 | 78 | 867 | 64 |
| 7 | 65 | 76 | 3749 | 53 |
| 8 | 3 | 104 | 494 | 56 |
| 9 | 27 | 91 | 2240 | 57 |
| 10 | 3 | 93 | 330 | 60 |
| 11 | 5 | 73 | 508 | 60 |
| 12 | 7 | 103 | 2380 | 54 |
| 13 | 4 | 101 | inactive | |
| A1 | 5 | 100 | 367 | 78 |
| A2 | 2 | 82 | 884 | 70 |
| A3 | 8 | 79 | 5405 | 55 |
| A4 | 9 | 88 | 1385 | 68 |
| A5 | 12 | 87 | 2870 | 66 |
| A6 | 7 | 90 | 499 | 68 |
| A7 | 53 | 89 | >10,000 | 47 |
| A8 | 48 | 95 | Inactive | |
| A9 | 5 | 79 | 839 | 45 |
| A10 | 2 | 96 | 1515 | 54 |
| A11 | 12 | 90 | 6086 | 57 |
| A12 | 32 | 103 | Inactive | |
| A13 | 28 | 103 | Inactive | |
| A14 | 3 | 84 | 2230 | 60 |
| A15 | 53 | 83 | 5922 | 45 |
| A16 | 4 | 84 | 2864 | 48 |
| A17 | 64 | 87 | Inactive | |
| A18 | 3 | 98 | 1113 | 53 |

*% ACh maximum at 30 μM.

D. Functional Assessment of $M_4$ Activator Compounds in Cellular cAMP Assay Cellular cAMP $G_i$ HTRF Assay Activation of the $M_4$ receptor leads to the inhibition of cAMP production by coupling to $G_{i/o}$ proteins. To measure the level of cAMP inhibition by $M_4$ allosteric modulators, a Homogeneous Time-Resolved Fluorescence (HTRF®) cAMP assay was employed using CHO cells stably expressing human or rat $M_4$ receptors. The HTRF cAMP assay is a Time-Resolved Resonance Energy Transfer (TR-FRET) competitive immunoassay. Endogenous intracellular cAMP generated by cells competes with Europium cryptate-labeled cAMP (Europium donor, emission 665 nm) for the binding to a cAMP antibody labeled with d2 (d2-acceptor, emission 620 nm). Thus, the fluorescence emission ratio (665 nm/620 nm) is inversely proportional to the cAMP amount in the cells. Compound-mediated $M_4$ activation results in an increase in HTRF ratio (665 nm/620 nm), indicative of a decrease in intracellular cAMP level. To monitor agonist activity, compounds were added to the $M_4$ cells in the presence of an $EC_{50}$ concentration of forskolin (adenylyl cyclase activator) which induces a submaximal intracellular cAMP level. To assess potentiator activity, compounds were added to the $M_4$ cells with an $EC_{50}$ concentration of forskolin in the presence of an $EC_{20}$ concentration of acetylcholine. This functional assay allows determination of the potency and efficacy of compounds directly activating or potentiating the $G_{i/o}$-coupled $M_4$ receptor; representative data are shown in Table 3.

Functional agonist and potentiator activities of compounds were determined by measuring cAMP levels in Chinese Hamster Ovary (CHO) cells stably expressing human or rat $M_4$ muscarinic receptors using an HTRF cAMP $G_{i/o}$ kit. Cells were maintained in F12 medium containing 10% FBS, 20 mM HEPES, 1× Antibiotic/Antimycotic, and G418 (500 μg/ml) in 37° C. humidified incubators in the presence of 5% $CO_2$. The day before assay, the cells were trypsinized and resuspended in plating medium (growth medium without G418). The cells were plated to white, solid, flat-bottomed, 384 well plates at densities of 4,000 and 6,000 cells/10 L/well, of human $M_4$ and rat $M_4$ cells, respectively. The cell plates were spun at 100×g for 1 min, then immediately placed in a 37° C. incubator in the presence of 5% $CO_2$ overnight.

The next day, reagents were freshly diluted at a 2× concentration in assay buffer using F12 basal medium or stimulation buffer. All assay buffers contained 500 µM IBMX to block cAMP degradation. Activation of $M_4$ by compounds was examined in cells stimulated with an $EC_{50}$ concentration of forskolin to induce submaximal intracellular cAMP levels. Forskolin $EC_{50}$ concentrations were determined from forskolin concentration response curves (CRCs) and ranged from 1.5 to 2.5 µM. Compounds (10 mM) were prepared in 100% DMSO and further serially diluted either 1:3 or 1:5 into a 13-point CRC in DMSO using a Bravo Liquid Handler in a 384 well microplate.

Agonist assay mode was used to assess the abilities of $M_4$ compounds to directly activate $M_4$ receptors in the absence of the agonist, acetylcholine. The 10-point serially diluted compounds, starting 30 µM as a final concentration, were transferred to a compound plate using an Echo plate reformat protocol. 2× assay buffer containing an $EC_{50}$ concentration of forskolin concentration was added to the compound plate. Vehicle (1% DMSO) was added to the following control wells; baseline cAMP (no forskolin), forskolin max, and forskolin $EC_{80}$. 10 µL/well of the prepared 2× assay buffer was immediately added to the cell plates using a Bravo 384 well tip liquid handler. The cell plates were immediately spun for 30 seconds at 100×g and incubated at 37° C. for 10 min with gentle shaking at 50 rpm. An acetylcholine CRC was also performed in the presence of an $EC_{50}$ concentration of forskolin to determine the concentrations of acetylcholine inducing maximal ($EC_{max}$) and submaximal ($EC_{20}$) cAMP inhibition in order to prepare for the subsequent potentiator mode assay.

In potentiator assay mode, the 10-point serially diluted compounds, starting 1.1 µM as a final concentration, were transferred to a compound plate using an Echo plate reformat protocol. 2× assay buffer containing an $EC_{50}$ concentration of forskolin and an $EC_{20}$ concentration of acetylcholine was added to the compound plate. Vehicle (1% DMSO) was added to the following: (1) for forskolin controls wells—baseline cAMP (no forskolin), forskolin max, and forskolin $EC_{80}$, (2) for agonist control wells containing forskolin $EC_{80}$—basal (no agonist), and acetylcholine $EC_{20}$ and $EC_{max}$. 10 µL/well of the prepared 2× assay buffer was immediately added to the cell plates using a Bravo 384 well tip liquid handler. The cell plates were immediately spun for 30 seconds at 100×g and incubated at 37° C. for 10 min with gentle shaking at 50 rpm. During the 10-minute incubation period, cAMP Eu-cryptate donor (20×) and anti-cAMP d2 antibody acceptor (20×) were diluted in lysis/detection buffer in separate tubes. Immediately after the incubation, cells were lysed by sequentially adding 10 µL/well of cAMP Eu-crytate solution and 10 µL/well of anti-cAMP d2 antibody solution. The cell plates were immediately spun for 30 seconds at 100×g and incubated for 60 minutes at 25° C. with gentle shaking at 50 rpm. Immediately after the detection incubation, TR-FRET signals were measured at two channels, 665 and 620 nm, using an EnVision Plate reader (Perkin Elmer). All emission ratios (665/620) were normalized to % acetylcholine max. Individual CRCs were generated using a four-parameter logistical equation using Graph-Pad Prism (La Jolla, CA), and $EC_{50}$ was extracted from the fitting, and maximal response (% ACh Max) was determined;

$$y = \text{bottom} + \frac{\text{top} - \text{bottom}}{1 + 10^{(LogEC50-A)HillSlope}}$$

where A is the molar concentration of the compound; bottom and top denote the lower and upper plateaus of the concentration-response curve; HillSlope is the Hill coefficient that describes the steepness of the curve; and $EC_{50}$ is the molar concentration of compound required to generate a response halfway between the top and bottom.

TABLE 3

$hM_4$ cAMP Activity

| Compound No. | Agonist | | | PAM | | |
|---|---|---|---|---|---|---|
| | $EC_{50}$ (nM) | % ACh Max | | $EC_{50}$ (nM) | % ACh Max | |
| 3 | 20 | 106 | n = 3 | 6 | 94 | n = 3 |
| A6 | 16 | 89 | n = 2 | 3 | 70 | n = 2 |
| A10 | 7 | 105 | n = 2 | 2 | 82 | n = 2 |

TABLE 4

Materials and Equipment

| | Item | Manufacturer | Cat # |
|---|---|---|---|
| Cell culture | F12 medium | Thermo Fisher | 11765054 |
| | Fetal bovine serum | Thermo Fisher | 16140089 |
| | Antibiotic/Antimycotic | Thermo Fisher | 15240062 |
| | 1M HEPES (2-[4-(2-hydroxyethyl)piperazin-1-yl]ethanesulfonic acid) | Thermo Fisher | 15630080 |
| | G418 Sulfate | Thermo Fisher | 10131027 |
| | TrypLE Express | Thermo Fisher | 12605036 |
| cAMP Assay | HTRF CAMP-Gi kit | Cisbio | 62AM9PEC |
| | CELLSTAR, 384 well plate, TC-treated, White, Solid-flat bottom | Greiner | 781080 |
| | IBMX (3-isobutyl-1-methylxanthine) | Sigma | I5879 |
| | Forskolin | Sigma | F6886 |
| | Acetylcholine chloride | Sigma | A6625 |
| | DMSO (Dimethyl sulfoxide) | Sigma | D8418 |
| | Echo 650 liquid handler | Beckman | 001-16079 |
| | Bravo liquid handler | Agilent | G5563AA |
| | EnVision plate reader | Perkin Elmer | 2105-0011 |

E. Effects of Compounds on Amphetamine-Induced Hyperlocomotion in Rats

The ability of compound 3 to reverse amphetamine-induced hyperlocomotion, a preclinical model predictive of antipsychotic-like activity (Stanhope et al. (2001) *J Pharmacol Exp Ther.* 299:782-792), was evaluated in male Sprague-Dawley rats.

Drugs: d-Amphetamine hemisulfate was obtained from Sigma (St. Louis, MO). Salt-correction was used to determine the correct amount of the d-amphetamine hemisulfate form in milligrams to add to sterile water in order to yield a 0.75 mg/mL solution, which would be dosed at 1 mL/kg body weight of each animal. Compound 3 and the comparator compound VU0467154 (a reported mAChR $M_4$ PAM, Bubser et al. *ACS Chem. Neurosci.* 2014, 5(10):920-942) were formulated in volumes specific to the number of animals dosed each day at the particular dosage. The solutions were formulated so that animals were injected with a volume equal to 10 mL/kg body weight for all compounds. The appropriate amount according to the dosage was mixed in 10% Tween 80 (Sigma) in sterile water. The mixtures were then vortexed and stored in a 39° C. sonication bath for 1 hour, until in a solution or microsuspension (depending on dose).

Animals: Male Sprague-Dawley rats weighing 239-300 grams and averaging 265 g (Harlan, Inc., Indianapolis, IN) were used. They were housed in the animal care facility certified by the American Association for the Accreditation of Laboratory Animal Care (AALAC) under a 12-hour light/dark cycle (lights on: 6 a.m.; lights off: 6 p.m.) and had free access to food and water. The animals used in this experiment were food-deprived the evening before experimentation for oral dosing of compound/vehicle. The experimental protocols performed during the light cycle were approved by the Institutional Animals Care and Use Committee of Vanderbilt University and conformed to the guidelines established by the National Research Council Guide for the Care and Use of Laboratory Animals.

Amphetamine-induced Hyperlocomotion: Male Harlan Sprague Dawley rats were habituated in Smart Open Field locomotor activity test chambers (Hamilton-Kinder, San Diego, CA) with 16×16 photo beams to automatically record locomotor activity. After 30 minutes of monitoring, animals were dosed by way of oral gavage with vehicle or compound—either compound 3 or VU0467154. They were monitored for an additional 30 minutes and then injected subcutaneously with vehicle or 0.75 mg/kg amphetamine. Animals were then monitored for an additional 60 minutes, for a total of 120 minutes. Data were expressed as changes in ambulation defined as total number of beam breaks per 5 minute interval. Terminal brain and plasma samples were collected at the end of the study for pharmacokinetic analysis.

Data Analysis: Behavioral data were analyzed using a two-way ANOVA with main effects of treatment and time. Post hoc analysis was performed using a Dunnett's t-test with all treatment groups compared to the Vehicle/amphetamine group (VAMP) group using GraphPad Prism V.5.04 (GraphPad Software, San Diego, CA). Data were graphed using GraphPad Prism V.5.04 (GraphPad Software, San Diego, CA). A probability of p<0.05 was taken as the level of statistical significance. In addition, the total number of beam breaks from the amphetamine administration (65 min) to the end of the study (120 min) was calculated and graphed. Percent Reversal was calculated as follows using Microsoft Excel: In each animal, total ambulation from t=65 to t=120 was summed. The mean of each sum was calculated in the VAMP group. Then, for each animal, Percent Reversal was calculated with the following formula: Percent Reversal=100−{[(total ambulation in each animal from t=65 to t=120)/(mean of each sum from t=65 to t=120 in VAMP group)]*100}. The mean Percent Reversal, as well as the standard error, was calculated for each dose group using GraphPad Prism V5.04.

Results: Compound 3 dosed at 1 mg/kg, 1.8 mg/kg, 3 mg/kg and 5.6 mg/kg, and VU0467154 dosed at 10 mg/kg, reversed amphetamine-induced hyperlocomotion with percent reversals of 27.5%, 40.1%, 59.1%, 60.9%, and 56.2% respectively. Data are illustrated in the FIGURE.

Conclusions: Systemic administration of the $M_4$ PAM compound 3 caused a significant and sustained reversal of amphetamine-induced hyperlocomotion to a similar extent as the comparator $M_4$ PAM compound VU0467154 at 10 mg/kg p.o., suggesting that these compounds have antipsychotic-like effects in this animal model.

F. In Vitro Secondary Pharmacology and Toxicity

Compound 3 was tested using Eurofins LeadProfilingScreen®, which detects potential adverse activity, additional unexpected activity and relative selectivity and specificity. The screen includes 68 primary molecular targets, including several CNS targets recommended by the EMEA to evaluate drug dependence potential. Compound 3 exhibited <50% inhibition of each target in the LeadProfilingScreen®, at 10 µM (binding).

Compound 3 was further tested using Eurofins Ames Test. The Ames test is a widely used bacterial assay for the identification of compounds that can produce gene mutations, and it shows a high predictive value with rodent carcinogenicity tests. The Ames test used four strains of *Salmonella* with pre-existing mutations that rendered the bacteria unable to synthesize the essential amino-acid histidine, and, as a result, unable to grow in histidine-free medium. If a compound induces mutations in these particular genes, it can restore gene function, allowing the cells to regain the capacity to synthesize histidine and therefore grow in its absence ("reversion assay"). Compound 3 tested clean in this assay, at 5-100 µM.

G. In vitro and in vivo Drug Metabolism and Pharmacokinetics (DMPK)

Compounds may be tested in in vitro assays to investigate both metabolism and pharmacokinetics. These assays may be performed according to known methods as generally described in the following references: Conde-Ceide et al. *ACS Med. Chem. Lett.* 2015, 6, 716-720; Morris et al. *J. Med. Chem.* 2014, 57, 10192-10197; and Bubser et al. *ACS Chem. Neurosci.* 2014, 5, 920-942. In vitro DMPK data for Compound 3 are listed in the following table.

| Assay | Result |
| --- | --- |
| MDCK-MDR1 ER | 1.3 ($P_{app}$ A→ B: 45.5 × $10^{-6}$ cm/s) |
| Rat $F_u$ (plasma) | 0.026 |
| Dog $F_u$ (plasma) | 0.042 |
| Cyno $F_u$ (plasma) | ND |
| Human $F_u$ (plasma) | 0.022 |
| Rat $F_u$ (brain) | 0.015 |
| Rat $CL_{int}$ (mL/min/kg) | 90 |
| Dog $CL_{int}$ (mL/min/kg) | 19 |
| Cyno $CL_{int}$ (mL/min/kg) | ND |
| Human $CL_{int}$ (mL/min/kg) | 15 |
| P450 3A4 $IC_{50}$ (µM) | >100 |
| P450 2D6 $IC_{50}$ (µM) | >100 |
| P450 2C9 $IC_{50}$ (µM) | >100 |
| P450 1A2 $IC_{50}$ (µM) | >100 |

The in vivo pharmacokinetic data listed in the following table for Compound 3 was determined from pharmacokinetic studies in rat or dog, according to known methods as generally described in the following references: Garrison et al. *J. Med. Chem.* 2022, 65, 6273-6286; Felts et al. *J. Med. Chem* 2017, 60, 5072-5085; and Yu et al. *J. Med. Chem.* 2021, 64, 4709-4729.

| Assay | Result |
|---|---|
| Rat $CL_p$ (mL/min/kg) | 16.9 |
| Dog $CL_p$ (mL/min/kg) | 1.8 |
| Rat $V_{ss}$ (L/kg) | 1.6 |
| Dog $V_{ss}$ (L/kg) | 1.0 |
| Rat Elim. $t_{1/2}$ (hr) | 1.4 |
| Dog Elim. $t_{1/2}$ (hr) | 7.6 |
| Rat oral F (3 mg/kg) | >100% |
| Dog oral F (3 mg/kg) | 89% |
| Rat brain: plasma $K_p$ | 1.2 |
| Rat brain: plasma $K_{p, uu}$ | 0.7 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound

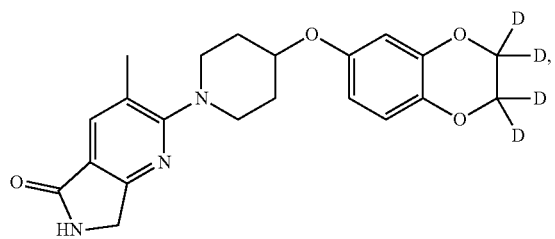

or a pharmaceutically acceptable salt thereof, that has at least 25% deuterium incorporation at each deuterium label.

2. The compound of claim 1, or a pharmaceutically acceptable salt thereof, that has at least 50% deuterium incorporation at each deuterium label.

3. The compound of claim 2, or a pharmaceutically acceptable salt thereof, that has at least 75% deuterium incorporation at each deuterium label.

4. The compound of claim 3, or a pharmaceutically acceptable salt thereof, that has at least 90% deuterium incorporation at each deuterium label.

5. The compound of claim 4, or a pharmaceutically acceptable salt thereof, that has at least 99.5% deuterium incorporation at each deuterium label.

6. The compound of claim 5, or a pharmaceutically acceptable salt thereof, that has at least 99.9% deuterium incorporation at each deuterium label.

7. A pharmaceutical composition comprising the compound of claim 1, or a pharmaceutically acceptable salt thereof, and a pharmaceutically acceptable carrier.

\* \* \* \* \*